United States Patent
Varenne et al.

(10) Patent No.: US 11,930,756 B2
(45) Date of Patent: Mar. 19, 2024

(54) WHEAT COMPRISING MALE FERTILITY RESTORER ALLELES

(71) Applicants: LIMAGRAIN EUROPE, Saint Beauzire (FR); BIOGEMMA, Chappes (FR)

(72) Inventors: Pierrick Varenne, Fontainebleau (FR); Jordi Comadran, Riom (FR); Sébastien Specel, Montpensier (FR); Mickaël Throude, Beauregard (FR); Jérémy Derory, Royat (FR)

(73) Assignee: LIMAGRAIN EUROPE, Saint Beauzire (FR)

(*) Notice: Subject to any disclaimer, the term of this patent is extended or adjusted under 35 U.S.C. 154(b) by 185 days.

(21) Appl. No.: 17/334,472

(22) Filed: May 28, 2021

(65) Prior Publication Data

US 2021/0345575 A1 Nov. 11, 2021

Related U.S. Application Data

(63) Continuation-in-part of application No. 16/760,693, filed as application No. PCT/EP2018/079816 on Oct. 31, 2018.

(30) Foreign Application Priority Data

| Oct. 31, 2017 | (EP) | 17306500 |
| Oct. 31, 2017 | (EP) | 17306501 |
| Jan. 12, 2018 | (EP) | 18305027 |
| Aug. 14, 2018 | (EP) | 18306114 |

(51) Int. Cl.
*A01H 5/10* (2018.01)
*A01H 6/46* (2018.01)
*C12Q 1/6895* (2018.01)

(52) U.S. Cl.
CPC .......... *A01H 6/4678* (2018.05); *A01H 5/10* (2013.01); *C12Q 1/6895* (2013.01); *C12Q 2600/13* (2013.01)

(58) Field of Classification Search
CPC .................................................. A01H 6/4678
See application file for complete search history.

(56) References Cited

FOREIGN PATENT DOCUMENTS

| WO | 2017/158126 A1 | 9/2017 |
| WO | 2017/158128 A1 | 9/2017 |
| WO | 2018/015403 A1 | 1/2018 |

OTHER PUBLICATIONS

Ma, Z.Q. et al., Crop Science (1995) vol. 35, pp. 1137-1143. (Year: 1995).*
Wurschum, T. et al., Theor Appl Genet (2017) 130:1253-1266. (Year: 2017).*
"protein Rf1, mitochondrial-like (*Aegilops tauschii* subsp. *tauschii*);" DATABASE Protein [Online]; XP002781672; 2017; Database accession No. XP_020157157.1 sequence.
Geyer et al.; "Distribution of the fertility-restoring gene Rf3 in common and spelt wheat determind by an informative SNP marker;" Mol Breeding; 2016; pp. 1-11; vol. 36, No. 167.
Geyer et al.; "Exploring the generics of ferility restoration controlled by Rf1 in common wheat (*Triticum aestivum* L.) using high-density linkage maps;" Molecular Genetics and Genomics; 2018; pp. 451-462; vol. 293, No. 2.
Fujii et al.; "Selection patterns on restrorer-like genes reveal a conflict between nuclear and mitochondrial genomes throughout angiosperm evolution;" PNAS; 2011; pp. 1723-1728; vol. 108, No. 4.
Lilienfeld; "H. Kihara: Genome-Analysis in Triticu and Aegilops. X. Concluding Review;" Cytologia; 1951; pp. 101-123; vol. 16.
Ahmed et al.; "QTL analysis of fertility-restoration against cytoplasmic male sterility in wheat;" Gene Genet. Syst.; 2001; pp. 33-38; vol. 76.
Zhou et al.; "SSR markers associated with fertility restoration genes against Triticum timopheevii cytoplasm in Triticum aestivum;" Euphytica; 2005; pp. 33-40; vol. 141.
Ma et al.; "Cell Biology & Molecular Genetics;" Crop Sci.; 1995; pp. 1137-1143; vol. 35.
Wilson et al.; "Hybrid Wheat Breeding and Commerical Seed Development;" Plant Breeding Reviews; 1984; pp. 303-319.
Stojalowski et al.; "The importance of chromosomes from the sixth homeologic group in the restoration of male fertility in winter triticale with Triticum timopheevii cytoplasm;" J Appl Genetics; 2013; pp. 179-184; vol. 54.
Wurschum et al.; Genetic architecture of male fertility restoration of Triticum timopheevii cytoplasm and fine-mapping of the major restorer locus Rf3 on chromosome 1B; Theor Appl Genet; 2017; pp. 1-23.
Brenchley et al.; "Analysis of the bread wheat genome using whole-genome shotgun sequencing;" Nature; 2012; pp. 705-710; vol. 491.
Wickersham et al.; "Male-Fertility Restoration in Crosses of R5 with Soft Red Winter Wheats;" Crop Science; 1980; pp. 100-102; vol. 20.
Zhang et al.; "Location of the Fertility Restorer Gene for T-Type CMS Wheat by Microsatellite Marker," Act Genetica Sinica; 2003; pp. 459-464; vol. 30, No. 5.
Bahl et al.; "Chromosomal Location of Male Fertility Restoring Genes in Six Lines of Common Wheat;" Crop Science; 1973; pp. 317-320; vol. 13.
Ling et al.; Draft genome of the wheat A-genome progenitor Triticum urartu; Nature; 2013; pp. 87-90; vol. 496.
Dec. 19, 2018 Search Report issued in International Patent Application No. PCT/EP2018/079816.

(Continued)

*Primary Examiner* — Russell Kallis
(74) *Attorney, Agent, or Firm* — Oliff PLC

(57) ABSTRACT

A method of plant genetics and plant breeding including wheat plants carrying restorer of fertility genes specific to *T. timopheevii* CMS cytoplasm.

32 Claims, No Drawings
Specification includes a Sequence Listing.

(56) References Cited

OTHER PUBLICATIONS

Apr. 6, 2022 Office Action issued in U.S. Appl. No. 16/760,693.
Oct. 27, 2022 Office Action Issued In U.S. Appl. No. 16/760,693.
May 23, 2023 Office Action issued in U.S. Appl. No. 16/760,693.

\* cited by examiner

SEQUENCE LISTING

```
<160> NUMBER OF SEQ ID NOS: 270

<210> SEQ ID NO 1
<211> LENGTH: 71
<212> TYPE: DNA
<213> ORGANISM: Triticum aestivum

<400> SEQUENCE: 1
gacaaagttg aggtgaacaa aacaggccta caatcmgcta acttacgtat atccacatta      60
gcacacacca c                                                          71

<210> SEQ ID NO 2
<211> LENGTH: 71
<212> TYPE: DNA
<213> ORGANISM: Triticum aestivum

<400> SEQUENCE: 2
```

```
aaattcgaca agtactatgg ctatgtctct gaatgyttgt ttggttttat ttgtctatat    60
tgtcgttgta t                                                        71

<210> SEQ ID NO 3
<211> LENGTH: 71
<212> TYPE: DNA
<213> ORGANISM: Triticum aestivum

<400> SEQUENCE: 3
atgcaaagta gtactcgtag agagttaaca cagacsagtg atttattggg tggtattcta    60
cttgatattt g                                                        71

<210> SEQ ID NO 4
<211> LENGTH: 201
<212> TYPE: DNA
<213> ORGANISM: Triticum aestivum

<400> SEQUENCE: 4
ataaagaaaa gtagaggaag cttatgaata aaatggaaaa ggaattcaaa attgccgata    60
aatataaaac tcataacaaa tctagccacg caaatgcccg ygccgctctg ctcgtttgta   120
catgtctcgg tggacaagga agaacccaac aattgcacag gtcaatctta tccagcaaaa   180
caaggaagca aaccaaacag g                                             201

<210> SEQ ID NO 5
<211> LENGTH: 80
<212> TYPE: DNA
<213> ORGANISM: Triticum aestivum

<400> SEQUENCE: 5
atgttgcctc tcgctagccg ctgtcgmacc caatgaataa tgttkmtggg ttctggctcc    60
gagaggatgg ccggctyccc                                               80

<210> SEQ ID NO 6
<211> LENGTH: 53
<212> TYPE: DNA
<213> ORGANISM: Triticum aestivum

<400> SEQUENCE: 6
gttccttgtg acatgtactc atamacaaga gccatatact ccccatcctt gca           53

<210> SEQ ID NO 7
<211> LENGTH: 201
<212> TYPE: DNA
<213> ORGANISM: Triticum aestivum

<400> SEQUENCE: 7
gacataatgt gtaataacag cccataatgc aataaatatc aatataaaag catgatgcaa    60
aatggacgta tcattgccac graaaaaatc tcacaagatg wgaccatttg atcctcrtaa   120
ttgttgttct agacccactc ctaagtmtaa cattctttat gtctatyctt caaatcccga   180
agagtaatga aaactatcga a                                             201

<210> SEQ ID NO 8
<211> LENGTH: 201
<212> TYPE: DNA
<213> ORGANISM: Triticum aestivum

<400> SEQUENCE: 8
ccatgagtac ccgctactat cgatctccct cctccctgta ggaggcctac gaacgatgcc    60
```
ctcaggtcct gcttcctctc ggtagcgatg gatccacctg yggttgctct ctcaggaacc    120
agtgttggcg gcggctcatc cggggcgctg gatcttggtg atgtgctgga acaactcaac    180
ttggaagacg aagaatttga t                                              201

<210> SEQ ID NO 9
<211> LENGTH: 71
<212> TYPE: DNA
<213> ORGANISM: Triticum aestivum

<400> SEQUENCE: 9
gacaatatga ttcaccctag atccttcacc ttacarttcg aaaaaaataa aagaacaaaa     60
gtaatttgac a                                                          71

<210> SEQ ID NO 10
<211> LENGTH: 71
<212> TYPE: DNA
<213> ORGANISM: Triticum aestivum

<400> SEQUENCE: 10
acgaagatga ggaaggtctt catgttgggt ttatgrttac taatacttgc ttggaataga     60 tgttttttgat c                                                         71

<210> SEQ ID NO 11
<211> LENGTH: 121
<212> TYPE: DNA
<213> ORGANISM: Triticum aestivum

<400> SEQUENCE: 11
gttaccccaa tatgctccct ccttgcacat tttcttcagc tgcataaaaa mcagaatacc     60
rcatcagttg cctgaacctt aacgcaggtg cagaaataag gcgacataat ttycactaat   120
c                                                                    121

<210> SEQ ID NO 12
<211> LENGTH: 71
<212> TYPE: DNA
<213> ORGANISM: Triticum aestivum

<400> SEQUENCE: 12
aggaaaataa attgttcaca acatggacat gagaaygggg caaccaaaaa gggaagaaca     60
ttggaggaaa c                                                          71

<210> SEQ ID NO 13
<211> LENGTH: 71
<212> TYPE: DNA
<213> ORGANISM: Triticum aestivum

<400> SEQUENCE: 13
tttgtactgc acgtagtaag tattgatttt tctgtktgct ctctgtggac ttagatttga     60
aaattggcct t                                                          71

<210> SEQ ID NO 14
<211> LENGTH: 71
<212> TYPE: DNA
<213> ORGANISM: Triticum aestivum

<400> SEQUENCE: 14
atgcacattg tttccatgtt aagcttatat tgtgcrtaac tcaaaagatt gaaatggaat     60

```
taccaaaggg c                                                           71

<210> SEQ ID NO 15
<211> LENGTH: 71
<212> TYPE: DNA
<213> ORGANISM: Triticum aestivum

<400> SEQUENCE: 15
actgactgtt ggaatctgat taagacgctg gagaayccga gccaagatat gtcacgacta     60
ggccatctgg a                                                          71

<210> SEQ ID NO 16
<211> LENGTH: 57
<212> TYPE: DNA
<213> ORGANISM: Triticum aestivum

<400> SEQUENCE: 16
tgggaagctt gataaggcta tgcttatatt taragatatg cagaaacaag gagtgag        57

<210> SEQ ID NO 17
<211> LENGTH: 71
<212> TYPE: DNA
<213> ORGANISM: Triticum aestivum

<400> SEQUENCE: 17
aatcagatcc tgttaatgct gtagccattc ttgcargcga caccttgtcc cagtcgtctt     60
atgggcactt a                                                          71

<210> SEQ ID NO 18
<211> LENGTH: 101
<212> TYPE: DNA
<213> ORGANISM: Triticum aestivum

<400> SEQUENCE: 18
ggcagagccg gtcgacggag aggagcgcca ttcgacgcgt cttccgcaat rtgtttgcct     60
gcttcggccg cggccattcg gcgagctccc acgcttcgtc c                        101

<210> SEQ ID NO 19
<211> LENGTH: 71
<212> TYPE: DNA
<213> ORGANISM: Triticum aestivum

<400> SEQUENCE: 19
cgtttaaaag aacacaaatg tggccctagt gatcargtac acatatttgt cacctctttg     60
aatcttactt a                                                          71

<210> SEQ ID NO 20
<211> LENGTH: 108
<212> TYPE: DNA
<213> ORGANISM: Triticum aestivum

<400> SEQUENCE: 20
cgggctgatg aggctctcga cgtgctgctt cacaggatgc ctgagctggg ctgcacyccc     60
aacgtggtgg catataccac ggtcatccac ggcttcttta aggaaggc                 108

<210> SEQ ID NO 21
<211> LENGTH: 106
<212> TYPE: DNA
<213> ORGANISM: Triticum aestivum

<400> SEQUENCE: 21
```

```
gcgctatccg gcgtcgtgtt ccctcttggg ggaatcgtcc tggagatgga tccggtcara    60
ggggcccgtg atttgtgagg atgtgtgtgt tgtttcccga aaggcg                   106

<210> SEQ ID NO 22
<211> LENGTH: 110
<212> TYPE: DNA
<213> ORGANISM: Triticum aestivum

<400> SEQUENCE: 22
ctttgacctt aaattcttgt actaatttag cagaatcgtt cttcgagaag cactcmaaaa    60
atggtttgtc ttgggtctgt atcatatttt ctctgaacaa acaggcgtga              110

<210> SEQ ID NO 23
<211> LENGTH: 106
<212> TYPE: DNA
<213> ORGANISM: Triticum aestivum

<400> SEQUENCE: 23
gacttagcct cacacggaat cgagtcaacc aattccygtc ggttttgagt ggctcccttg    60
aagatgcaat cgttttcagc atggtcagat taatcagcga gcgtgc                  106

<210> SEQ ID NO 24
<211> LENGTH: 113
<212> TYPE: DNA
<213> ORGANISM: Triticum aestivum

<400> SEQUENCE: 24
catgtagtgg ctggcgtcta agcgcctttt cttcttccag catctaygac ttagcctcac    60
acggaatcga gtcaaccaat tcctgtcggt tttgagtggc tcccttgaag atg          113

<210> SEQ ID NO 25
<211> LENGTH: 88
<212> TYPE: DNA
<213> ORGANISM: Triticum aestivum

<400> SEQUENCE: 25
gtcgtatata ttgtttgtat taaaaagttg tgtgttttgm gtcataattt ttaaaatatt    60
attatgtcat tttcaaattc gcatcaac                                       88

<210> SEQ ID NO 26
<211> LENGTH: 97
<212> TYPE: DNA
<213> ORGANISM: Triticum aestivum

<400> SEQUENCE: 26
aatcttcttg acttcatcca tccgccttgt tgccctgcgc aaaatcaaac tycccgtcc     60 ttatcatcaa gtcaggtccc gccctgggca gagagag                             97

<210> SEQ ID NO 27
<211> LENGTH: 73
<212> TYPE: DNA
<213> ORGANISM: Triticum aestivum

<400> SEQUENCE: 27
cggcagatat cacaaagggc tatcctggtg aacaayaaga tgggtcagaa tttgataatg    60
aagcctcaag ccc                                                       73

<210> SEQ ID NO 28
```

```
<211> LENGTH: 201
<212> TYPE: DNA
<213> ORGANISM: Triticum aestivum

<400> SEQUENCE: 28
aatagatgca cgcatcggcg accatttttt agtactttt gcctttttg aaaattttgt      60 cattaaaaga caaatgccta gtctatacct gataaactaa watcatacat agagaaaatg    120
gtcatttggt tgagtttcgg tacatgctga gatggttgca cttcggtgca tctgctttgc    180
ttccatcaca tcataatgtc t                                              201

<210> SEQ ID NO 29
<211> LENGTH: 65
<212> TYPE: DNA
<213> ORGANISM: Triticum aestivum

<400> SEQUENCE: 29
gctgcttgta gcgtcccca tggcacctgy gaagaggttt tcggccacag agaaggggaa     60
ggctc                                                                65

<210> SEQ ID NO 30
<211> LENGTH: 201
<212> TYPE: DNA
<213> ORGANISM: Triticum aestivum

<400> SEQUENCE: 30
aaaattactt ttcacgcgct tcgttggtct gacagtgcga gcataatttt acttttctc     60 agttttactt aatttggtta accaaatcct ttttgatttt kaactagaaa accgaatgtc   120
aaacattgtg caaatttgga aactgaaact gaaaccaaaa acctaaaaaa atgattagtt   180 tgttttttg ttcttgtttc g                                              201

<210> SEQ ID NO 31
<211> LENGTH: 66
<212> TYPE: DNA
<213> ORGANISM: Triticum aestivum

<400> SEQUENCE: 31
gtatttctta ggattttctc accggcatct ccrtttttg agcaagagta tttaaggatg     60
gtaggc                                                               66

<210> SEQ ID NO 32
<211> LENGTH: 201
<212> TYPE: DNA
<213> ORGANISM: Triticum aestivum

<400> SEQUENCE: 32
aacaaagatg ctagtaagaa catgaaccta gttgctcatt tttaacaaca attgcccacc    60
aacctgacat gctcttccca tgttctttt ttgctcaaaa yagagatgct agtccaaata   120
tttttctagt tgcttacatt ttaaacaaca attgcctacc atccttaaat actcttgctc   180
aaaaaacgga gatgccggtg a                                              201

<210> SEQ ID NO 33
<211> LENGTH: 60
<212> TYPE: DNA
<213> ORGANISM: Triticum aestivum

<400> SEQUENCE: 33
aatacagact gggtgcaaag ccaagatgat wgtaaaattg attgatggcc gttgggaggt    60
```

<210> SEQ ID NO 34
<211> LENGTH: 201
<212> TYPE: DNA
<213> ORGANISM: Triticum aestivum

<400> SEQUENCE: 34
tgtaaagaag cttaaccagg aaagctatca gggccatagg gaatggctgg ttagtgacaa    60
ttttgcctgc tggaaatggg atttcttgtt tatttcagtt ytgcattgtg tctgacatgc   120
tctttctttt gggcgcaggc tgaagtgaat taccttggac aactatcgca cccgaatctt   180
gtaaagctcg ttgggtactg t                                             201

<210> SEQ ID NO 35
<211> LENGTH: 87
<212> TYPE: DNA
<213> ORGANISM: Triticum aestivum

<400> SEQUENCE: 35
tggcggagct ggggctgttc ctcctacgca ggcgaaactt cgccgcgata aayggaacta    60
tcatcaggtt ccccgatgat ccatacg                                        87

<210> SEQ ID NO 36
<211> LENGTH: 81
<212> TYPE: DNA
<213> ORGANISM: Triticum aestivum

<400> SEQUENCE: 36
acaagcaacc gagacaagtt gctcttaatt atctgtgcgt rcacctctaa gtcttaacct    60
gacgtaacca accaaccgtg t                                              81

<210> SEQ ID NO 37
<211> LENGTH: 90
<212> TYPE: DNA
<213> ORGANISM: Triticum aestivum

<400> SEQUENCE: 37
gatggttaca aggcatgcat agcaagtaga gttaacttat caagttattr gtattttct     60 tctgtggtac ttagagtcta magcttgagc                                     90

<210> SEQ ID NO 38
<211> LENGTH: 201
<212> TYPE: DNA
<213> ORGANISM: Triticum aestivum

<400> SEQUENCE: 38
aatgaaagct gatgtgcgtt agcgataaag caacagcgat aacgacgcat ggatcaccat    60
gctacttggg gaagcaggga catctgatga gccagcatac mcccagatat gtgtctttcc   120
aaattccacg tcccaacaga tgagctataa attaatgcca ccttcctcct acagctaaat   180
actccatccg tttcataatg t                                              201

<210> SEQ ID NO 39
<211> LENGTH: 201
<212> TYPE: DNA
<213> ORGANISM: Triticum aestivum

<400> SEQUENCE: 39
cagaggcatt cgtgaattgg gcgaaatcag aagcaaggag cagcgatgtt cagcgcagaa    60

```
ggcactggga ggggattcca ggaggctgc ccaccagccc rccatcagat acggaggagg    120
tggatccatg gccctacctg tgtcctgcgc cgaatctgga ctgtggtaac tacagcgcct    180
gaatctagag gttcagcctg g                                              201
```

<210> SEQ ID NO 40
<211> LENGTH: 201
<212> TYPE: DNA
<213> ORGANISM: Triticum aestivum

<400> SEQUENCE: 40

```
gatccatctc ccttaataat tttgctattg gtattgggta tggacatctg aagtgaaggt    60
tacggccgat ttataggagt gatagcacca cacaattcat magagcatct gcaatagatg    120
agtagatgta aaactactta acttttacat ctccgggcct aaaaacgcat ctgtaataag    180
ataatgtaga tgtaaagaaa a                                              201
```

<210> SEQ ID NO 41
<211> LENGTH: 101
<212> TYPE: DNA
<213> ORGANISM: Triticum aestivum

<400> SEQUENCE: 41

```
cgacgacgac gaggatgccg agtttgatga catggaggat tatatcgacg rcgcggactg    60
ggacgccgac atgtatgatg atgtgttcga tgtctgaagg a                        101
```

<210> SEQ ID NO 42
<211> LENGTH: 61
<212> TYPE: DNA
<213> ORGANISM: Triticum aestivum

<400> SEQUENCE: 42

```
tagccgtagg tcgtagcaca tagccgttta ygtaatgcat agttgtccga aggaatgttt    60
c                                                                    61
```

<210> SEQ ID NO 43
<211> LENGTH: 71
<212> TYPE: DNA
<213> ORGANISM: Triticum aestivum

<400> SEQUENCE: 43

```
taacctgggg cttcttttt ctccctataa tatggrctgc ccttttaaga aggaactgca     60
gcgagggtgc a                                                         71
```

<210> SEQ ID NO 44
<211> LENGTH: 120
<212> TYPE: DNA
<213> ORGANISM: Triticum aestivum

<400> SEQUENCE: 44

```
ctattcgatg ggcgtgtttt aattaaccgg gcaactctct tcttcttaat cartgaaaat    60
ggcaagtctt ttacctcgtt tcaaaaagag ttaaatgcac tggaggtcct aaaggtttcg    120
```

<210> SEQ ID NO 45
<211> LENGTH: 132
<212> TYPE: DNA
<213> ORGANISM: Triticum aestivum

<400> SEQUENCE: 45

```
catgcggcgg gggccctgcg gcaatgatga ctccatgagg gtggyttcgg cggacgatgc    60
```

```
tctccgcagg ttgcactgga ctagcttggt gtgaggcttg caactttctc ctgtgatgct    120
catcaacaaa at                                                        132

<210> SEQ ID NO 46
<211> LENGTH: 61
<212> TYPE: DNA
<213> ORGANISM: Triticum aestivum

<400> SEQUENCE: 46
agtaattaca accttggcgg catttccaag racttctttg tctgctttgt ccagggacag     60
t                                                                     61

<210> SEQ ID NO 47
<211> LENGTH: 71
<212> TYPE: DNA
<213> ORGANISM: Triticum aestivum

<400> SEQUENCE: 47
cggtttatct gttatcattg tgcaccagga aaaccygact cctgagttca aaatatgtt      60 gattctataa a                                                          71

<210> SEQ ID NO 48
<211> LENGTH: 71
<212> TYPE: DNA
<213> ORGANISM: Triticum aestivum

<400> SEQUENCE: 48
ggcttaaggg agactctggt gacaccatgt aacttyacgg ccacgcacca cccgttggag     60
tttgacagtt c                                                          71

<210> SEQ ID NO 49
<211> LENGTH: 71
<212> TYPE: DNA
<213> ORGANISM: Triticum aestivum

<400> SEQUENCE: 49
ctcccctgcc aaacccaagt gtccctcctt gagtcrcaaa gttgtaccac agtggtggat     60
tgcaacagat t                                                          71

<210> SEQ ID NO 50
<211> LENGTH: 201
<212> TYPE: DNA
<213> ORGANISM: Triticum aestivum

<400> SEQUENCE: 50
actgggaact gcgctacacc ttctacgtgg ataatggcga ctkcgacgag ctamggggcg     60
tctggcacga tgacagtaat gggatgttgt gctactggct kggtgacgat ctctacaagt    120
atgacaccag taagaagggt caacaactga ccgccgatag tgtcttggag tgggaccatc    180 ggatcccccct gccggcaact a                                             201

<210> SEQ ID NO 51
<211> LENGTH: 201
<212> TYPE: DNA
<213> ORGANISM: Triticum aestivum

<400> SEQUENCE: 51
ctataaggaa agcatatcac tgtaaacagt atactatgac agaaacaaag agtacacagc     60
```

```
attttcccag gaatatataa tatatacttc atttactggt rgttgatgtg tagtcctaaa    120
cagaagatga aggctatgct ttcaatatca aaaagcgaaa ataaacagaa taaccagcat    180
agttgcagta attacaattt g                                              201

<210> SEQ ID NO 52
<211> LENGTH: 201
<212> TYPE: DNA
<213> ORGANISM: Triticum aestivum

<400> SEQUENCE: 52
taatttctat atacacacat acaacatgtg cacatacaat gcgtacgtgg caagcagatc    60
atgacaggtt ggcggacgcg gttctccgcc gcgggacgac rccagtgccg gcgcccttca   120
tctcggcccg aaatttggcg gagagtgcgt ttctcccggc tgcgggagcc gtgggccaaa   180
agaggcccat gctgacagcc a                                             201

<210> SEQ ID NO 53
<211> LENGTH: 200
<212> TYPE: DNA
<213> ORGANISM: Triticum aestivum

<400> SEQUENCE: 53
ttkatagtaa aaccaagcgt acagaattaa ttttagagca aacaaaatac tataatagaa    60
gtcaagcctt gacgcataag gtgaaagcct gaaccgacgm tagtaatcag taagcagatc   120
gtttctaaat aagatgatga atggtttatg ttttcccgct gttagaatat tgttcagcaa   180
acagcatagc taggactgtt                                                200

<210> SEQ ID NO 54
<211> LENGTH: 71
<212> TYPE: DNA
<213> ORGANISM: Triticum aestivum

<400> SEQUENCE: 54
gactacgcgt tcctcccggt ggtggcgctc taccckttgt gttgcctttc tccaagcagt    60
tgtgcccttc g                                                         71

<210> SEQ ID NO 55
<211> LENGTH: 71
<212> TYPE: DNA
<213> ORGANISM: Triticum aestivum

<400> SEQUENCE: 55
atatctttac aagtcatcga cttacatgct tctttktatt atatgcacct atgcagtact    60
tgttaatggg t                                                         71

<210> SEQ ID NO 56
<211> LENGTH: 71
<212> TYPE: DNA
<213> ORGANISM: Triticum aestivum

<400> SEQUENCE: 56
gatgatataa ccgtagccaa ggaagcccag attttsttct gtgtatctat aggagcttaa    60
ttaggaggag g                                                         71

<210> SEQ ID NO 57
<211> LENGTH: 71
<212> TYPE: DNA
<213> ORGANISM: Triticum aestivum
```

```
<400> SEQUENCE: 57
aagtctgcca tccagatcat tacccaacgg ccaatggagc catgaggttt gcctcgttgc      60
acgttttggc t                                                          71

<210> SEQ ID NO 58
<211> LENGTH: 71
<212> TYPE: DNA
<213> ORGANISM: Triticum aestivum

<400> SEQUENCE: 58
gcaacaaagc tggtcatcca aacatttaca tcgttaggca ggctttccgc ccaaaccatg      60
cggccgacct g                                                          71

<210> SEQ ID NO 59
<211> LENGTH: 71
<212> TYPE: DNA
<213> ORGANISM: Triticum aestivum

<400> SEQUENCE: 59
tatgtaaaac ctctttgttt ctaaatagct gcggctcgct acctaaattt atgttgaacc      60
tagaggcacc c                                                          71

<210> SEQ ID NO 60
<211> LENGTH: 71
<212> TYPE: DNA
<213> ORGANISM: Triticum aestivum

<400> SEQUENCE: 60
gttcggcaga atccaagtcg caaatgtaag gtcagcaaat gaatgatgat catgataatg      60
aaaatcataa g                                                          71

<210> SEQ ID NO 61
<211> LENGTH: 71
<212> TYPE: DNA
<213> ORGANISM: Triticum aestivum

<400> SEQUENCE: 61
acgtatggag cttcctcttt tcatcatgca ccattgtgat ctccctctta ttttgtctga     60
agccattcat g                                                          71

<210> SEQ ID NO 62
<211> LENGTH: 71
<212> TYPE: DNA
<213> ORGANISM: Triticum aestivum

<400> SEQUENCE: 62
aggtcatgaa aatgcaagtg gcgaatctta tctctgttat accatttggc aaaacaaagg     60
cgagagttct g                                                          71

<210> SEQ ID NO 63
<211> LENGTH: 76
<212> TYPE: DNA
<213> ORGANISM: Triticum aestivum

<400> SEQUENCE: 63
attgatgcgc tgtgcaaggc cagagctatg gacaaagcar agttgttcct ccggcagatg     60
attgataaag gtgttc                                                     76
```

<210> SEQ ID NO 64
<211> LENGTH: 780
<212> TYPE: PRT
<213> ORGANISM: Triticum aestivum

<400> SEQUENCE: 64

```
Met Pro Arg Phe Ser Ser Thr Thr Pro Met Ser Pro Arg Leu Leu
1               5                   10                  15

Leu Arg Leu Gly Ala Arg His Ser Ser Thr Ser His Pro Ser Arg
                20                  25                  30

Ile Trp Asp Pro His Ala Ala Phe Ala Ala Thr Gln Arg Ala Arg
                35                  40                  45

Ser Gly Thr Leu Thr Thr Glu Asp Ala His His Leu Phe Asp Glu Leu
    50                  55                  60

Leu Arg Gln Gly Asn Pro Val Gln Glu Arg Pro Leu Thr Asn Phe Leu
65                  70                  75                  80

Ala Ala Leu Ala Arg Ala Pro Ala Ser Ala Phe Cys Ser Asp Gly Pro
                85                  90                  95

Ala Leu Ala Val Ala Leu Phe Gly Arg Leu Ser Arg Gly Ala Gly Arg
                100                 105                 110

Arg Val Ala Gln Pro Asn Val Phe Thr Tyr Gly Val Leu Met Asp Cys
                115                 120                 125

Cys Cys Arg Ala Arg Arg Leu Asp Leu Ala Ile Ala Phe Phe Ala Arg
        130                 135                 140

Leu Leu Lys Thr Gly Leu Glu Ala Asn Gln Val Ile Phe Cys Thr Leu
145                 150                 155                 160

Leu Lys Gly Leu Cys His Ala Lys Arg Ser Asp Glu Ala Leu Asp Val
                165                 170                 175

Val Leu His Arg Met Pro Glu Leu Gly Cys Thr Pro Asn Val Val Ala
                180                 185                 190

Tyr Thr Thr Val Ile His Gly Phe Leu Lys Glu Gly Gln Val Gly Lys
                195                 200                 205

Ala Cys Asn Leu Phe His Gly Met Ala Gln Gln Gly Val Ala Pro Asp
        210                 215                 220

Val Val Thr Tyr Asn Ser Val Ile Asp Ala Leu Cys Lys Ala Arg Ala
225                 230                 235                 240

Met Asp Lys Ala Glu Tyr Phe Leu Arg Glu Met Val Asp Asn Gly Val
                245                 250                 255

Val Pro Asn Asn Val Thr Tyr Asn Ser Leu Ile His Gly Tyr Ser Ser
                260                 265                 270

Leu Gly His Gln Lys Glu Ala Val Arg Val Leu Lys Glu Met Thr Arg
        275                 280                 285

Gln Gly Ile Ile Pro Asp Val Ile Thr Cys Thr Ser Leu Met Thr Phe
        290                 295                 300

Leu Cys Lys Asn Gly Lys Ser Lys Glu Ala Ala Glu Ile Phe Asp Ser
305                 310                 315                 320

Met Ala Thr Lys Gly Leu Lys His Asp Ala Val Ser Tyr Ala Ile Leu
                325                 330                 335

Leu His Gly Tyr Ala Thr Glu Gly Cys Leu Val Asp Met Ile Asn Leu
                340                 345                 350

Phe Asn Ser Met Asp Arg Asp Cys Ile Leu Pro Asn Cys His Ile Phe
        355                 360                 365

Asn Ile Leu Ile Tyr Ala Tyr Ala Lys Ser Gly Lys Leu Asp Lys Ala
370                 375                 380
```

Met Leu Ile Phe Arg Asp Met Gln Lys Gln Gly Val Ser Pro Asp Ala
385                 390                 395                 400

Phe Thr Tyr Ser Thr Leu Ile His Ala Phe Cys Lys Lys Gly Arg Leu
            405                 410                 415

Asp Asp Ala Met Ile Lys Phe Asn Gln Met Val Asp Thr Gly Val Arg
        420                 425                 430

Gln Gly Thr Ala Val Tyr Gly Ser Leu Ile Gln Gly Phe Cys Thr His
        435                 440                 445

Gly Asp Leu Val Lys Gly Lys Glu Leu Val Thr Glu Met Met Asn Lys
    450                 455                 460

Gly Ile Pro Pro Asp Ile Met Phe Phe His Ser Ile Met Gln Asn
465                 470                 475                 480

Leu Cys Thr Glu Gly Arg Val Val Glu Ala Arg Asp Ile Leu Gly Leu
                485                 490                 495

Ile Ala His Ile Gly Met Arg Pro Asn Val Cys Thr Phe Asn Ile Leu
            500                 505                 510

Ile Gly Gly Tyr Cys Leu Val Arg Lys Met Glu Asp Ala Ser Lys Ile
        515                 520                 525

Phe His Asp Met Met Ser Tyr Gly Leu Glu Pro Ser Asn Val Thr Tyr
    530                 535                 540

Gly Ile Leu Ile Asn Gly Tyr Cys Lys Asn Arg Arg Ile Asp Asp Gly
545                 550                 555                 560

Leu Ile Leu Phe Lys Glu Met Leu Arg Lys Gly Leu Lys Pro Thr Thr
                565                 570                 575

Phe Asn Tyr Asn Ile Ile Leu Asp Gly Leu Phe Leu Ala Gly Arg Thr
            580                 585                 590

Val Ala Ala Lys Glu Lys Phe Asp Glu Met Val Glu Ser Gly Val Ser
        595                 600                 605

Met Cys Ile Ser Thr Tyr Ser Ile Val Leu Arg Gly Leu Cys Arg Asn
    610                 615                 620

Asn Cys Ser Gly Glu Ala Ile Thr Leu Phe Gln Thr Leu Ser Ala Met
625                 630                 635                 640

Asp Val Lys Phe Asn Ile Arg Ile Val Asn Ile Met Ile Asp Ala Phe
                645                 650                 655

Phe Arg Val Gln Arg Lys Gln Glu Ala Lys Asp Leu Phe Ala Ala Ile
            660                 665                 670

Thr Ala Asn Gly Leu Val Ala Asn Val Phe Thr Tyr Ser Leu Met Met
        675                 680                 685

Thr Asn Leu Ile Lys Glu Gly Ser Val Glu Glu Ala Asp Thr Leu Phe
    690                 695                 700

Leu Ser Met Glu Met Ser Gly Cys Thr Ser Asn Ser Trp Met Leu Asn
705                 710                 715                 720

Leu Ile Ile Arg Gly Leu Leu Glu Lys Gly Glu Ile Val Lys Ala Gly
                725                 730                 735

Cys Tyr Met Ser Lys Val Asp Ala Lys Ser Tyr Ser Leu Glu Ala Lys
            740                 745                 750

Thr Val Ser Leu Leu Ile Tyr Leu Phe Ser Gly Lys Gly Lys Tyr Arg
        755                 760                 765

Glu His Ile Arg Leu Leu Pro Thr Lys Tyr Gln Phe
    770                 775                 780

<210> SEQ ID NO 65
<211> LENGTH: 2376

<212> TYPE: DNA
<213> ORGANISM: Triticum aestivum

<400> SEQUENCE: 65

```
atgcctcgct tctcctccac cacgccaatg tcgccacccc gcctcctcct ccggctcggc      60
gcccgccact cctcctccac ctctcatccc tcacgcatct gggatcccca cgccgccttc     120
gccgctgcga cgcagcgggc gcgctctggc acgctcacca cggaggacgc acaccacctg     180
tttgatgaat gctgcggca gggcaatcct gtccaggagc gtcccttgac taactttctg     240
gctgccctcg cccgcgcgcc cgcgtccgca ttctgcagcg atggccctgc cctggccgtc     300
gccctcttcg gccgtttgtc ccgaggcgcc ggacgacggg tggcgcagcc aaatgtcttc     360
acctatggcg tcctcatgga ctgctgctgc cgtgcgcgcc gcctggatct agcgatcgcc     420
ttcttcgccc gtctcctcaa gacgggactg gaggcaaacc aagtcatctt ctgcacccto     480
ctcaagggac tctgccacgc aaagcgctca gatgaggctt tggacgtggt gcttcacagg     540
atgcctgagc taggctgcac ccccaacgtg gtggcctata ccacggtcat ccacggcttc     600
ttgaaggaag gccaagtagg caaggcatgc aatctattcc atggaatggc gcagcagggc     660
gttgcgcctg atgtggtgac atataactcg gttatcgatg cgttgtgcaa ggccagagca     720
atggacaagg cagagtattt ccttcgtgaa atggttgata atggtgtcgt acctaataat     780
gtgacatata atagcctcat ccatggatat tcctcttttgg gccatcagaa ggaggctgtt     840
agggtgctga agaaatgac aagacagggt atcataccag atgtcattac ctgcacctca     900
ctcatgacct tcctttgcaa gaatggaaaa agcaaggaag ctgcagaaat ttttgattca     960
atggccacga agggcctgaa acatgacgcc gtttcatatg ctattctcct tcatgggtat    1020
gccactgaag gatgcttggt tgatatgatt aatctcttca attcgatgga cagagactgt    1080
attctaccta actgtcatat cttcaacata ctgatttatg catatgctaa atctgggaag    1140
cttgataagg ctatgcttat atttagagat atgcagaaac aaggagtgag cccagatgca    1200
ttcacatatt caaccttaat acatgcattt tgtaaaaagg gtcggttgga cgatgctatg    1260
ataaagttta tcagatggt tgatacagga gtacgacagg gcacagctgt ttatggttct    1320
ctaatccagg gttttttgtac acacggcgat ttggtgaaag gaaaggaatt ggttactgaa    1380
atgatgaaca aaggtatacc tcctcctgac attatgttct tccattcaat catgcagaac    1440
ctatgcacag aaggaagggt agtagaagca cgggatatcc ttggcttgat agcacacata    1500
ggtatgaggc ctaatgtttg cacatttaat atactgattg gtggatactg cctagtccgc    1560
aagatggagg atgcctcaaa atatttcat gatatgatgt catatggttt agaaccttct    1620
aatgttacgt atggtattct tattaatggc tattgcaaaa acagaaggat tgatgacggg    1680
ctgattctgt tcaaagaaat gttgcgcaag ggacttaaac ctacaacttt taattacaac    1740
atcatactgg atggattatt tctggctgga cgaactgttg ctgcaaagga aaagtttgat    1800
gagatggttg aatctggagt aagtatgtgc atcagtactt actctatagt tcttcgtgga    1860
cttttgtagaa ataattgtag cggcgaagcc atcacgctat tccagacatt aagcgcaatg    1920
gatgtgaaat tcaatattag aattgtcaat atcatgattg atgccttctt cagggttcag    1980
cgaaagcaag aagctaagga tttgttgct gcaataacag ccaatgggtt ggttgctaat    2040
gttttttacct acagcctaat gatgacaaat cttataaaag aagggtcagt ggaagaggct    2100
gacacactct ttttatcgat ggagatgagc ggctgtactt cgaactcgtg gatgttaaat    2160
cttattatca gagggttgct ggaaaaagga gagatagtca aggctggatg ttatatgtct    2220
```

```
aaagttgatg cgaagagcta ctcacttgaa gctaaaactg tttcgttgct gatctatctc    2280
ttttcaggga aagggaaata cagagaacac ataagattgc tacctacaaa gtatcagttt    2340
ctcgaagaag cagccacagt tgaatggttt gctata                              2376

<210> SEQ ID NO 66
<211> LENGTH: 2376
<212> TYPE: DNA
<213> ORGANISM: Triticum aestivum

<400> SEQUENCE: 66
atgcctcgct ctccaccac cacgccaatg tcgccacccc gcctcctcct ccgactcggc      60
gcccgccact cctcctccac ctctcatccc tcacgcatct gggatcccca cgccgccttc    120
gccgctgcga cgcagcgggc gcgctctggc acgctcacca cggaggacgc acaccacctg    180
tttgatgaat tgctgcggca gggcaatcct gtccaggagc gtcccttgac taactttctg    240
gctgccctcg cccgcgcgcc cgcgtccgca ttctgcagcg atggccctgc cctggccgtc    300
gccctcttcg gccgtttgtc ccgaggcgcc ggacgacggg tggcgcagcc aaatgtcttc    360
acctatggcg tcctcatgga ctgctgctgc cgtgcgcgcc gcctggatct agcgatcgcc    420
ttcttcgccc gtcctcaa gacgggactg gaggcaaacc aagtcatctt ctgcaccctc      480
ctcaagggac tctgccacgc aaagcgctca gatgaggctt ggacgtggt gcttcacagg     540 atgcctgagc taggctgcac ccccaacgtg gtggcctata ccacggtcat ccacggcttc    600
ttgaaggaag gccaagtagg caaggcatgc aatctattcc atggaatggc gcagcagggc    660
gttgcgcctg atgtggtgac atataactcg gttatcgatg cgttgtgcaa ggccagagca    720
atggacaagg cagagtattt ccttcgtgaa atggttgata atggtgtcgt acctaataat    780
gtgacatata atagcctcat ccatggatat tcctctttgg gccatcagaa ggaggctgtt    840
agggtgctga agaaatgac aagacagggt atcataccag atgtcattac ctgcacctca    900
ctcatgacct ccctttgcaa gaatggaaaa agcaaggaag ctgcagaaat ttttgattca    960
atggccacga agggcctgaa acatgacgcc gtttcatatg ctattctcct tcatgggtat   1020
gccactgaag gatgcttggt tgatatgatt aatctcttca attcgatgga cagagactgt   1080
attctaccta actgtcatat cttcaacata ctgatttatg catatgctaa atctgggaag   1140
cttgataagg ctatgcttat atttagagat atgcagaaac aaggagtgag cccagatgca   1200
ttcacatatt caaccttaat acatgcattt tgtaaaaagg gtcggttgga cgatgctatg   1260
ataaagttta atcagatggt tgatacagga gtacgacagg gcacagctgt ttatggttct   1320
ctaatccagg gttttgtac acacggcgat ttggtgaaag gaaggaatt ggttactgaa     1380 atgatgaaca aggtatacc tcctcctgac attatgttct ccattcaat catgcagaac    1440 ctatgcacag aaggaagggt agtagaagca cgggatatcc ttggcttgat agcacacata   1500
ggtatgaggc ctaatgtttg cacatttaat atactgattg gtggatactg cctagtccgc   1560
aagatggagg atgcctcaaa atatttcat gatatgatgt catatggttt agaaccttct    1620
aatgttacgt atggtattct tattaatggc tattgcaaaa acagaaggat tgatgacggg   1680
ctgattctgt tcaaagaaat gttgcgcaag ggacttaaac ctacaacttt taattacaac   1740
atcatactgg atggattatt tctggctgga cgaactgttg ctgcaaagga aaagtttgat   1800
gagatggttg aatctggagt aagtatgtgc atcagtactt actctatagt tcttcgtgga   1860
ctttgtagaa ataattgtag cggcgaagcc atcacgctat tccagacatt aagcgcaatg   1920
gatgtgaaat tcaatattag aattgtcaat atcatgattg atgccttctt cagggttcag   1980
```

| | | |
|---|---|---|
| cgaaagcaag aagctaagga tttgtttgct gcaataacag ccaatgggtt ggttgctaat | 2040 |
| gtttttacct acagcctaat gatgacaaat cttataaaag aagggtcagt ggaagaggct | 2100 |
| gacacactct ttttatcgat ggagatgagc ggctgtactt cgaactcgtg gatgttaaat | 2160 |
| cttattatca gagggttgct ggaaaaagga gagatagtca aggctggatg ttatatgtct | 2220 |
| aaagttgatg cgaagagcta ctcacttgaa gctaaaactg tttcgttgct gatctatctc | 2280 |
| ttttcaggga aagggaaata cagagaacac ataagattgc tacctacaaa gtatcagttt | 2340 |
| ctcgaagaag cagccacagt tgaatggttt gctata | 2376 |

<210> SEQ ID NO 67
<211> LENGTH: 2376
<212> TYPE: DNA
<213> ORGANISM: Triticum aestivum

<400> SEQUENCE: 67

| | | |
|---|---|---|
| atgcctcgct tctcctccac cacgccaatg tcgccacccc gcctcctcct ccggctcggc | 60 |
| gcccgccact cctcctccac ctctcatccc tcacgcatct gggatcccca cgccgccttc | 120 |
| gccgctgcga cgcagcgggc gcgctctggc acgctcacca cggaggacgc acaccacctg | 180 |
| tttgatgaat tgctgcggca gggcaatcct gtccaggagc gtcccttgac taactttctg | 240 |
| gctgccctcg cccgcgcgcc cgcgtccgca ttctgcagcg atgggccctgc cctggccgtc | 300 |
| gccctcttcg gccgtttgtc ccgaggcgcc ggacgacggg tggcgcagcc aaatgtcttc | 360 |
| acctatggcg tcctcatgga ctgctgctgc cgtgcgcgcc gcctggatct agcgatcgcc | 420 |
| ttcttcgccc gtctcctcaa gacgggactg gaggcaaacc aagtcatctt ctgcaccctc | 480 |
| ctcaagggac tctgccacgc aaagcgctca gatgaggctt ggacgtggt gcttcacagg | 540 |
| atgcctgagc taggctgcac ccccaacgtg gtggcctata ccacggtcat ccacggcttc | 600 |
| ttgaaggaag gccaagtagg caaggcatgc aatctattcc atggaatggc gcagcagggc | 660 |
| gttgcgcctg atgtggtgac atataactcg gttatcgatg cgttgtgcaa ggccagagca | 720 |
| atggacaagg cagagtattt ccttcgtgaa atggttgata tggtgtcgt acctaataat | 780 |
| gtgacatata atagcctcat ccatggatat tcctcttttgg gccatcagaa ggaggctgtt | 840 |
| agggtgctga agaaaatgac aagacagggt atcataccag atgtcattac ctgcacctca | 900 |
| ctcatgacct tcctttgcaa gaatggaaaa agcaaggaag ctgcagaaat ttttgattca | 960 |
| atggccacga agggcctgaa acatgacgcc gtttcatatg ctattctcct tcatgggtat | 1020 |
| gccactgaag gatgcttggt tgatatgatt aatctcttca attcgatgga cagagactgt | 1080 |
| attctaccta actgtcatat cttcaacata ctgatttatg catatgctaa atctgggaag | 1140 |
| cttgataagg ctatgcttat atttagagat atgcagaaac aaggagtgag cccagatgca | 1200 |
| ttcacatatt caaccttaat acatgcattt tgtaaaaagg gtcggttgga cgatgctatg | 1260 |
| ataaagttta atcagatggt tgatacagga gtacgacagg gcacagctgt ttatggttct | 1320 |
| ctaatccagg gttttttgtac acacggcgat ttggtgaaag gaaaggaatt ggttactgaa | 1380 |
| atgatgaaca aaggtatacc tcctcctgac attatgttct tccattcaat catgcagaac | 1440 |
| ctatgcacag aaggaagggt agtagaagca cgggatatcc ttggcttgat agcacacata | 1500 |
| ggtatgaggc ctaatgtttg cacatttaat atactgattg gtggatactg cctagtccgc | 1560 |
| aagatggagg atgcctcaaa atatttcat gatatgatgt catatggttt agaaccttct | 1620 |
| aatgttacgt atggtattct tattaatggc tattgcaaaa acagaaggat tgatgacggg | 1680 |

| | |
|---|---|
| ctgattctgt tcaaagaaat gttgcgcaag ggacttaaac ctacaacttt taattacaac | 1740 |
| atcatactgg atggattatt tctggctgga cgaactgttg ctgcaaagga aaagtttgat | 1800 |
| gagatggttg aatctggagt aagtatgtgc atcagtactt actctatagt tcttcgtgga | 1860 |
| ctttgtagaa ataattgtag cggcgaagcc atcacgctat tccagacatt aagcgcaatg | 1920 |
| gatgtgaaat tcaatattag aattgtcaat atcatgattg atgccttctt cagggttcag | 1980 |
| cgaaagcaag aagctaagga tttgtttgct gcaataacag ccaatgggtt ggttgctaat | 2040 |
| gttttttacct acagcctaat gatgacaaat cttataaaag aagggtcagt ggaagaggct | 2100 |
| gacacactct ttttatcgat ggagatgagc ggctgtactt cgaactcgtg gatgttaaat | 2160 |
| cttattatca gagggttgct ggaaaaagga gagatagtca aggctggatg ttatatgtct | 2220 |
| aaagttgatg cgaagagcta ctcacttgaa gctaaaactg tttcgttgct gatctatctc | 2280 |
| ttttcaggga aagggaaata cagagaacac ataagattgc tacctacaaa gtatcagttt | 2340 |
| ctcgaagaag cagccacagt tgaatggttt gctata | 2376 |

<210> SEQ ID NO 68
<211> LENGTH: 2376
<212> TYPE: DNA
<213> ORGANISM: Triticum aestivum

<400> SEQUENCE: 68

| | |
|---|---|
| atgcctcgct ctccaccac cacgccaatg tcgccacccc gcctcctcct ccgactcggc | 60 |
| gcccgccact cctcctccac ctctcatccc tcacgcatct gggatcccca cgccgccttc | 120 |
| gccgctgcga cgcagcgggc gcgctctggc acgctcacca cggaggacgc acaccacctg | 180 |
| tttgatgaat tgctgcggca gggcaatcct gtccaggagc gtcccttgac taactttctg | 240 |
| gctgccctcg cccgcgcgcc cgcgtccgca ttctgcagcg atgggccctgc cctggccgtc | 300 |
| gccctcttcg gccgtttgtc ccgaggcgcc ggacgacggg tggcgcagcc aaatgtcttc | 360 |
| acctatggcg tcctcatgga ctgctgctgc cgtgcgcgcc gcctggatct agcgatcgcc | 420 |
| ttcttcgccc gtctcctcaa gacgggactg gaggcaaacc aagtcatctt ctgcaccctc | 480 |
| ctcaagggac tctgccacgc aaagcgctca gatgaggctt ggacgtggt gcttcacagg | 540 |
| atgcctgagc taggctgcac ccccaacgtg gtggcctata ccacggtcat ccacggcttc | 600 |
| ttgaaggaag gccaagtagg caaggcatgc aatctattcc atggaatggc gcagcagggc | 660 |
| gttgcgcctg atgtggtgac atataactcg gttatcgatg cgttgtgcaa ggccagagca | 720 |
| atggacaagg cagagtattt ccttcgtgaa atggttgata tggtgtcgt acctaataat | 780 |
| gtgacatata atagcctcat ccatggatat tcctcttttgg gccatcagaa ggaggctgtt | 840 |
| agggtgctga agaaatgac aagacagggt atcataccag atgtcattac ctgcaccctca | 900 |
| ctcatgacct tcctttgcaa gaatggaaaa agcaaggaag ctgcagaaat ttttgattca | 960 |
| atggccacga agggcctgaa acatgacgcc gtttcatatg ctattctcct tcatgggtat | 1020 |
| gccactgaag gatgcttggt tgatatgatt aatctcttca attcgatgga cagagactgt | 1080 |
| attctaccta actgtcatat cttcaacata ctgatttatg catatgctaa atctgggaag | 1140 |
| cttgataagg ctatgcttat atttagagat atgcagaaac aaggagtgag cccagatgca | 1200 |
| ttcacatatt caaccttaat acatgcattt tgtaaaaagg gtcggttgga cgatgctatg | 1260 |
| ataaagttta tcagatggt tgatacagga gtacgacagg gcacagctgt ttatggttct | 1320 |
| ctaatccagg gttttttgtac acacggcgat ttggtgaaaa gaaggaatt ggttactgaa | 1380 |
| atgatgaaca aaggtatacc tcctcctgac attatgttct tccattcaat catgcagaac | 1440 |

```
ctatgcacag aaggaagggt agtagaagca cgggatatcc ttggcttgat agcacacata    1500
ggtatgaggc ctaatgtttg cacatttaat atactgattg gtggatactg cctagtccgc    1560
aagatggagg atgcctcaaa aatatttcat gatatgatgt catatggttt agaaccttct    1620
aatgttacgt atggtattct tattaatggc tattgcaaaa acagaaggat tgatgacggg    1680
ctgattctgt tcaaagaaat gttgcgcaag ggacttaaac ctacaacttt taattacaac    1740
atcatactgg atggattatt tctggctgga cgaactgttg ctgcaaagga aaagtttgat    1800
gagatggttg aatctggagt aagtatgtgc atcagtactt actctatagt tcttcgtgga    1860
ctttgtagaa ataattgtag cggcgaagcc atcacgctat tccagacatt aagcgcaatg    1920
gatgtgaaat tcaatattag aattgtcaat atcatgattg atgccttctt cagggttcag    1980
cgaaagcaag aagctaagga tttgtttgct gcaataacag ccaatgggtt ggttgctaat    2040 gttttacct acagcctaat gatgacaaat cttataaaag aagggtcagt ggaagaggct    2100
gacacactct ttttatcgat ggagatgagc ggctgtactt cgaactcgtg gatgttaaat    2160
cttattatca gagggttgct ggaaaaagga gagatagtca aggctggatg ttatatgtct    2220
aaagttgatg cgaagagcta ctcacttgaa gctaaaactg tttcgttgct gatctatctc    2280
ttttcaggga aagggaaata cagagaacac ataagattgc tacctacaaa gtatcagttt    2340
ctcgaagaag cagccacagt tgaatggttt gctata                             2376

<210> SEQ ID NO 69
<211> LENGTH: 2379
<212> TYPE: DNA
<213> ORGANISM: Triticum aestivum

<400> SEQUENCE: 69
atgcctcgct tctcctccac cacgccaatg tcgccacccc gcctcctcct ccggctcggc      60
gcccgccact cctcctccac ctctcatccc tcacgcatct gggatcccca cgccgccttc     120
gccgctgcga cgcagcgggc gcgctctggc acgctcacca cggaggacgc acaccacctg     180
tttgatgaat tgctgcggca gggcaatcct gtccaggagc gtcccttgac taactttctg     240
gctgccctcg cccgcgcgcc cgcgtccgca ttctgcagcg atggccctgc cctggccgtc     300
gccctcttcg gccgttttgtc ccgaggcgcc ggacgacggg tggcgcagcc aaatgtcttc     360
acctatggcg tcctcatgga ctgctgctgc cgtgcgcgcc gctggatct agcgatcgcc     420 ttcttcgccc gtctcctcaa gacgggactg gaggcaaacc aagtcatctt ctgcaccctc     480
ctcaagggac tctgccacgc aaagcgctca gatgaggctt tggacgtggt gcttcacagg     540
atgcctgagc taggctgcac ccccaacgtg gtggcctata ccacggtcat ccacggcttc     600
ttgaaggaag gccaagtagg caaggcatgc aatctattcc atggaatggc gcagcagggc     660
gttgcgcctg atgtggtgac atataactcg gttatcgatg cgttgtgcaa ggccagagca     720
atggacaagg cagagtattt ccttcgtgaa atggttgata atggtgtcgt acctaataat     780
gtgacatata atagcctcat ccatggatat tcctcttttgg gccatcagaa ggaggctgtt     840
agggtgctga agaaaatgac aagacagggt atcataccag atgtcattac ctgcaccctca     900 ctcatgacct tcctttgcaa gaatggaaaa agcaaggaag ctgcagaaat ttttgattca     960
atggccacga agggcctgaa acatgacgcc gtttcatatg ctattctcct tcatgggtat    1020
gccactgaag gatgcttggt tgatatgatt aatctcttca attcgatgga cagagactgt    1080
attctaccta actgtcatat cttcaacata ctgatttatg catatgctaa atctgggaag    1140
```

```
cttgataagg ctatgcttat atttagagat atgcagaaac aaggagtgag cccagatgca    1200
ttcacatatt caaccttaat acatgcattt tgtaaaaagg gtcggttgga cgatgctatg    1260
ataaagttta atcagatggt tgatacagga gtacgacagg gcacagctgt ttatggttct    1320
ctaatccagg gttttgtac acacggcgat ttggtgaaag gaaaggaatt ggttactgaa      1380
atgatgaaca aaggtatacc tcctcctgac attatgttct tccattcaat catgcagaac    1440
ctatgcacag aaggaagggt agtagaagca cgggatatcc ttggcttgat agcacacata    1500
ggtatgaggc ctaatgtttg cacatttaat atactgattg gtggatactg cctagtccgc    1560
aagatggagg atgcctcaaa aatatttcat gatatgatgt catatggttt agaaccttct    1620
aatgttacgt atggtattct tattaatggc tattgcaaaa acagaaggat tgatgacggg    1680
ctgattctgt tcaaagaaat gttgcgcaag ggacttaaac ctacaacttt taattacaac    1740
atcatactgg atggattatt tctggctgga cgaactgttg ctgcaaagga aaagtttgat    1800
gagatggttg aatctggagt aagtatgtgc atcagtactt actctatagt tcttcgtgga    1860 cttttgtagaa ataattgtag cggcgaagcc atcacgctat tccagacatt aagcgcaatg    1920
gatgtgaaat tcaatattag aattgtcaat atcatgattg atgccttctt cagggttcag    1980
cgaaagcaag aagctaagga tttgtttgct gcaataacag ccaatgggtt ggttgctaat    2040 gttttttacct acagcctaat gatgacaaat cttataaaag aagggtcagt ggaagaggct    2100
gacacactct ttttatcgat ggagatgagc ggctgtactt cgaactcgtg gatgttaaat    2160
cttattatca gagggttgct ggaaaaagga gagatagtca aggctggatg ttatatgtct    2220
aaagttgatg ccaagagcta ctcacttgaa gctaaaactg tttcgttgct gatctatctc    2280
ttttcaggga aagggaaata cagagaacac ataagattgc tacctacaaa gtatcagttt    2340
ctcgaagaag cagccacagt tgaatggttt gctatatag                            2379
```

<210> SEQ ID NO 70
<211> LENGTH: 780
<212> TYPE: PRT
<213> ORGANISM: Triticum aestivum

<400> SEQUENCE: 70

```
Met Pro Arg Phe Ser Ser Thr Thr Pro Met Ser Pro Pro Arg Leu Arg
1               5                   10                  15

Leu Arg Leu Cys Ala Arg His Ser Ser Thr Ser His Pro Ser Arg
            20                  25                  30

Ile Trp Asp Pro His Ala Ala Phe Ala Ala Ala Gln Arg Ala Ser
        35                  40                  45

Ser Gly Thr Leu Thr Thr Glu Asp Ala His His Leu Phe Asp Glu Leu
    50                  55                  60

Leu Arg Arg Gly Asn Pro Val Gln Glu Arg Pro Leu Asn Lys Phe Leu
65                  70                  75                  80

Ala Ala Leu Ala Arg Ala Pro Ala Ser Ala Ser Cys Cys Asp Gly Pro
                85                  90                  95

Ala Leu Ala Val Ala Leu Phe Gly Arg Leu Ser Arg Asp Val Gly Arg
            100                 105                 110

Arg Val Ala Gln Pro Asn Val Phe Thr Tyr Gly Val Leu Met Asp Cys
        115                 120                 125

Cys Cys Arg Ala Cys Arg Thr Asp Leu Val Leu Ala Phe Phe Gly Arg
    130                 135                 140

Leu Leu Lys Thr Gly Leu Glu Ala Asn Gln Val Val Phe Asn Thr Leu
145                 150                 155                 160
```

-continued

Leu Lys Gly Leu Cys His Thr Lys Arg Ala Asp Glu Ala Leu Asp Val
            165                 170                 175

Leu Leu His Arg Met Pro Glu Leu Gly Cys Thr Pro Asn Val Val Ala
            180                 185                 190

Tyr Asn Thr Val Ile His Gly Phe Phe Lys Glu Gly His Val Ser Lys
            195                 200                 205

Ala Cys Asn Leu Phe His Glu Met Ala Gln Gln Gly Val Lys Pro Asn
            210                 215                 220

Val Val Thr Tyr Asn Ser Val Ile Asp Ala Leu Cys Lys Ala Arg Ala
225                 230                 235                 240

Met Asp Lys Ala Glu Val Val Leu Arg Gln Met Ile Asp Asp Gly Val
                245                 250                 255

Gly Pro Asp Asn Val Thr Tyr Ser Ser Leu Ile His Gly Tyr Ser Ser
                260                 265                 270

Ser Gly His Trp Lys Glu Ala Val Arg Val Phe Lys Glu Met Thr Ser
            275                 280                 285

Arg Arg Val Thr Ala Asp Val His Thr Tyr Asn Met Phe Met Thr Phe
            290                 295                 300

Leu Cys Lys His Gly Arg Ser Lys Glu Ala Ala Gly Ile Phe Asp Thr
305                 310                 315                 320

Met Ala Ile Lys Gly Leu Lys Pro Asp Asn Val Ser Tyr Ala Ile Leu
                325                 330                 335

Leu His Gly Tyr Ala Ala Glu Gly Cys Leu Val Asp Met Ile Asn Leu
            340                 345                 350

Phe Asn Ser Met Glu Arg Asp Cys Ile Leu Pro Asp Cys Arg Ile Phe
            355                 360                 365

Asn Ile Leu Ile Asn Ala Tyr Ala Lys Ser Gly Lys Leu Asp Lys Ala
            370                 375                 380

Met Leu Ile Phe Asn Glu Met Gln Lys Gln Gly Val Ser Pro Asn Ala
385                 390                 395                 400

Val Thr Tyr Ser Thr Val Ile His Ala Phe Cys Lys Lys Gly Arg Leu
                405                 410                 415

Asp Asp Ala Val Ile Lys Phe Asn Gln Met Ile Asp Thr Gly Val Arg
            420                 425                 430

Pro Asp Ala Ser Val Tyr Arg Pro Leu Ile Gln Gly Phe Cys Thr His
            435                 440                 445

Gly Asp Leu Val Lys Ala Lys Glu Tyr Val Thr Glu Met Met Lys Lys
            450                 455                 460

Gly Met Pro Pro Asp Ile Met Phe Phe Ser Ser Ile Met Gln Asn
465                 470                 475                 480

Leu Cys Thr Glu Gly Arg Val Thr Glu Ala Arg Asp Ile Leu Asp Leu
            485                 490                 495

Ile Val His Ile Gly Met Arg Pro Asn Val Ile Phe Asn Leu Leu
            500                 505                 510

Ile Gly Gly Tyr Cys Leu Val Arg Lys Met Ala Asp Ala Leu Lys Val
            515                 520                 525

Phe Asp Asp Met Val Ser Tyr Gly Leu Glu Pro Cys Asn Phe Thr Tyr
530                 535                 540

Gly Ile Leu Ile Asn Gly Tyr Cys Lys Asn Arg Arg Ile Asp Asp Gly
545                 550                 555                 560

Leu Ile Leu Phe Lys Glu Met Leu His Lys Gly Leu Lys Pro Thr Thr
            565                 570                 575

```
Phe Asn Tyr Asn Val Ile Leu Asp Gly Leu Phe Leu Ala Gly Gln Thr
            580                 585                 590

Val Ala Ala Lys Glu Lys Phe Asp Glu Met Val Glu Ser Gly Val Ser
        595                 600                 605

Val Cys Ile Asp Thr Tyr Ser Ile Ile Leu Gly Gly Leu Cys Arg Asn
    610                 615                 620

Ser Cys Ser Ser Glu Ala Ile Thr Leu Phe Arg Lys Leu Ser Ala Met
625                 630                 635                 640

Asn Val Lys Phe Asp Ile Thr Ile Val Asn Ile Ile Gly Ala Leu
                645                 650                 655

Tyr Arg Val Glu Arg Asn Gln Glu Ala Lys Asp Leu Phe Ala Ala Met
            660                 665                 670

Pro Ala Asn Gly Leu Val Pro Asn Ala Val Thr Tyr Thr Val Met Met
        675                 680                 685

Thr Asn Leu Ile Lys Glu Gly Ser Val Glu Glu Ala Asp Asn Leu Phe
    690                 695                 700

Leu Ser Met Glu Lys Ser Gly Cys Thr Ala Asn Ser Cys Leu Leu Asn
705                 710                 715                 720

His Ile Ile Arg Arg Leu Leu Glu Lys Gly Glu Ile Val Lys Ala Gly
                725                 730                 735

Asn Tyr Met Ser Lys Val Asp Ala Lys Ser Tyr Ser Leu Glu Ala Lys
            740                 745                 750

Thr Val Ser Leu Leu Ile Ser Leu Phe Ser Arg Lys Gly Lys Tyr Arg
        755                 760                 765

Glu His Ile Lys Leu Leu Pro Thr Lys Tyr Gln Phe
    770                 775                 780

<210> SEQ ID NO 71
<211> LENGTH: 391
<212> TYPE: PRT
<213> ORGANISM: Triticum aestivum

<400> SEQUENCE: 71

Met Pro Gly Phe Ser Ala Ala Ser Met Ser Pro Leu Arg Leu Arg
1               5                   10                  15

Leu Arg Leu His Ala Arg His Ser Ser Ala Ser Gln Pro Ser Arg Arg
                20                  25                  30

Gln Gly Trp Asp Pro His Ala Ala Phe Ala Ala Thr Glu Cys Ala
            35                  40                  45

Arg Ser Gly Asn Leu Thr Pro Glu Asp Ala His Asn Leu Phe Asp Glu
    50                  55                  60

Leu Leu Arg Gln Gly Asn Pro Val Leu Gly Arg Pro Leu Asn Asn Leu
65                  70                  75                  80

Leu Ala Ala Leu Ala Arg Ala Pro Ala Ser Ser Ala Cys Arg Asp Gly
                85                  90                  95

Pro Ala Leu Val Val Ala Leu Phe Ser Arg Ile Ser Gln Gly Ala Arg
            100                 105                 110

Leu Arg Val Leu His Pro Thr Ala Cys Thr Tyr Gly Ile Leu Met Asp
        115                 120                 125

Cys Ser Cys Arg Ala His Arg Leu Asp Leu Ala Phe Ala Phe Gly
130                 135                 140

Arg Leu Leu Arg Thr Gly Leu Lys Ala Gly Val Ile Glu Val Asn Ser
145                 150                 155                 160

Leu Leu Lys Gly Leu Cys His Ala Lys Arg Ala Asp Glu Ala Met Glu
                165                 170                 175
```

Val Leu Leu His Arg Met Pro Glu Leu Phe Ile Gly Val Gln Gly Thr
            180                 185                 190

Ala Val Tyr Arg Ser Leu Ile Gln Gly Phe Cys Thr His Gly Asp Leu
            195                 200                 205

Val Lys Ala Lys Glu Tyr Val Thr Glu Met Met Lys Lys Gly Met Pro
210                 215                 220

Pro Pro Asp Ile Met Phe Phe Ser Ser Ile Met Gln Asn Leu Cys Thr
225                 230                 235                 240

Glu Gly Arg Val Ile Glu Ala Arg Asp Ile Leu Asp Leu Ile Val Arg
                245                 250                 255

Ile Gly Met Arg Pro Asp Val Phe Ile Phe Asn Ile Leu Ile Gly Gly
            260                 265                 270

Tyr Cys Leu Val Gly Lys Met Glu Asp Ala Ser Lys Ile Phe Asp Asp
            275                 280                 285

Met Val Ser Tyr Gly Leu Glu Pro Cys Asn Phe Thr Tyr Gly Ile Leu
            290                 295                 300

Ile Asn Gly Tyr Cys Lys Asn Lys Arg Ile Asp Asp Gly Leu Ile Leu
305                 310                 315                 320

Phe Lys Glu Met Leu Arg Lys Gly Leu Lys Pro Thr Thr Phe Asn Tyr
                325                 330                 335

Asn Val Ile Leu Asp Gly Leu Phe Leu Ala Gly Gln Thr Val Ala Ala
            340                 345                 350

Lys Glu Lys Phe Asp Glu Met Val Glu Ser Gly Val Ser Val Cys Ile
            355                 360                 365

Asp Thr Tyr Ser Ile Val Leu Gly Gly Leu Cys Arg Asn Ser Cys Ser
            370                 375                 380

Ser Glu Ala Ile Thr Leu Phe
385                 390

<210> SEQ ID NO 72
<211> LENGTH: 542
<212> TYPE: PRT
<213> ORGANISM: Triticum aestivum

<400> SEQUENCE: 72

Met Pro Arg Leu Ser Ser Thr Thr Pro Met Ser Pro Arg Leu Arg
1               5                   10                  15

Leu Arg Leu Arg Gly Arg His Ser Ser Ser Thr Ser His Pro Ser Arg
                20                  25                  30

Ile Trp Asp Pro His Ala Ala Phe Ala Gly Ala Thr Gln Arg Ala His
            35                  40                  45

Ser Gly Asn Leu Thr Pro Glu Asp Ala His His Leu Phe Asp Glu Leu
        50                  55                  60

Leu Arg Gln Gly Asn Pro Val Gln Glu Arg Pro Leu Thr Asn Phe Leu
65                  70                  75                  80

Ala Ala Leu Ala Arg Ala Pro Ser Ala Ser Cys Ser Asp Gly Pro
                85                  90                  95

Ala Leu Ala Val Ala Leu Phe Gly Arg Leu Ser Arg Gly Ala Gly Arg
            100                 105                 110

Arg Val Ala Gln Pro Asn Val Phe Thr Tyr Gly Val Leu Met Asp Cys
            115                 120                 125

Cys Cys Arg Ala Cys Arg Pro Asp Leu Ala Leu Ala Phe Phe Gly Arg
        130                 135                 140

Leu Phe Arg Lys Gly Leu Glu Ala Asn Arg Val Ile Phe Cys Thr Leu

```
                145                 150                 155                 160
            Leu Lys Gly Leu Cys His Ala Lys Arg Thr Asp Glu Ala Leu Asp Val
                        165                 170                 175

Leu Leu His Arg Met Pro Glu Leu Gly Cys Thr Pro Asn Val Val Ala
                        180                 185                 190

Tyr Thr Thr Val Ile His Gly Phe Phe Lys Glu Gly Gln Val Gly Lys
                        195                 200                 205

Ala Cys Asn Leu Phe His Gly Met Ala Gln Gln Gly Val Ala Pro Asn
                210                 215                 220

Leu Val Thr Tyr Asn Ser Val Ile Asp Ala Leu Cys Lys Ala Lys Ala
            225                 230                 235                 240

Met Asp Lys Ala Glu Tyr Phe Leu Gly Gln Met Val Asp Asp Gly Val
                        245                 250                 255

Val Pro Asp Asn Val Thr Tyr Asn Ser Leu Ile His Gly Tyr Ser Ser
                        260                 265                 270

Ser Gly His Trp Lys Glu Ala Val Arg Val Phe Lys Glu Met Thr Ser
                        275                 280                 285

Arg Arg Val Thr Ala Asp Val His Thr Tyr Asn Met Phe Met Thr Phe
                290                 295                 300

Leu Cys Lys His Gly Arg Ser Lys Glu Ala Ala Gly Ile Phe Asp Thr
            305                 310                 315                 320

Met Ala Ile Lys Gly Leu Lys Pro Asp Asn Val Ser Tyr Ala Ile Leu
                        325                 330                 335

Leu His Gly Tyr Ala Thr Glu Gly Cys Leu Val Asp Met Ile Asn Leu
                        340                 345                 350

Phe Asn Ser Met Glu Arg Asp Cys Ile Leu Pro Asp Cys Arg Ile Phe
                        355                 360                 365

Asn Ile Leu Ile Asn Ala Tyr Ala Lys Ser Gly Lys Leu Asp Lys Ala
                370                 375                 380

Met Leu Ile Phe Asn Glu Met Gln Lys Gln Gly Val Ser Pro Asn Ala
            385                 390                 395                 400

Val Thr Tyr Ser Thr Val Ile His Thr Phe Cys Lys Lys Gly Arg Leu
                        405                 410                 415

Asp Asp Ala Val Ile Lys Phe Asn Gln Met Ile Asp Thr Gly Val Arg
                        420                 425                 430

Gln Gly Thr Ala Val Tyr Gly Ser Leu Ile Gln Gly Phe Cys Thr His
                        435                 440                 445

Gly Asp Leu Val Lys Ala Lys Glu Leu Leu Thr Glu Met Met Asn Lys
                450                 455                 460

Gly Met Leu Pro Pro Asp Ile Lys Phe Phe His Ser Ile Met Gln Asn
            465                 470                 475                 480

Leu Cys Thr Glu Gly Arg Val Ile Glu Ala Arg Asp Val Leu Gly Leu
                        485                 490                 495

Ile Ala His Ile Gly Met Arg Pro Asp Val Cys Thr Phe Asn Ile Leu
                        500                 505                 510

Ile Gly Gly Tyr Cys Leu Val Gly Lys Met Glu Asp Ala Ser Lys Ile
                        515                 520                 525

Phe Asp Asp Met Met Ser Tyr Gly Leu Glu Pro Ser Asn Cys
                530                 535                 540

<210> SEQ ID NO 73
<211> LENGTH: 2364
<212> TYPE: DNA
<213> ORGANISM: Triticum aestivum
```

<400> SEQUENCE: 73

```
atgccccgct tctcctccac cacgccaatg tcgccacccc gcctccgcct ccgactctgc      60
gcccgccact cctcctccac ctctcatccc tcacgcatct gggatcccca cgccgccttc     120
gccgccgcgg cacagcgggc gagctctggc acgctcacta cggaggacgc acaccacctg     180
tttgacgaat tgctgcggcg gggcaatcct gtccaggagc gtcccttgaa taaatttctg     240
gctgccctcg cccgcgcgcc ccgcgtccgca tcctgctgcg atggccccgc cctggcagtc     300
gccctcttcg gccgtttgtc ccgagacgtc ggacgacggg tggcgcagcc aaatgtcttc     360
acctatggcg tcctcatgga ctgctgctgc cgcgcttgcc gcacagatct ggtgctcgcc     420
ttctttggcc gtctcctcaa gacgggcctg gaggcaaacc aagtcgtctt caacaccctc     480
ctcaagggcc tttgccacac aaagcgggcg gatgaggctc tggacgtgct gcttcacagg     540
atgcctgagc tgggctgcac tcctaatgtg gtggcgtata acaccgttat ccatggcttc     600
tttaaggaag gccatgtaag caaggcctgc aatctgttcc atgaaatggc gcagcagggc     660
gttaagccta atgtggtgac atataactca gttatcgatg cgctgtgcaa ggccagagcc     720
atggacaagg cagaggtggt ccttcgtcag atgattgatg atggtgttgg acctgataat     780
gtgacgtata gtagcctcat ccatggatat tcctcttcag gccactggaa ggaggcagtt     840
agggtattca agagatgac aagtcggagg gttacagcag atgtgcatac ttacaacatg     900
tttatgacct ttcttttgcaa acatggaaga agcaaagaag ctgcaggaat ttttgatacc     960
atggctatca agggcctgaa acctgacaac gtttcatatg ctattctcct tcatgggtat    1020
gccgccgaag gatgcttagt tgatatgatt aatctcttca attcaatgga aagagattgt    1080
attctacctg actgtcgtat cttcaacata ctgattaatg catatgctaa atctgggaag    1140
cttgataagg ctatgcttat cttcaatgaa atgcagaaac aaggagtgag tccaaatgca    1200
gtcacatatt caaccgtaat acatgcattt tgcaagaagg gtaggttgga tgatgctgtg    1260
ataaagttta atcagatgat tgatacagga gtacgaccgg acgcatctgt ttatcgtccc    1320
ctaatccagg gttttttgtac acatggcgat ttggtgaaag caaggaaata tgttactgaa    1380
atgatgaaga aaggtatgcc tcctcctgat attatgttct tcagttcaat catgcagaac    1440
ctatgcacag aaggaagggt aacagaagca cgggatatcc ttgacttgat agtgcacatt    1500
ggtatgaggc ctaatgttat catatttaat ttgctgatcg gtggatactg cctagtccgc    1560
aagatggcag atgcattgaa agtatttgat gatatggtgt catatggttt agaaccttgt    1620
aactttacgt atggtatact tattaatggc tattgcaaaa atagaaggat tgatgacggg    1680
cttattctgt tcaaagagat gctgcacaag ggacttaaac ctacaacttt taattataac    1740
gtcatactgg atggattatt tctggctgga caaactgttg ctgcaaaaga gaagtttgat    1800
gagatggttg aatctggagt aagtgtgtgc attgatacat actctataat tcttggtgga    1860
ctttgtagaa atagctgcag tagcgaagcg atcacccttt ccggaaaatt aagcgcaatg    1920
aatgtgaaat ttgatattac aattgtcaat atcattattg gtgccttata cagggtcgag    1980
agaaaccaag aggctaagga tttgtttgct gctatgccag ccaatggctt ggttcctaat    2040
gctgttacct acaccgtaat gatgacaaat cttataaaag aaggttcagt ggaagaagct    2100
gacaatcttt tcttatccat ggagaagagc ggctgtactg ccaactcttg cctgttaaat    2160
catatcatca gaaggttact ggaaaaagga gagatagtca aggctggaaa ttatatgtct    2220
aaagttgatg caaagagcta ctcacttgaa gctaaaactg tttcgctgct gatctctctg    2280
```

| | |
|---|---:|
| ttttcaagga aagggaaata tagagaacac atcaaattgc ttcctacaaa gtatcagttt | 2340 |
| ctggaagaag cagccacagt tgaa | 2364 |

<210> SEQ ID NO 74
<211> LENGTH: 1173
<212> TYPE: DNA
<213> ORGANISM: Triticum aestivum

<400> SEQUENCE: 74

| | |
|---|---:|
| atgcctggct tctcctccgc cgcgtcaatg tcgccactgc gcctccgcct ccgcctgcac | 60 |
| gcccgccact cctccgcctc gcaaccctca cgccgccagg gatgggatcc ccacgccgcc | 120 |
| ttcgccgccg ccacggagtg tgcgcgctcc ggcaaccctca ccccggagga cgcacataac | 180 |
| ctgttcgacg aattgctgcg gcagggcaat cctgtccttg gcgcccccct caacaacctt | 240 |
| ctcgccgccc tcgcccgcgc gccggcgtcc agcgcctgca gagatggccc cgcactcgtg | 300 |
| gtcgccctct tcagccgcat atcccaaggc gcccgcctaa gggtgctgca cccaacggcc | 360 |
| tgcacctacg gcatcctcat ggactgcagc tgccgcgcac accgcctcga tctggcgttt | 420 |
| gccttcttcg gccgtctcct caggacggga ctgaaggcag gcgtcataga agtcaacagt | 480 |
| ctcctcaaag gactctgcca cgcaaagcgg gcggatgagg ccatggaagt gcttcttcac | 540 |
| aggatgcctg agctgtttat aggagtacag ggcacagctg tttatcgttc cctaatccag | 600 |
| ggattttgta cacacggcga tttggtgaaa gcaaaggaat atgttactga atgatgaag | 660 |
| aaaggtatgc ctcctcctga tattatgttc ttcagttcaa tcatgcagaa cctatgcaca | 720 |
| gaaggaaggg taatagaagc acgagatatc cttgacttga tagtgcgcat ggtatgagg | 780 |
| cctgatgttt tcatatttaa tatactgatc ggtggatact gcctagtcgg caagatggag | 840 |
| gatgcctcaa aaatatttga tgatatggtg tcatatggtt tagaaccttg taactttacg | 900 |
| tatggtatac ttattaatgg ctattgcaaa aataaaagga ttgatgacgg gcttattctg | 960 |
| ttcaaagaga tgctgcgcaa gggacttaaa cctacaactt ttaattataa cgtcatactg | 1020 |
| gatggattat ttctggctgg acaaactgtt gctgcaaaag agaagtttga tgagatggtt | 1080 |
| gaatctggag taagtgtgtg cattgataca tactctatag ttcttggtgg actttgtaga | 1140 |
| aatagctgca gtagcgaagc gatcaccctg ttc | 1173 |

<210> SEQ ID NO 75
<211> LENGTH: 1626
<212> TYPE: DNA
<213> ORGANISM: Triticum aestivum

<400> SEQUENCE: 75

| | |
|---|---:|
| atgcctcgcc tctcctccac cacgccaatg tcaccaccac gcctccgcct ccgactccgc | 60 |
| ggccgccact cctcctccac ctctcatccc tcacgcatct gggatcccca cgccgccttc | 120 |
| gccggcgcga cgcagcgggc gcactctggc aacctcaccc cggaggacgc acaccacctg | 180 |
| ttcgacgaat tgctgcggca gggcaatcct gtccaggagc gtcccttgac taactttctg | 240 |
| gctgccctcg cccgcgcgcc cgcgtccgca tcctgcagcg atggcccgc cctggccgta | 300 |
| gccctcttcg gtcgtttgtc ccgaggcgcc ggacgacgcg tggcacagcc aaatgtcttc | 360 |
| acctatggcg tcctcatgga ctgctgctgc cgcgcgtgcc gcccggatct ggcgctcgct | 420 |
| ttcttcggcc gtctcttcag gaagggcctg gaggcaaacc gagtcatctt ctgcaccctc | 480 |
| ctcaagggac tctgccacgc aaagcgcaca gatgaggctc tggacgtgct gcttcacagg | 540 |
| atgcctgagc tgggctgcac ccccaacgtg gtggcatata ccacggtcat ccacggcttc | 600 |

```
tttaaggaag gccaagtagg caaggcatgc aatctgttcc atggaatggc gcagcagggc    660
gttgcgccta atttggtgac atataactcg gttattgatg cgttgtgcaa ggccaaagca    720
atggacaagg cagagtattt ccttggtcag atggttgatg atggtgtcgt acctgataat    780
gtgacatata atagcctcat ccatggatat tcctcttcag gccactggaa ggaggcagtt    840
agggtattca agagatgac aagtcggagg gttacagcag atgtgcatac ttacaacatg     900
tttatgacct ttctttgcaa acatggaaga agcaaagaag ctgcaggaat ttttgatacc    960
atggctatta agggcctgaa acctgacaac gtttcatatg ctattctcct tcatgggtat    1020
gccaccgaag gatgcttagt tgatatgatt aatctcttca attcaatgga aagagattgt    1080
attctacctg actgtcgtat cttcaacata ctgattaatg catatgctaa atctgggaag    1140
cttgataagg ctatgcttat cttcaatgaa atgcagaaac aaggagtgag tccaaatgca    1200
gtcacatatt caaccgtaat acatacattt tgcaaaaagg gtaggttgga tgatgctgtg    1260
ataaagttta atcagatgat tgatacagga gtacgacagg gcacagctgt ttatggttct    1320
ctaatccagg ttttttgtac acacggcgat ttggtgaaag caaggaatt gcttactgaa     1380 atgatgaaca aaggtatgct tcctcctgat atcaagttct tccattcaat catgcagaac    1440 cttttgcacag aaggaagggt aatagaagca cgggatgtcc ttggcttgat agcgcacata   1500
ggtatgaggc ctgatgtttg cacatttaat atactgatcg gtggatactg cctagtcggc    1560
aagatggagg atgcctcaaa aatatttgat gatatgatgt catatggctt agaaccttct    1620
aattgt                                                               1626

<210> SEQ ID NO 76
<211> LENGTH: 2367
<212> TYPE: DNA
<213> ORGANISM: Triticum aestivum

<400> SEQUENCE: 76
atgccccgct tctcctccac cacgccaatg tcgccacccc gcctccgcct ccgactctgc     60
gcccgccact cctcctccac ctctcatccc tcacgcatct gggatcccca cgccgccttc    120
gccgccgcgg cacagcgggc gagctctggc acgctcacta cggaggacgc acaccacctg    180
tttgacgaat tgctgcggcg gggcaatcct gtccaggagc gtcccttgaa taaatttctg    240
gctgccctcg cccgcgcgcc ccgtccgca tcctgctgcg atggcccgcc ctggcagtc      300 gccctcttcg gccgtttgtc ccagacgtc ggacgacggg tggcgcagcc aaatgtcttc     360
acctatggcg tcctcatgga ctgctgctgc gcgcttgcc gcacagatct ggtgctcgcc     420
ttctttggcc gtctcctcaa gacgggcctg gaggcaaacc aagtcgtctt caacaccctc    480
ctcaagggcc tttgccacac aaagcgggcg gatgaggctc tggacgtgct gcttcacagg    540
atgcctgagc tgggctgcac tcctaatgtg gtggcgtata acaccgttat ccatggcttc    600
tttaaggaag gccatgtaag caaggcctgc aatctgttcc atgaaatggc gcagcagggc    660
gttaagccta atgtggtgac atataactca gttatcgatg cgctgtgcaa ggccagagcc    720
atggacaagg cagaggtggt ccttcgtcag atgattgatg atggtgttgg acctgataat    780
gtgacgtata gtagcctcat ccatggatat tcctcttcag gccactggaa ggaggcagtt    840
agggtattca agagatgac aagtcggagg gttacagcag atgtgcatac ttacaacatg     900
tttatgacct ttctttgcaa acatggaaga agcaaagaag ctgcaggaat ttttgatacc    960
atggctatca agggcctgaa acctgacaac gtttcatatg ctattctcct tcatgggtat    1020
```

```
gccgccgaag gatgcttagt tgatatgatt aatctcttca attcaatgga aagagattgt    1080
attctacctg actgtcgtat cttcaacata ctgattaatg catatgctaa atctgggaag    1140
cttgataagg ctatgcttat cttcaatgaa atgcagaaac aaggagtgag tccaaatgca    1200
gtcacatatt caaccgtaat acatgcattt tgcaagaagg gtaggttgga tgatgctgtg    1260
ataaagttta atcagatgat tgatacagga gtacgaccgg acgcatctgt ttatcgtccc    1320
ctaatccagg gttttttgtac acatggcgat ttggtgaaag caaggaata tgttactgaa    1380 atgatgaaga aaggtatgcc tcctcctgat attatgttct tcagttcaat catgcagaac    1440
ctatgcacag aaggaagggt aacagaagca cgggatatcc ttgacttgat agtgcacatt    1500
ggtatgaggc ctaatgttat catatttaat ttgctgatcg gtggatactg cctagtccgc    1560
aagatggcag atgcattgaa agtatttgat gatatggtgt catatggttt agaaccttgt    1620
aactttacgt atggtatact tattaatggc tattgcaaaa atagaaggat tgatgacggg    1680
cttattctgt tcaaagagat gctgcacaag ggacttaaac ctacaacttt taattataac    1740
gtcatactgg atggattatt tctggctgga caaactgttg ctgcaaaaga aagtttgat    1800 gagatggttg aatctggagt aagtgtgtgc attgatacat actctataat tcttggtgga    1860 cttttgtagaa atagctgcag tagcgaagcg atcacccttt tccggaaatt aagcgcaatg    1920
aatgtgaaat ttgatattac aattgtcaat atcattattg gtgccttata cagggtcgag    1980
agaaaccaag aggctaagga tttgtttgct gctatgccag ccaatggctt ggttcctaat    2040
gctgttacct acaccgtaat gatgacaaat cttataaaag aaggttcagt ggaagaagct    2100 gacaatctttt tcttatccat ggagaagagc ggctgtactg ccaactcttg cctgttaaat    2160
catatcatca gaaggttact ggaaaaagga gagatagtca aggctggaaa ttatatgtct    2220
aaagttgatg caaagagcta ctcacttgaa gctaaaactg tttcgctgct gatctctctg    2280
ttttcaagga agggaaata tagagaacac atcaaattgc ttcctacaaa gtatcagttt    2340
ctggaagaag cagccacagt tgaatag                                       2367

<210> SEQ ID NO 77
<211> LENGTH: 1176
<212> TYPE: DNA
<213> ORGANISM: Triticum aestivum

<400> SEQUENCE: 77
atgcctggct tctcctccgc cgcgtcaatg tcgccactgc gcctccgcct ccgcctgcac     60
gcccgccact cctccgcctc gcaaccctca cgccgccagg gatgggatcc ccacgccgcc    120
ttcgccgccg ccacggagtg tgcgcgctcc ggcaacctca ccccggagga cgcacataac    180
ctgttcgacg aattgctgcg gcagggcaat cctgtccttg ggcgcccct caacaacctt    240 ctcgccgccc tcgcccgcgc gccggcgtcc agcgcctgca gagatggccc cgcactcgtg    300
gtcgccctct tcagccgcat atcccaaggc gcccgcctaa gggtgctgca cccaacggcc    360
tgcacctacg gcatcctcat ggactgcagc tgccgcgcac accgcctcga tctggcgttt    420
gccttcttcg gccgtctcct caggacggga ctgaaggcag gcgtcataga agtcaacagt    480
ctcctcaaag gactctgcca cgcaaagcgg gcggatgagg ccatggaagt gcttcttcac    540
aggatgcctg agctgtttat aggagtacag ggcacagctg tttatcgttc cctaatccag    600 ggatttttgta cacacggcga tttggtgaaa gcaaaggaat atgttactga aatgatgaag    660
aaaggtatgc ctcctcctga tattatgttc ttcagttcaa tcatgcagaa cctatgcaca    720
gaaggaaggg taatagaagc acgagatatc cttgacttga tagtgcgcat tggtatgagg    780
```

```
cctgatgttt tcatatttaa tatactgatc ggtggatact gcctagtcgg caagatggag    840
gatgcctcaa aaatatttga tgatatggtg tcatatggtt tagaaccttg taactttacg    900
tatggtatac ttattaatgg ctattgcaaa ataaaagga ttgatgacgg cttattctg      960 ttcaaagaga tgctgcgcaa gggacttaaa cctacaactt ttaattataa cgtcatactg   1020
gatggattat ttctggctgg acaaactgtt gctgcaaaag agaagtttga tgagatggtt   1080
gaatctggag taagtgtgtg cattgataca tactctatag ttcttggtgg actttgtaga   1140
aatagctgca gtagcgaagc gatcaccctg ttctga                             1176
```

<210> SEQ ID NO 78
<211> LENGTH: 1629
<212> TYPE: DNA
<213> ORGANISM: Triticum aestivum

<400> SEQUENCE: 78

```
atgcctcgcc tctcctccac cacgccaatg tcaccaccac gcctccgcct ccgactccgc     60
ggccgccact cctcctccac ctctcatccc tcacgcatct gggatcccca cgccgccttc    120
gccggcgcga cgcagcgggc gcactctggc aacctcaccc cggaggacgc acaccacctg    180
ttcgacgaat tgctgcggca gggcaatcct gtccaggagc gtcccttgac taactttctg    240
gctgccctcg cccgcgcgcc cgcgtccgca tcctgcagcg atggcccgcc cctggccgta    300
gccctcttcg gtcgtttgtc ccgaggcgcc ggacgacgcg tggcacagcc aaatgtcttc    360
acctatggcg tcctcatgga ctgctgctgc cgcgcgtgcc gcccggatct ggcgctcgct    420
ttcttcggcc gtctcttcag gaagggcctg gaggcaaacc gagtcatctt ctgcaccctc    480
ctcaagggac tctgccacgc aaagcgcaca gatgaggctc tggacgtgct gcttcacagg    540
atgcctgagc tgggctgcac ccccaacgtg gtggcatata ccacggtcat ccacggcttc    600
tttaaggaag ccaagtaggc aaggcatgc aatctgttcc atggaatggc gcagcagggc    660
gttgcgccta atttggtgac atataactcg gttattgatg cgttgtgcaa ggccaaagca    720
atggacaagg cagagtattt ccttggtcag atggttgatg atggtgtcgt acctgataat    780
gtgacatata atagcctcat ccatggatat tcctcttcag gccactggaa ggaggcagtt    840
agggtattca aagagatgac aagtcggagg gttacagcag atgtgcatac ttacaacatg    900
tttatgacct ttctttgcaa acatggaaga agcaaagaag ctgcaggaat ttttgatacc    960
atggctatta agggcctgaa acctgacaac gtttcatatg ctattctcct tcatgggtat   1020
gccaccgaag gatgcttagt tgatatgatt aatctcttca attcaatgga aagagattgt   1080
attctacctg actgtcgtat cttcaacata ctgattaatg catatgctaa atctgggaag   1140
cttgataagg ctatgcttat cttcaatgaa atgcagaaac aaggagtgag tccaaatgca   1200
gtcacatatt caaccgtaat acatacattt tgcaaaaagg gtaggttgga tgatgctgtg   1260
ataaagttta atcagatgat tgatacagga gtacgacagg gcacagctgt ttatggttct   1320
ctaatccagg gttttttgtac acacggcgat ttggtgaaag caaggaatt gcttactgaa   1380 atgatgaaca aaggtatgct tcctcctgat atcaagttct tccattcaat catgcagaac   1440
ctttgcacag aaggaagggt aatagaagca cgggatgtcc ttggcttgat agcgcacata   1500
ggtatgaggc ctgatgtttg cacatttaat atactgatcg gtggatactg cctagtcggc   1560
aagatggagg atgcctcaaa aatatttgat gatatgatgt catatggctt agaaccttct   1620
aattgttag                                                          1629
```

<210> SEQ ID NO 79
<211> LENGTH: 780
<212> TYPE: PRT
<213> ORGANISM: Triticum aestivum

<400> SEQUENCE: 79

Met Pro Arg Phe Ser Ser Thr Met Pro Met Ser Pro His Leu Leu
1               5                   10                  15

Leu Arg Leu Cys Ala Arg His Ser Ser Thr Ser His Pro Ser Arg
                20                  25                  30

Ile Trp Asp Pro His Ala Ala Phe Ala Ala Ala Thr Gln Arg Ala Arg
            35                  40                  45

Ser Gly Thr Leu Thr Thr Glu Asp Ala His His Leu Phe Asp Glu Leu
    50                  55                  60

Leu Arg Gln Gly Asn Pro Val Gln Glu Arg Pro Leu Thr Asn Phe Leu
65                  70                  75                  80

Ala Ala Leu Ala Arg Ala Pro Ala Ser Ala Ser Cys Ser Asp Gly Pro
                85                  90                  95

Ala Leu Ala Val Ala Leu Phe Gly Arg Leu Ser Arg Gly Ala Gly Arg
                100                 105                 110

Arg Val Ala Gln Pro Asn Val Phe Thr Tyr Gly Val Leu Met Asp Cys
            115                 120                 125

Cys Cys Arg Ala Arg Arg Leu Asp Leu Ala Ile Ala Phe Phe Gly Arg
130                 135                 140

Leu Leu Lys Thr Gly Leu Glu Ala Asp Arg Val Val Phe Ser Thr Leu
145                 150                 155                 160

Leu Lys Gly Leu Cys His Ala Lys Arg Ser Asp Glu Ala Leu Asp Val
                165                 170                 175

Leu Leu His Arg Met Pro Glu Gln Gly Cys Thr Pro Tyr Val Val Ala
                180                 185                 190

Tyr Asn Thr Val Ile His Gly Phe Phe Arg Glu Gly Gln Val Gly Lys
            195                 200                 205

Ala Cys Asp Leu Phe His Gly Met Ala Gln Gln Gly Val Met Pro Asp
    210                 215                 220

Val Val Thr Tyr Asn Ser Val Ile Asp Ala Leu Cys Lys Ala Arg Ala
225                 230                 235                 240

Met Asp Lys Ala Glu Tyr Phe Leu Arg Gln Met Val Asp Asp Gly Val
                245                 250                 255

Val Pro Asn Asn Val Thr Tyr Asn Ser Leu Ile His Gly Tyr Ser Ser
                260                 265                 270

Ser Gly His Trp Lys Glu Ala Ile Arg Val Phe Lys Glu Met Thr Ser
            275                 280                 285

Arg Arg Ile Thr Ala Asp Val His Thr Tyr Asn Met Phe Met Thr Phe
    290                 295                 300

Leu Cys Lys His Gly Arg Ser Glu Glu Ala Ala Gly Ile Phe Asp Thr
305                 310                 315                 320

Met Ala Met Lys Gly Leu Lys Pro Asp Asn Val Ser Tyr Ala Ile Arg
                325                 330                 335

Leu His Gly Tyr Ala Thr Glu Gly Cys Leu Val Asp Met Ile Asn Leu
            340                 345                 350

Phe Asn Ser Met Glu Arg Asp Cys Ile Leu Pro Asp Cys Cys Ile Phe
        355                 360                 365

Asn Ile Leu Ile Asn Ala Tyr Ala Lys Ser Gly Lys Leu Asp Lys Ala
370                 375                 380

```
Met Leu Ile Phe Asn Glu Met Gln Lys Gln Gly Val Ser Pro Asp Ala
385                 390                 395                 400

Val Thr Tyr Leu Pro Val Ile Asp Ala Phe Cys Lys Lys Gly Arg Leu
            405                 410                 415

Asp Asp Ala Met Ile Met Phe Asn Gln Met Ile Asp Thr Gly Val Arg
            420                 425                 430

Pro Ala Thr Ala Val Tyr Thr Ser Leu Ile Gln Gly Phe Cys Thr His
            435                 440                 445

Gly Asp Leu Val Lys Ala Lys Glu Leu Val Thr Glu Met Met Asn Lys
            450                 455                 460

Gly Ile Pro Pro Asp Ile Lys Phe Phe His Ser Ile Met Gln Asn
465                 470                 475                 480

Leu Cys Thr Glu Gly Arg Val Thr Glu Ala Arg Asp Ile Leu Gly Leu
                485                 490                 495

Ile Ala His Ile Gly Met Arg Pro Asn Val Cys Thr Phe Asn Ile Leu
                500                 505                 510

Ile Gly Gly Tyr Cys Leu Val Arg Lys Met Thr Asp Ala Ser Lys Val
                515                 520                 525

Phe Asp Asp Met Val Ser Tyr Gly Leu Glu Pro Cys Asn Phe Thr Tyr
            530                 535                 540

Gly Ile Leu Ile Asn Gly Tyr Cys Lys Asn Arg Arg Ile Asp Asp Gly
545                 550                 555                 560

Leu Thr Leu Phe Lys Glu Met Leu His Lys Gly Leu Lys Pro Lys Ala
                565                 570                 575

Phe Asn Tyr Asn Val Ile Leu Asp Gly Leu Phe Leu Ala Gly Gln Thr
            580                 585                 590

Val Ala Ala Lys Glu Lys Phe Asp Glu Met Val Glu Ser Gly Val Ser
            595                 600                 605

Val Cys Ile Asp Thr Tyr Ser Ile Val Leu Gly Gly Leu Cys Arg Asn
            610                 615                 620

Ser Cys Ser Ser Glu Ala Ile Thr Leu Phe Arg Lys Leu Ser Ala Met
625                 630                 635                 640

Asn Val Lys Phe Asp Ile Thr Ile Val Asn Thr Ile Ile Gly Ala Phe
                645                 650                 655

Tyr Arg Val Glu Arg Asn Gln Glu Ala Lys Asp Leu Phe Ala Ala Ile
                660                 665                 670

Pro Ala Ser Gly Leu Val Pro Asn Val Thr Tyr Thr Ile Met Met
            675                 680                 685

Lys Asn Leu Ile Lys Glu Gly Ser Val Glu Glu Ala Asp Asn Leu Phe
            690                 695                 700

Leu Ser Met Glu Lys Ser Gly Cys Ser Ala Asn Ser Tyr Leu Leu Asn
705                 710                 715                 720

His Ile Ile Arg Arg Leu Leu Glu Lys Gly Glu Arg Val Lys Ala Gly
                725                 730                 735

Asn Tyr Met Ser Lys Val Asp Ala Lys Ser Tyr Ser Leu Glu Ala Lys
            740                 745                 750

Thr Val Ser Leu Leu Ile Ser Leu Phe Ser Arg Lys Gly Lys Tyr Arg
            755                 760                 765

Glu His Ile Lys Leu Leu Pro Thr Lys Tyr Gln Phe
770                 775                 780

<210> SEQ ID NO 80
<211> LENGTH: 628
```

<212> TYPE: PRT
<213> ORGANISM: Triticum aestivum

<400> SEQUENCE: 80

Met Asp Cys Cys Cys Arg Ala His Arg Leu Asp Leu Ala Phe Ala Phe
1               5                   10                  15

Phe Gly Arg Leu Leu Arg Thr Gly Leu Lys Ala Gly Val Ile Glu Val
            20                  25                  30

Asn Thr Leu Leu Lys Gly Leu Cys His Thr Lys Arg Ala Asp Glu Ala
        35                  40                  45

Met Glu Val Leu Leu His Arg Met Pro Glu Leu Gly Cys Thr Pro Asp
    50                  55                  60

Val Val Ala Tyr Thr Thr Val Ile His Gly Phe Phe Lys Glu Gly Gln
65                  70                  75                  80

Val Gly Lys Ala Cys Ser Leu Phe His Gly Met Ala Gln Gln Gly Val
                85                  90                  95

Ala Pro Asp Val Met Thr Tyr Ser Ser Val Ile Asp Ala Leu Cys Lys
            100                 105                 110

Ala Lys Ala Met Asp Lys Ala Glu Tyr Phe Leu Arg Gln Met Val Asp
        115                 120                 125

Asn Gly Val Val Pro Asp Asn Val Thr Tyr Asn Ser Leu Ile His Gly
    130                 135                 140

Tyr Ser Ser Gly His Trp Lys Glu Ala Val Arg Val Leu Lys Glu
145                 150                 155                 160

Met Thr Ser Gln Gly Ile Ile Pro Asp Ile Val Ser Tyr Arg Ile Leu
                165                 170                 175

Leu His Gly Tyr Ala Thr Glu Gly Cys Leu Val Asp Met Ile Asn Leu
            180                 185                 190

Phe Asn Ser Met Ala Arg Tyr Cys Ile Leu Pro Asp Cys His Ile Phe
        195                 200                 205

Asn Ile Leu Ile Asn Ala Tyr Ala Lys Ser Gly Lys Leu Asp Lys Ala
    210                 215                 220

Met Leu Ile Phe Arg Glu Met Gln Lys Gln Gly Val Ser Pro Asp Ala
225                 230                 235                 240

Val Thr Tyr Ser Thr Val Ile His Ala Phe Cys Lys Asn Gly Arg Leu
                245                 250                 255

Asp Asp Ala Val Ile Lys Phe Asn Gln Met Ile Asp Thr Gly Val Gln
            260                 265                 270

Pro Asn Thr Ser Val Tyr Asn Ala Leu Ile Gln Gly Phe Ser Thr Asn
        275                 280                 285

Gly Asp Leu Val Lys Ala Lys Glu Leu Val Thr Glu Met Met Asn Lys
    290                 295                 300

Gly Met His Pro Pro Asp Ile Lys Val Phe His Ser Val Met Gln Asn
305                 310                 315                 320

Leu Cys Thr Glu Gly Arg Val Thr Glu Ala Arg Asp Ile Leu Asp Leu
                325                 330                 335

Ile Val His Ile Gly Met Arg Pro Asp Val Phe Thr Phe Thr Leu Leu
            340                 345                 350

Ile Gly Gly Tyr Cys Leu Val Gly Lys Met Glu Asp Ala Ser Lys Ile
        355                 360                 365

Phe Asp Asp Met Met Ser Tyr Gly Leu Glu Pro Cys Asn Ile Thr Tyr
    370                 375                 380

Gly Ile Leu Ile Asn Gly Tyr Cys Lys Asn Arg Arg Ile Asp Asp Gly
385                 390                 395                 400

```
Leu Ile Leu Phe Lys Glu Met Leu His Lys Gly Leu Lys Pro Thr Thr
                405                 410                 415

Phe Asn Tyr Asn Val Ile Leu Asp Gly Leu Phe Leu Ala Gly Arg Thr
            420                 425                 430

Val Ala Ala Lys Glu Lys Phe Asp Glu Met Val Glu Ser Gly Val Ser
        435                 440                 445

Val Cys Ile Asp Thr Tyr Ser Ile Val Leu Gly Gly Leu Cys Arg Asn
    450                 455                 460

Asn Cys Ser Gly Glu Ala Ile Thr Leu Phe Gln Lys Leu Ser Lys Met
465                 470                 475                 480

Asn Val Lys Phe Asn Ile Arg Ile Val Asn Phe Met Ile Asp Ala Phe
                485                 490                 495

Phe Arg Val Gln Arg Lys Gln Glu Ala Glu Asp Leu Phe Ala Ala Ile
            500                 505                 510

Ser Ala Asn Gly Leu Val Ala Asn Val Phe Thr Tyr Ser Leu Met Met
        515                 520                 525

Thr Asn Leu Ile Lys Glu Gly Ser Ala Glu Lys Ala Asp Thr Leu Phe
    530                 535                 540

Leu Ser Met Glu Lys Ser Gly Cys Thr Ala Asn Ser Trp Met Leu Asn
545                 550                 555                 560

Leu Ile Ile Arg Arg Leu Leu Glu Lys Gly Glu Ile Val Lys Ala Gly
                565                 570                 575

Asn Tyr Met Ala Lys Val Asp Ala Lys Ser Tyr Ser Leu Glu Ala Lys
            580                 585                 590

Thr Val Ser Leu Leu Ile Ser Leu Phe Ser Gly Lys Gly Lys Tyr Arg
        595                 600                 605

Glu His Ile Arg Leu Leu Pro Thr Lys Tyr Gln Phe Arg Glu Glu Ala
    610                 615                 620

Ala Thr Val Glu
625

<210> SEQ ID NO 81
<211> LENGTH: 490
<212> TYPE: PRT
<213> ORGANISM: Triticum aestivum
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid

<400> SEQUENCE: 81

Met Trp Trp Arg Ile Ala Arg Ser Ser Met Ala Phe Leu Arg Arg Val
1               5                   10                  15

Lys Gln Gly Arg His Ala Val Tyr Ser Met Thr Ala Lys Gly Gln Lys
            20                  25                  30

Pro Asp Ile Ile Ser Tyr Cys Thr Leu Leu His Gly Xaa Ala Xaa Glu
        35                  40                  45

Gly Cys Phe Xaa Asp Met Ile Asp Leu Phe Asn Ser Met Lys Ser Asn
    50                  55                  60

Gly Ile Ala Ala Asp Cys Arg Val Phe Thr Ile Leu Ile Asp Ala Tyr
```

-continued

```
                65                  70                  75                  80
            Ala Lys Arg Gly Met Met Asp Ala Met His Ile Phe Thr Glu Met
                            85                  90                  95
            Trp Glu Lys Gly Val Ser Pro Asp Val Val Thr Tyr Ser Thr Val Ile
                           100                 105                 110
            Ala Ala Leu Ser Arg Met Gly Arg Leu Thr Asp Ala Met Asp Lys Phe
                           115                 120                 125
            Asn Gln Met Ile Ser Met Gly Val Gln Pro Asn Thr Val Val Tyr His
                           130                 135                 140
            Thr Leu Ile Gln Gly Ser Cys Met His Gly Asp Leu Ile Lys Ala Lys
            145                 150                 155                 160
            Glu Leu Val Ser Glu Met Met Asn Lys Gly Ile Pro Arg Pro Ser Ile
                           165                 170                 175
            Ala Phe Phe Gly Ser Ile Ile Asn Arg Leu Cys Lys Asp Gly Arg Val
                           180                 185                 190
            Met Asp Ala His Asp Ile Phe Asp Leu Val Ile Asp Ile Gly Glu Arg
                           195                 200                 205
            Pro Ser Val Ile Thr Phe Asn Ser Leu Val Asp Gly Tyr Cys Leu Val
                           210                 215                 220
            Gly Lys Met Asp Lys Ala Phe Gly Met Leu Asn Ala Met Glu Ser Val
            225                 230                 235                 240
            Gly Val Glu Pro Asp Ile Val Thr Tyr Ser Thr Leu Leu Asp Gly Tyr
                           245                 250                 255
            Phe Lys Asn Gly Arg Ile Asn Asp Gly Leu Thr Leu Phe Arg Glu Met
                           260                 265                 270
            Pro Leu Lys Arg Ile Lys Pro Asp Thr Val Thr Tyr Gly Ile Met Leu
                           275                 280                 285
            Asp Gly Cys Phe Arg Ala Gly Arg Thr Val Ala Ala Arg Thr Met Phe
                           290                 295                 300
            His Glu Met Ile Glu Ser Gly Ile Thr Val Asp Ile Pro Thr Tyr Asn
            305                 310                 315                 320
            Ile Val Leu Arg Gly Leu Cys Arg Asn Asn Cys Thr Asp Glu Ala Ile
                           325                 330                 335
            Ala Leu Phe Gln Lys Leu Gly Ala Met Ser Met Lys Phe Asn Ile Ala
                           340                 345                 350
            Ile Leu Asn Thr Met Ile Asn Ala Ile Tyr Lys Val Arg Arg Arg Glu
                           355                 360                 365
            Glu Ala Asn Asn Leu Phe Ala Ala Ile Ser Ala Ser Gly Leu Val Pro
                           370                 375                 380
            Asn Gln Ser Thr Tyr Ala Val Met Ile Ile Asn Leu Leu Lys Asp Gly
            385                 390                 395                 400
            Ala Val Glu His Ala Ser Asn Met Phe Ser Ser Met Glu Lys Ser Gly
                           405                 410                 415
            Ile Val Pro Ser Ser Arg Leu Ile Asn Gly Ile Ile Arg Leu Leu Leu
                           420                 425                 430
            Glu Asn Gly Glu Ile Ala Lys Ala Gly Ile Tyr Leu Ser Lys Val Asp
                           435                 440                 445
            Gly Asn Ser Ile Ser Leu Glu Ala Ser Thr Thr Ser Leu Met Leu Ser
                           450                 455                 460
            Leu Phe Ser Arg Lys Gly Lys Tyr Gln Glu Asp Met Lys Leu Leu Pro
            465                 470                 475                 480
            Ala Lys Tyr Gln Phe Phe Gly Glu Phe Gly
                           485                 490
```

<210> SEQ ID NO 82
<211> LENGTH: 46
<212> TYPE: DNA
<213> ORGANISM: Triticum aestivum

<400> SEQUENCE: 82
gaaggtgacc aagttcatgc tggtgaacaa aacaggccta caatca            46

<210> SEQ ID NO 83
<211> LENGTH: 46
<212> TYPE: DNA
<213> ORGANISM: Triticum aestivum

<400> SEQUENCE: 83
gaaggtgacc aagttcatgc tgtactatgg ctatgtctct gaatgc            46

<210> SEQ ID NO 84
<211> LENGTH: 48
<212> TYPE: DNA
<213> ORGANISM: Triticum aestivum

<400> SEQUENCE: 84
gaaggtgacc aagttcatgc tagtagaata ccacccaata aatcactg          48

<210> SEQ ID NO 85
<211> LENGTH: 43
<212> TYPE: DNA
<213> ORGANISM: Triticum aestivum

<400> SEQUENCE: 85
gaaggtgacc aagttcatgc tatctagcca cgcaaatgcc cgt               43

<210> SEQ ID NO 86
<211> LENGTH: 44
<212> TYPE: DNA
<213> ORGANISM: Triticum aestivum

<400> SEQUENCE: 86
gaaggtgacc aagttcatgc tgtcgmaccc aatgaataat gttt              44

<210> SEQ ID NO 87
<211> LENGTH: 45
<212> TYPE: DNA
<213> ORGANISM: Triticum aestivum

<400> SEQUENCE: 87
gaaggtgacc aagttcatgc tgttccttgt gacatgtact cataa             45

<210> SEQ ID NO 88
<211> LENGTH: 49
<212> TYPE: DNA
<213> ORGANISM: Triticum aestivum

<400> SEQUENCE: 88
gaaggtgacc aagttcatgc taacaacaat taygaggatc aaatggtca         49

<210> SEQ ID NO 89
<211> LENGTH: 41
<212> TYPE: DNA
<213> ORGANISM: Triticum aestivum

<400> SEQUENCE: 89

```
gaaggtgacc aagttcatgc tggttcctga gagagcaacc a                 41
```

<210> SEQ ID NO 90
<211> LENGTH: 54
<212> TYPE: DNA
<213> ORGANISM: Triticum aestivum

<400> SEQUENCE: 90

```
gaaggtgacc aagttcatgc tcaaattact tttgttcttt tatttttttc gaat    54
```

<210> SEQ ID NO 91
<211> LENGTH: 53
<212> TYPE: DNA
<213> ORGANISM: Triticum aestivum

<400> SEQUENCE: 91

```
gaaggtgacc aagttcatgc taaaaacatc tattccaagc aagtattagt aat     53
```

<210> SEQ ID NO 92
<211> LENGTH: 47
<212> TYPE: DNA
<213> ORGANISM: Triticum aestivum

<400> SEQUENCE: 92

```
gaaggtgacc aagttcatgc ttcagctgca taaaaamcag aatacca            47
```

<210> SEQ ID NO 93
<211> LENGTH: 48
<212> TYPE: DNA
<213> ORGANISM: Triticum aestivum

<400> SEQUENCE: 93

```
gaaggtgacc aagttcatgc taattgttca caacatggac atgagaac           48
```

<210> SEQ ID NO 94
<211> LENGTH: 47
<212> TYPE: DNA
<213> ORGANISM: Triticum aestivum

<400> SEQUENCE: 94

```
gaaggtgacc aagttcatgc ttcagctgca taaaaamcag aatacca            47
```

<210> SEQ ID NO 95
<211> LENGTH: 51
<212> TYPE: DNA
<213> ORGANISM: Triticum aestivum

<400> SEQUENCE: 95

```
gaaggtgacc aagttcatgc tattgtttcc atgttaagct tatattgtgc a       51
```

<210> SEQ ID NO 96
<211> LENGTH: 46
<212> TYPE: DNA
<213> ORGANISM: Triticum aestivum

<400> SEQUENCE: 96

```
gaaggtgacc aagttcatgc tgaatctgat taagacgctg gagaac             46
```

<210> SEQ ID NO 97
<211> LENGTH: 50
<212> TYPE: DNA
<213> ORGANISM: Triticum aestivum

<400> SEQUENCE: 97

-continued gaaggtgacc aagttcatgc taagcttgat aaggctatgc ttatatttag            50

<210> SEQ ID NO 98
<211> LENGTH: 46
<212> TYPE: DNA
<213> ORGANISM: Triticum aestivum

<400> SEQUENCE: 98
gaaggtgacc aagttcatgc tgttaatgct gtagccattc ttgcaa                46

<210> SEQ ID NO 99
<211> LENGTH: 44
<212> TYPE: DNA
<213> ORGANISM: Triticum aestivum

<400> SEQUENCE: 99
gaaggtgacc aagttcatgc tcattcgacg cgtcttccgc aata                  44

<210> SEQ ID NO 100
<211> LENGTH: 50
<212> TYPE: DNA
<213> ORGANISM: Triticum aestivum

<400> SEQUENCE: 100
gaaggtgacc aagttcatgc tgattcaaag aggtgacaaa tatgtgtact            50

<210> SEQ ID NO 101
<211> LENGTH: 39
<212> TYPE: DNA
<213> ORGANISM: Triticum aestivum

<400> SEQUENCE: 101
gaaggtgacc aagttcatgc tcctgagctg ggctgcacc                        39

<210> SEQ ID NO 102
<211> LENGTH: 42
<212> TYPE: DNA
<213> ORGANISM: Triticum aestivum

<400> SEQUENCE: 102
gaaggtgacc aagttcatgc tcctggagat ggatccggtc ag                    42

<210> SEQ ID NO 103
<211> LENGTH: 46
<212> TYPE: DNA
<213> ORGANISM: Triticum aestivum

<400> SEQUENCE: 103
gaaggtgacc aagttcatgc tagaatcgtt cttcgagaag cactca                46

<210> SEQ ID NO 104
<211> LENGTH: 45
<212> TYPE: DNA
<213> ORGANISM: Triticum aestivum

<400> SEQUENCE: 104
gaaggtgacc aagttcatgc tacggaatcg agtcaaccaa ttcct                 45

<210> SEQ ID NO 105
<211> LENGTH: 45
<212> TYPE: DNA
<213> ORGANISM: Triticum aestivum

<400> SEQUENCE: 105
gaaggtgacc aagttcatgc tgccttttct tcttccagca tctac          45

<210> SEQ ID NO 106
<211> LENGTH: 54
<212> TYPE: DNA
<213> ORGANISM: Triticum aestivum

<400> SEQUENCE: 106
gaaggtgacc aagttcatgc tatattgttt gtattaaaaa gttgtgtgtt ttga    54

<210> SEQ ID NO 107
<211> LENGTH: 45
<212> TYPE: DNA
<213> ORGANISM: Triticum aestivum

<400> SEQUENCE: 107
gaaggtgacc aagttcatgc tgttgccctg cgcaaaatca aactt          45

<210> SEQ ID NO 108
<211> LENGTH: 44
<212> TYPE: DNA
<213> ORGANISM: Triticum aestivum

<400> SEQUENCE: 108
gaaggtgacc aagttcatgc taaagggcta tcctggtgaa caac           44

<210> SEQ ID NO 109
<211> LENGTH: 51
<212> TYPE: DNA
<213> ORGANISM: Triticum aestivum

<400> SEQUENCE: 109
gaaggtgacc aagttcatgc taaatgccta gtctatacct gataaactaa a    51

<210> SEQ ID NO 110
<211> LENGTH: 40
<212> TYPE: DNA
<213> ORGANISM: Triticum aestivum

<400> SEQUENCE: 110
gaaggtgacc aagttcatgc tcgtccccca tggcacctgt              40

<210> SEQ ID NO 111
<211> LENGTH: 53
<212> TYPE: DNA
<213> ORGANISM: Triticum aestivum

<400> SEQUENCE: 111
gaaggtgacc aagttcatgc ttaatttggt taaccaaatc cttttgatt ttt    53

<210> SEQ ID NO 112
<211> LENGTH: 44
<212> TYPE: DNA
<213> ORGANISM: Triticum aestivum

<400> SEQUENCE: 112
gaaggtgacc aagttcatgc tggattttct caccggcatc tcca           44

<210> SEQ ID NO 113
<211> LENGTH: 47
<212> TYPE: DNA
<213> ORGANISM: Triticum aestivum

```
<400> SEQUENCE: 113
gaaggtgacc aagttcatgc ttcccatgtt cttttttgc tcaaaac         47

<210> SEQ ID NO 114
<211> LENGTH: 45
<212> TYPE: DNA
<213> ORGANISM: Triticum aestivum

<400> SEQUENCE: 114
gaaggtgacc aagttcatgc tactgggtgc aaagccaaga tgatt         45

<210> SEQ ID NO 115
<211> LENGTH: 46
<212> TYPE: DNA
<213> ORGANISM: Triticum aestivum

<400> SEQUENCE: 115
gaaggtgacc aagttcatgc taaagagcat gtcagacaca atgcag        46

<210> SEQ ID NO 116
<211> LENGTH: 44
<212> TYPE: DNA
<213> ORGANISM: Triticum aestivum

<400> SEQUENCE: 116
gaaggtgacc aagttcatgc tggcgaaact tcgccgcgat aaat          44

<210> SEQ ID NO 117
<211> LENGTH: 48
<212> TYPE: DNA
<213> ORGANISM: Triticum aestivum

<400> SEQUENCE: 117
gaaggtgacc aagttcatgc tcaagttgct cttaattatc tgtgcgta      48

<210> SEQ ID NO 118
<211> LENGTH: 53
<212> TYPE: DNA
<213> ORGANISM: Triticum aestivum

<400> SEQUENCE: 118
gaaggtgacc aagttcatgc tatagcaagt agagttaact tatcaagtta tta    53

<210> SEQ ID NO 119
<211> LENGTH: 44
<212> TYPE: DNA
<213> ORGANISM: Triticum aestivum

<400> SEQUENCE: 119
gaaggtgacc aagttcatgc tgacatctga tgagccagca taca          44

<210> SEQ ID NO 120
<211> LENGTH: 42
<212> TYPE: DNA
<213> ORGANISM: Triticum aestivum

<400> SEQUENCE: 120
gaaggtgacc aagttcatgc tacctcctcc gtatctgatg gc            42

<210> SEQ ID NO 121
<211> LENGTH: 48
<212> TYPE: DNA
```

<213> ORGANISM: Triticum aestivum

<400> SEQUENCE: 121
gaaggtgacc aagttcatgc tatctactca tctattgcag atgctctt    48

<210> SEQ ID NO 122
<211> LENGTH: 47
<212> TYPE: DNA
<213> ORGANISM: Triticum aestivum

<400> SEQUENCE: 122
gaaggtgacc aagttcatgc tgatgacatg gaggattata tcgacga    47

<210> SEQ ID NO 123
<211> LENGTH: 44
<212> TYPE: DNA
<213> ORGANISM: Triticum aestivum

<400> SEQUENCE: 123
gaaggtgacc aagttcatgc tggtcgtagc acatagccgt ttac    44

<210> SEQ ID NO 124
<211> LENGTH: 49
<212> TYPE: DNA
<213> ORGANISM: Triticum aestivum

<400> SEQUENCE: 124
gaaggtgacc aagttcatgc tggcttcttt tttctcccta taatatgga    49

<210> SEQ ID NO 125
<211> LENGTH: 47
<212> TYPE: DNA
<213> ORGANISM: Triticum aestivum

<400> SEQUENCE: 125
gaaggtgacc aagttcatgc tcgggcaact ctcttcttct taatcaa    47

<210> SEQ ID NO 126
<211> LENGTH: 43
<212> TYPE: DNA
<213> ORGANISM: Triticum aestivum

<400> SEQUENCE: 126
gaaggtgacc aagttcatgc tatgatgact ccatgagggt ggc    43

<210> SEQ ID NO 127
<211> LENGTH: 39
<212> TYPE: DNA
<213> ORGANISM: Triticum aestivum

<400> SEQUENCE: 127
gaaggtgacc aagttcatgc tgtggtggcg ctctacccg    39

<210> SEQ ID NO 128
<211> LENGTH: 47
<212> TYPE: DNA
<213> ORGANISM: Triticum aestivum

<400> SEQUENCE: 128
gaaggtgacc aagttcatgc taagtcatcg acttacatgc ttctttg    47

<210> SEQ ID NO 129
<211> LENGTH: 43

```
<212> TYPE: DNA
<213> ORGANISM: Triticum aestivum

<400> SEQUENCE: 129
gaaggtgacc aagttcatgc tagccaagga agcccagatt ttc                    43

<210> SEQ ID NO 130
<211> LENGTH: 44
<212> TYPE: DNA
<213> ORGANISM: Triticum aestivum

<400> SEQUENCE: 130
gaaggtgacc aagttcatgc tagatcatta cccaacggcc aatg                   44

<210> SEQ ID NO 131
<211> LENGTH: 46
<212> TYPE: DNA
<213> ORGANISM: Triticum aestivum

<400> SEQUENCE: 131
gaaggtgacc aagttcatgc tggtcatcca acatttaca tcgtta                  46

<210> SEQ ID NO 132
<211> LENGTH: 45
<212> TYPE: DNA
<213> ORGANISM: Triticum aestivum

<400> SEQUENCE: 132
gaaggtgacc aagttcatgc tctttgtttc taaatagctg cggcc                  45

<210> SEQ ID NO 133
<211> LENGTH: 45
<212> TYPE: DNA
<213> ORGANISM: Triticum aestivum

<400> SEQUENCE: 133
gaaggtgacc aagttcatgc tccaagtcgc aaatgtaagg tcaga                  45

<210> SEQ ID NO 134
<211> LENGTH: 45
<212> TYPE: DNA
<213> ORGANISM: Triticum aestivum

<400> SEQUENCE: 134
gaaggtgacc aagttcatgc ttcctctttt catcatgcac catta                  45

<210> SEQ ID NO 135
<211> LENGTH: 48
<212> TYPE: DNA
<213> ORGANISM: Triticum aestivum

<400> SEQUENCE: 135
gaaggtgacc aagttcatgc taaatgcaag tggcgaatct tatctcta               48

<210> SEQ ID NO 136
<211> LENGTH: 45
<212> TYPE: DNA
<213> ORGANISM: Triticum aestivum

<400> SEQUENCE: 136
gaaggtgacc aagttcatgc tactctggtg acaccatgta acttc                  45

<210> SEQ ID NO 137
```

```
<211> LENGTH: 43
<212> TYPE: DNA
<213> ORGANISM: Triticum aestivum

<400> SEQUENCE: 137
gaaggtgacc aagttcatgc tccaagtgtc cctccttgag tca              43

<210> SEQ ID NO 138
<211> LENGTH: 44
<212> TYPE: DNA
<213> ORGANISM: Triticum aestivum

<400> SEQUENCE: 138
gaaggtgacc aagttcatgc tcatacttgt agagatcgtc accc             44

<210> SEQ ID NO 139
<211> LENGTH: 47
<212> TYPE: DNA
<213> ORGANISM: Triticum aestivum

<400> SEQUENCE: 139
gaaggtgacc aagttcatgc tcttctgttt aggactacac atcaact          47

<210> SEQ ID NO 140
<211> LENGTH: 39
<212> TYPE: DNA
<213> ORGANISM: Triticum aestivum

<400> SEQUENCE: 140
gaaggtgacc aagttcatgc taagggcgcc ggcactggt                   39

<210> SEQ ID NO 141
<211> LENGTH: 50
<212> TYPE: DNA
<213> ORGANISM: Triticum aestivum

<400> SEQUENCE: 141
gaaggtgacc aagttcatgc tttagaaacg atctgcttac tgattactat       50

<210> SEQ ID NO 142
<211> LENGTH: 44
<212> TYPE: DNA
<213> ORGANISM: Triticum aestivum

<400> SEQUENCE: 142
gaaggtgacc aagttcatgc tggccagagc tatggacaaa gcaa             44

<210> SEQ ID NO 143
<211> LENGTH: 45
<212> TYPE: DNA
<213> ORGANISM: Triticum aestivum

<400> SEQUENCE: 143
gaaggtcgga gtcaacggat tgtgaacaaa acaggcctac aatcc            45

<210> SEQ ID NO 144
<211> LENGTH: 48
<212> TYPE: DNA
<213> ORGANISM: Triticum aestivum

<400> SEQUENCE: 144
gaaggtcgga gtcaacggat taagtactat ggctatgtct ctgaatgt         48
```

<210> SEQ ID NO 145
<211> LENGTH: 48
<212> TYPE: DNA
<213> ORGANISM: Triticum aestivum

<400> SEQUENCE: 145
gaaggtcgga gtcaacggat tagtagaata ccacccaata aatcactc            48

<210> SEQ ID NO 146
<211> LENGTH: 41
<212> TYPE: DNA
<213> ORGANISM: Triticum aestivum

<400> SEQUENCE: 146
gaaggtcgga gtcaacggat tctagccacg caaatgcccg c                   41

<210> SEQ ID NO 147
<211> LENGTH: 46
<212> TYPE: DNA
<213> ORGANISM: Triticum aestivum

<400> SEQUENCE: 147
gaaggtcgga gtcaacggat tctgtcgmac ccaatgaata atgttc              46

<210> SEQ ID NO 148
<211> LENGTH: 45
<212> TYPE: DNA
<213> ORGANISM: Triticum aestivum

<400> SEQUENCE: 148
gaaggtcgga gtcaacggat tgttccttgt gacatgtact catac               45

<210> SEQ ID NO 149
<211> LENGTH: 49
<212> TYPE: DNA
<213> ORGANISM: Triticum aestivum

<400> SEQUENCE: 149
gaaggtcgga gtcaacggat taacaacaat taygaggatc aaatggtct           49

<210> SEQ ID NO 150
<211> LENGTH: 41
<212> TYPE: DNA
<213> ORGANISM: Triticum aestivum

<400> SEQUENCE: 150
gaaggtcgga gtcaacggat tggttcctga gagagcaacc g                   41

<210> SEQ ID NO 151
<211> LENGTH: 54
<212> TYPE: DNA
<213> ORGANISM: Triticum aestivum

<400> SEQUENCE: 151
gaaggtcgga gtcaacggat tcaaattact tttgttcttt tattttttc gaac      54

<210> SEQ ID NO 152
<211> LENGTH: 51
<212> TYPE: DNA
<213> ORGANISM: Triticum aestivum

<400> SEQUENCE: 152
gaaggtcgga gtcaacggat taaacatcta ttccaagcaa gtattagtaa c        51

<210> SEQ ID NO 153
<211> LENGTH: 46
<212> TYPE: DNA
<213> ORGANISM: Triticum aestivum

<400> SEQUENCE: 153
gaaggtcgga gtcaacggat tcagctgcat aaaaamcaga ataccg        46

<210> SEQ ID NO 154
<211> LENGTH: 51
<212> TYPE: DNA
<213> ORGANISM: Triticum aestivum

<400> SEQUENCE: 154
gaaggtcgga gtcaacggat tataaattgt tcacaacatg gacatgagaa t        51

<210> SEQ ID NO 155
<211> LENGTH: 49
<212> TYPE: DNA
<213> ORGANISM: Triticum aestivum

<400> SEQUENCE: 155
gaaggtcgga gtcaacggat tgcacgtagt aagtattgat ttttctgtt        49

<210> SEQ ID NO 156
<211> LENGTH: 48
<212> TYPE: DNA
<213> ORGANISM: Triticum aestivum

<400> SEQUENCE: 156
gaaggtcgga gtcaacggat tgtttccatg ttaagcttat attgtgcg        48

<210> SEQ ID NO 157
<211> LENGTH: 47
<212> TYPE: DNA
<213> ORGANISM: Triticum aestivum

<400> SEQUENCE: 157
gaaggtcgga gtcaacggat tggaatctga ttaagacgct ggagaat        47

<210> SEQ ID NO 158
<211> LENGTH: 51
<212> TYPE: DNA
<213> ORGANISM: Triticum aestivum

<400> SEQUENCE: 158
gaaggtcgga gtcaacggat tgaagcttga taaggctatg cttatattta a        51

<210> SEQ ID NO 159
<211> LENGTH: 46
<212> TYPE: DNA
<213> ORGANISM: Triticum aestivum

<400> SEQUENCE: 159
gaaggtcgga gtcaacggat tgttaatgct gtagccattc ttgcag        46

<210> SEQ ID NO 160
<211> LENGTH: 40
<212> TYPE: DNA
<213> ORGANISM: Triticum aestivum

<400> SEQUENCE: 160
gaaggtcgga gtcaacggat tcgacgcgtc ttccgcaatg        40

<210> SEQ ID NO 161
<211> LENGTH: 46
<212> TYPE: DNA
<213> ORGANISM: Triticum aestivum

<400> SEQUENCE: 161
gaaggtcgga gtcaacggat tcaaagaggt gacaaatatg tgtacc         46

<210> SEQ ID NO 162
<211> LENGTH: 40
<212> TYPE: DNA
<213> ORGANISM: Triticum aestivum

<400> SEQUENCE: 162
gaaggtcgga gtcaacggat tgcctgagct gggctgcact         40

<210> SEQ ID NO 163
<211> LENGTH: 42
<212> TYPE: DNA
<213> ORGANISM: Triticum aestivum

<400> SEQUENCE: 163
gaaggtcgga gtcaacggat tcctggagat ggatccggtc aa         42

<210> SEQ ID NO 164
<211> LENGTH: 44
<212> TYPE: DNA
<213> ORGANISM: Triticum aestivum

<400> SEQUENCE: 164
gaaggtcgga gtcaacggat taatcgttct tcgagaagca ctcc         44

<210> SEQ ID NO 165
<211> LENGTH: 44
<212> TYPE: DNA
<213> ORGANISM: Triticum aestivum

<400> SEQUENCE: 165
gaaggtcgga gtcaacggat tcggaatcga gtcaaccaat tccc         44

<210> SEQ ID NO 166
<211> LENGTH: 46
<212> TYPE: DNA
<213> ORGANISM: Triticum aestivum

<400> SEQUENCE: 166
gaaggtcgga gtcaacggat tcgccttttc ttcttccagc atctat         46

<210> SEQ ID NO 167
<211> LENGTH: 54
<212> TYPE: DNA
<213> ORGANISM: Triticum aestivum

<400> SEQUENCE: 167
gaaggtcgga gtcaacggat tatattgttt gtattaaaaa gttgtgtgtt ttgc         54

<210> SEQ ID NO 168
<211> LENGTH: 42
<212> TYPE: DNA
<213> ORGANISM: Triticum aestivum

<400> SEQUENCE: 168

```
gaaggtcgga gtcaacggat tgccctgcgc aaaatcaaac tc                               42

<210> SEQ ID NO 169
<211> LENGTH: 46
<212> TYPE: DNA
<213> ORGANISM: Triticum aestivum

<400> SEQUENCE: 169
gaaggtcgga gtcaacggat tacaaagggc tatcctggtg aacaat                          46

<210> SEQ ID NO 170
<211> LENGTH: 51
<212> TYPE: DNA
<213> ORGANISM: Triticum aestivum

<400> SEQUENCE: 170
gaaggtcgga gtcaacggat taaatgccta gtctatacct gataaactaa t                    51

<210> SEQ ID NO 171
<211> LENGTH: 39
<212> TYPE: DNA
<213> ORGANISM: Triticum aestivum

<400> SEQUENCE: 171
gaaggtcgga gtcaacggat tgtcccccat ggcacctgc                                  39

<210> SEQ ID NO 172
<211> LENGTH: 52
<212> TYPE: DNA
<213> ORGANISM: Triticum aestivum

<400> SEQUENCE: 172
gaaggtcgga gtcaacggat taatttggtt aaccaaatcc tttttgattt tg                   52

<210> SEQ ID NO 173
<211> LENGTH: 39
<212> TYPE: DNA
<213> ORGANISM: Triticum aestivum

<400> SEQUENCE: 173
gaaggtcgga gtcaacggat tttctcaccg gcatctccg                                  39

<210> SEQ ID NO 174
<211> LENGTH: 49
<212> TYPE: DNA
<213> ORGANISM: Triticum aestivum

<400> SEQUENCE: 174
gaaggtcgga gtcaacggat tcttcccatg ttctttttt gctcaaaat                        49

<210> SEQ ID NO 175
<211> LENGTH: 45
<212> TYPE: DNA
<213> ORGANISM: Triticum aestivum

<400> SEQUENCE: 175
gaaggtcgga gtcaacggat tactgggtgc aaagccaaga tgata                           45

<210> SEQ ID NO 176
<211> LENGTH: 47
<212> TYPE: DNA
<213> ORGANISM: Triticum aestivum

<400> SEQUENCE: 176
```

-continued gaaggtcgga gtcaacggat tgaaagagca tgtcagacac aatgcaa    47

<210> SEQ ID NO 177
<211> LENGTH: 43
<212> TYPE: DNA
<213> ORGANISM: Triticum aestivum

<400> SEQUENCE: 177
gaaggtcgga gtcaacggat tgcgaaactt cgccgcgata aac    43

<210> SEQ ID NO 178
<211> LENGTH: 47
<212> TYPE: DNA
<213> ORGANISM: Triticum aestivum

<400> SEQUENCE: 178
gaaggtcgga gtcaacggat taagttgctc ttaattatct gtgcgtg    47

<210> SEQ ID NO 179
<211> LENGTH: 51
<212> TYPE: DNA
<213> ORGANISM: Triticum aestivum

<400> SEQUENCE: 179
gaaggtcgga gtcaacggat tagcaagtag agttaactta tcaagttatt g    51

<210> SEQ ID NO 180
<211> LENGTH: 44
<212> TYPE: DNA
<213> ORGANISM: Triticum aestivum

<400> SEQUENCE: 180
gaaggtcgga gtcaacggat tgacatctga tgagccagca tacc    44

<210> SEQ ID NO 181
<211> LENGTH: 43
<212> TYPE: DNA
<213> ORGANISM: Triticum aestivum

<400> SEQUENCE: 181
gaaggtcgga gtcaacggat tcacctcctc cgtatctgat ggt    43

<210> SEQ ID NO 182
<211> LENGTH: 46
<212> TYPE: DNA
<213> ORGANISM: Triticum aestivum

<400> SEQUENCE: 182
gaaggtcgga gtcaacggat tctactcatc tattgcagat gctctg    46

<210> SEQ ID NO 183
<211> LENGTH: 46
<212> TYPE: DNA
<213> ORGANISM: Triticum aestivum

<400> SEQUENCE: 183
gaaggtcgga gtcaacggat tatgacatgg aggattatat cgacgg    46

<210> SEQ ID NO 184
<211> LENGTH: 45
<212> TYPE: DNA
<213> ORGANISM: Triticum aestivum -continued

<400> SEQUENCE: 184
gaaggtcgga gtcaacggat taggtcgtag cacatagccg tttat    45

<210> SEQ ID NO 185
<211> LENGTH: 48
<212> TYPE: DNA
<213> ORGANISM: Triticum aestivum

<400> SEQUENCE: 185
gaaggtcgga gtcaacggat tgcttctttt ttctccctat aatatggg    48

<210> SEQ ID NO 186
<211> LENGTH: 46
<212> TYPE: DNA
<213> ORGANISM: Triticum aestivum

<400> SEQUENCE: 186
gaaggtcgga gtcaacggat tgggcaactc tcttcttctt aatcag    46

<210> SEQ ID NO 187
<211> LENGTH: 44
<212> TYPE: DNA
<213> ORGANISM: Triticum aestivum

<400> SEQUENCE: 187
gaaggtcgga gtcaacggat taatgatgac tccatgaggg tggt    44

<210> SEQ ID NO 188
<211> LENGTH: 43
<212> TYPE: DNA
<213> ORGANISM: Triticum aestivum

<400> SEQUENCE: 188
gaaggtcgga gtcaacggat tagccaagga agcccagatt ttg    43

<210> SEQ ID NO 189
<211> LENGTH: 45
<212> TYPE: DNA
<213> ORGANISM: Triticum aestivum

<400> SEQUENCE: 189
gaaggtcgga gtcaacggat tcagatcatt acccaacggc caatt    45

<210> SEQ ID NO 190
<211> LENGTH: 46
<212> TYPE: DNA
<213> ORGANISM: Triticum aestivum

<400> SEQUENCE: 190
gaaggtcgga gtcaacggat tggtcatcca aacatttaca tcgttc    46

<210> SEQ ID NO 191
<211> LENGTH: 47
<212> TYPE: DNA
<213> ORGANISM: Triticum aestivum

<400> SEQUENCE: 191
gaaggtcgga gtcaacggat tctctttgtt tctaaatagc tgcggct    47

<210> SEQ ID NO 192
<211> LENGTH: 44
<212> TYPE: DNA
<213> ORGANISM: Triticum aestivum

<400> SEQUENCE: 192
gaaggtcgga gtcaacggat tcaagtcgca aatgtaaggt cagc                44

<210> SEQ ID NO 193
<211> LENGTH: 47
<212> TYPE: DNA
<213> ORGANISM: Triticum aestivum

<400> SEQUENCE: 193
gaaggtcgga gtcaacggat tcttcctctt ttcatcatgc accattg              47

<210> SEQ ID NO 194
<211> LENGTH: 46
<212> TYPE: DNA
<213> ORGANISM: Triticum aestivum

<400> SEQUENCE: 194
gaaggtcgga gtcaacggat tatgcaagtg gcgaatctta tctctg               46

<210> SEQ ID NO 195
<211> LENGTH: 46
<212> TYPE: DNA
<213> ORGANISM: Triticum aestivum

<400> SEQUENCE: 195
gaaggtcgga gtcaacggat tgactctggt gacaccatgt aacttt               46

<210> SEQ ID NO 196
<211> LENGTH: 42
<212> TYPE: DNA
<213> ORGANISM: Triticum aestivum

<400> SEQUENCE: 196
gaaggtcgga gtcaacggat tcaagtgtcc ctccttgagt cg                   42

<210> SEQ ID NO 197
<211> LENGTH: 46
<212> TYPE: DNA
<213> ORGANISM: Triticum aestivum

<400> SEQUENCE: 197
gaaggtcgga gtcaacggat tgtcatactt gtagagatcg tcacca               46

<210> SEQ ID NO 198
<211> LENGTH: 47
<212> TYPE: DNA
<213> ORGANISM: Triticum aestivum

<400> SEQUENCE: 198
gaaggtcgga gtcaacggat tcttctgttt aggactacac atcaacc              47

<210> SEQ ID NO 199
<211> LENGTH: 38
<212> TYPE: DNA
<213> ORGANISM: Triticum aestivum

<400> SEQUENCE: 199
gaaggtcgga gtcaacggat tagggcgccg gcactggc                        38

<210> SEQ ID NO 200
<211> LENGTH: 48
<212> TYPE: DNA

<213> ORGANISM: Triticum aestivum

<400> SEQUENCE: 200
gaaggtcgga gtcaacggat tagaaacgat ctgcttactg attactag         48

<210> SEQ ID NO 201
<211> LENGTH: 43
<212> TYPE: DNA
<213> ORGANISM: Triticum aestivum

<400> SEQUENCE: 201
gaaggtcgga gtcaacggat tgccagagct atggacaaag cag             43

<210> SEQ ID NO 202
<211> LENGTH: 29
<212> TYPE: DNA
<213> ORGANISM: Triticum aestivum

<400> SEQUENCE: 202
gtgtgtgcta atgtggatat acgtaagtt                             29

<210> SEQ ID NO 203
<211> LENGTH: 30
<212> TYPE: DNA
<213> ORGANISM: Triticum aestivum

<400> SEQUENCE: 203
acgacaatat agacaaataa aaccaaacaa                            30

<210> SEQ ID NO 204
<211> LENGTH: 29
<212> TYPE: DNA
<213> ORGANISM: Triticum aestivum

<400> SEQUENCE: 204
aagtagtact cgtagagagt taacacaga                             29

<210> SEQ ID NO 205
<211> LENGTH: 25
<212> TYPE: DNA
<213> ORGANISM: Triticum aestivum

<400> SEQUENCE: 205
ccttgtccac cgagacatgt acaaa                                 25

<210> SEQ ID NO 206
<211> LENGTH: 21
<212> TYPE: DNA
<213> ORGANISM: Triticum aestivum

<400> SEQUENCE: 206
gccatcctct cggagccaga a                                     21

<210> SEQ ID NO 207
<211> LENGTH: 25
<212> TYPE: DNA
<213> ORGANISM: Triticum aestivum

<400> SEQUENCE: 207
caaggatggg gagtatatgg ctctt                                 25

<210> SEQ ID NO 208
<211> LENGTH: 30

```
<212> TYPE: DNA
<213> ORGANISM: Triticum aestivum

<400> SEQUENCE: 208
atcattgcca cgraaaaaat ctcacaagat                                        30

<210> SEQ ID NO 209
<211> LENGTH: 23
<212> TYPE: DNA
<213> ORGANISM: Triticum aestivum

<400> SEQUENCE: 209
gcttcctctc ggtagcgatg gat                                               23

<210> SEQ ID NO 210
<211> LENGTH: 29
<212> TYPE: DNA
<213> ORGANISM: Triticum aestivum

<400> SEQUENCE: 210
atatgattca ccctagatcc ttcacctta                                         29

<210> SEQ ID NO 211
<211> LENGTH: 30
<212> TYPE: DNA
<213> ORGANISM: Triticum aestivum

<400> SEQUENCE: 211
aataactctt gtacttcagg atgaacgttt                                        30

<210> SEQ ID NO 212
<211> LENGTH: 25
<212> TYPE: DNA
<213> ORGANISM: Triticum aestivum

<400> SEQUENCE: 212
ctgcgttaag gttcaggcaa ctgat                                             25

<210> SEQ ID NO 213
<211> LENGTH: 21
<212> TYPE: DNA
<213> ORGANISM: Triticum aestivum

<400> SEQUENCE: 213
gtttcctcca atgttcttcc c                                                 21

<210> SEQ ID NO 214
<211> LENGTH: 29
<212> TYPE: DNA
<213> ORGANISM: Triticum aestivum

<400> SEQUENCE: 214
gccaattttc aaatctaagt ccacagaga                                         29

<210> SEQ ID NO 215
<211> LENGTH: 29
<212> TYPE: DNA
<213> ORGANISM: Triticum aestivum

<400> SEQUENCE: 215 gcccttttggt aattccattt caatctttt                                        29

<210> SEQ ID NO 216
```

```
<211> LENGTH: 26
<212> TYPE: DNA
<213> ORGANISM: Triticum aestivum

<400> SEQUENCE: 216
cagatggcct agtcgtgaca tatctt                                        26

<210> SEQ ID NO 217
<211> LENGTH: 24
<212> TYPE: DNA
<213> ORGANISM: Triticum aestivum

<400> SEQUENCE: 217
ctcactcctt gtttctgcat atct                                          24

<210> SEQ ID NO 218
<211> LENGTH: 24
<212> TYPE: DNA
<213> ORGANISM: Triticum aestivum

<400> SEQUENCE: 218
gtgcccataa gacgactggg acaa                                          24

<210> SEQ ID NO 219
<211> LENGTH: 19
<212> TYPE: DNA
<213> ORGANISM: Triticum aestivum

<400> SEQUENCE: 219
ccgcggccga agcaggcaa                                                19

<210> SEQ ID NO 220
<211> LENGTH: 29
<212> TYPE: DNA
<213> ORGANISM: Triticum aestivum

<400> SEQUENCE: 220
taaaagaaca caaatgtggc cctagtgat                                     29

<210> SEQ ID NO 221
<211> LENGTH: 24
<212> TYPE: DNA
<213> ORGANISM: Triticum aestivum

<400> SEQUENCE: 221
gaccgtggta tatgccacca cgtt                                          24

<210> SEQ ID NO 222
<211> LENGTH: 22
<212> TYPE: DNA
<213> ORGANISM: Triticum aestivum

<400> SEQUENCE: 222
tcctcacaaa tcacgggccc ct                                            22

<210> SEQ ID NO 223
<211> LENGTH: 30
<212> TYPE: DNA
<213> ORGANISM: Triticum aestivum

<400> SEQUENCE: 223
aatatgatac agacccaaga caaaccattt                                    30
```

```
<210> SEQ ID NO 224
<211> LENGTH: 25
<212> TYPE: DNA
<213> ORGANISM: Triticum aestivum

<400> SEQUENCE: 224
gcatcttcaa gggagccact caaaa                                           25

<210> SEQ ID NO 225
<211> LENGTH: 25
<212> TYPE: DNA
<213> ORGANISM: Triticum aestivum

<400> SEQUENCE: 225
ttgactcgat tccgtgtgag gctaa                                           25

<210> SEQ ID NO 226
<211> LENGTH: 30
<212> TYPE: DNA
<213> ORGANISM: Triticum aestivum

<400> SEQUENCE: 226
gttgatgcga atttgaaaat gacataataa                                      30

<210> SEQ ID NO 227
<211> LENGTH: 22
<212> TYPE: DNA
<213> ORGANISM: Triticum aestivum

<400> SEQUENCE: 227
gggcgggacc tgacttgatg at                                              22

<210> SEQ ID NO 228
<211> LENGTH: 29
<212> TYPE: DNA
<213> ORGANISM: Triticum aestivum

<400> SEQUENCE: 228
ggcttcatta tcaaattctg acccatctt                                       29

<210> SEQ ID NO 229
<211> LENGTH: 29
<212> TYPE: DNA
<213> ORGANISM: Triticum aestivum

<400> SEQUENCE: 229
tgtaccgaaa ctcaaccaaa tgaccattt                                       29

<210> SEQ ID NO 230
<211> LENGTH: 24
<212> TYPE: DNA
<213> ORGANISM: Triticum aestivum

<400> SEQUENCE: 230
cttctctgtg gccgaaaacc tctt                                            24

<210> SEQ ID NO 231
<211> LENGTH: 30
<212> TYPE: DNA
<213> ORGANISM: Triticum aestivum

<400> SEQUENCE: 231
gcacaatgtt tgacattcgg ttttctagtt                                      30
```

```
<210> SEQ ID NO 232
<211> LENGTH: 29
<212> TYPE: DNA
<213> ORGANISM: Triticum aestivum

<400> SEQUENCE: 232
cctaccatcc ttaaatactc ttgctcaaa                                        29

<210> SEQ ID NO 233
<211> LENGTH: 30
<212> TYPE: DNA
<213> ORGANISM: Triticum aestivum

<400> SEQUENCE: 233
aagcaactag aaaaatattt ggactagcat                                       30

<210> SEQ ID NO 234
<211> LENGTH: 25
<212> TYPE: DNA
<213> ORGANISM: Triticum aestivum

<400> SEQUENCE: 234
cctcccaacg gccatcaatc aattt                                            25

<210> SEQ ID NO 235
<211> LENGTH: 29
<212> TYPE: DNA
<213> ORGANISM: Triticum aestivum

<400> SEQUENCE: 235
cctgctggaa atgggatttc ttgtttatt                                        29

<210> SEQ ID NO 236
<211> LENGTH: 26
<212> TYPE: DNA
<213> ORGANISM: Triticum aestivum

<400> SEQUENCE: 236
gatcatcggg gaacctgatg atagtt                                           26

<210> SEQ ID NO 237
<211> LENGTH: 28
<212> TYPE: DNA
<213> ORGANISM: Triticum aestivum

<400> SEQUENCE: 237
ttggttggtt acgtcaggtt aagactta                                         28

<210> SEQ ID NO 238
<211> LENGTH: 28
<212> TYPE: DNA
<213> ORGANISM: Triticum aestivum

<400> SEQUENCE: 238
gctktagact ctaagtacca cagaagaa                                         28

<210> SEQ ID NO 239
<211> LENGTH: 26
<212> TYPE: DNA
<213> ORGANISM: Triticum aestivum

<400> SEQUENCE: 239
gggacgtgga atttggaaag acacat                                           26
```

<210> SEQ ID NO 240
<211> LENGTH: 22
<212> TYPE: DNA
<213> ORGANISM: Triticum aestivum

<400> SEQUENCE: 240
cagaaggcac tgggagggga tt                                           22

<210> SEQ ID NO 241
<211> LENGTH: 29
<212> TYPE: DNA
<213> ORGANISM: Triticum aestivum

<400> SEQUENCE: 241
tataggagtg atagcaccac acaattcat                                    29

<210> SEQ ID NO 242
<211> LENGTH: 22
<212> TYPE: DNA
<213> ORGANISM: Triticum aestivum

<400> SEQUENCE: 242
atacatgtcg gcgtcccagt cc                                           22

<210> SEQ ID NO 243
<211> LENGTH: 29
<212> TYPE: DNA
<213> ORGANISM: Triticum aestivum

<400> SEQUENCE: 243
gaaacattcc ttcggacaac tatgcatta                                    29

<210> SEQ ID NO 244
<211> LENGTH: 25
<212> TYPE: DNA
<213> ORGANISM: Triticum aestivum

<400> SEQUENCE: 244
accctcgctg cagttccttc ttaaa                                        25

<210> SEQ ID NO 245
<211> LENGTH: 29
<212> TYPE: DNA
<213> ORGANISM: Triticum aestivum

<400> SEQUENCE: 245
tttaggacct ccagtgcatt taactcttt                                    29

<210> SEQ ID NO 246
<211> LENGTH: 22
<212> TYPE: DNA
<213> ORGANISM: Triticum aestivum

<400> SEQUENCE: 246
cagtgcaacc tgcggagagc at                                           22

<210> SEQ ID NO 247
<211> LENGTH: 26
<212> TYPE: DNA
<213> ORGANISM: Triticum aestivum

<400> SEQUENCE: 247
caactgcttg gagaaaggca acacaa                                           26

<210> SEQ ID NO 248
<211> LENGTH: 29
<212> TYPE: DNA
<213> ORGANISM: Triticum aestivum

<400> SEQUENCE: 248
ccattaacaa gtactgcata ggtgcatat                                        29

<210> SEQ ID NO 249
<211> LENGTH: 28
<212> TYPE: DNA
<213> ORGANISM: Triticum aestivum

<400> SEQUENCE: 249
cctcctccta attaagctcc tatagata                                         28

<210> SEQ ID NO 250
<211> LENGTH: 25
<212> TYPE: DNA
<213> ORGANISM: Triticum aestivum

<400> SEQUENCE: 250
aaacgtgcaa cgaggcaaac ctcat                                            25

<210> SEQ ID NO 251
<211> LENGTH: 21
<212> TYPE: DNA
<213> ORGANISM: Triticum aestivum

<400> SEQUENCE: 251
gccgcatggt ttgggcggaa a                                                21

<210> SEQ ID NO 252
<211> LENGTH: 30
<212> TYPE: DNA
<213> ORGANISM: Triticum aestivum

<400> SEQUENCE: 252
gtgcctctag gttcaacata aatttaggta                                       30

<210> SEQ ID NO 253
<211> LENGTH: 30
<212> TYPE: DNA
<213> ORGANISM: Triticum aestivum

<400> SEQUENCE: 253
gattttcatt atcatgatca tcattcattt                                       30

<210> SEQ ID NO 254
<211> LENGTH: 29
<212> TYPE: DNA
<213> ORGANISM: Triticum aestivum

<400> SEQUENCE: 254
aatggcttca gacaaaataa gagggagat                                        29

<210> SEQ ID NO 255
<211> LENGTH: 29
<212> TYPE: DNA
<213> ORGANISM: Triticum aestivum

<400> SEQUENCE: 255

```
tctcgccttt gttttgccaa atggtataa                                    29

<210> SEQ ID NO 256
<211> LENGTH: 22
<212> TYPE: DNA
<213> ORGANISM: Triticum aestivum

<400> SEQUENCE: 256
caaactccaa cgggtggtgc gt                                           22

<210> SEQ ID NO 257
<211> LENGTH: 25
<212> TYPE: DNA
<213> ORGANISM: Triticum aestivum

<400> SEQUENCE: 257
gcaatccacc actgtggtac aactt                                        25

<210> SEQ ID NO 258
<211> LENGTH: 25
<212> TYPE: DNA
<213> ORGANISM: Triticum aestivum

<400> SEQUENCE: 258
ggcacgatga cagtaatggg atgtt                                        25

<210> SEQ ID NO 259
<211> LENGTH: 29
<212> TYPE: DNA
<213> ORGANISM: Triticum aestivum

<400> SEQUENCE: 259
agagtacaca gcattttccc aggaatata                                    29

<210> SEQ ID NO 260
<211> LENGTH: 24
<212> TYPE: DNA
<213> ORGANISM: Triticum aestivum

<400> SEQUENCE: 260
gtggcaagca gatcatgaca ggtt                                         24

<210> SEQ ID NO 261
<211> LENGTH: 26
<212> TYPE: DNA
<213> ORGANISM: Triticum aestivum

<400> SEQUENCE: 261
cttgacgcat aaggtgaaag cctgaa                                       26

<210> SEQ ID NO 262
<211> LENGTH: 26
<212> TYPE: DNA
<213> ORGANISM: Triticum aestivum

<400> SEQUENCE: 262
cctttatcaa tcatctgccg gaggaa                                       26

<210> SEQ ID NO 263
<211> LENGTH: 201
<212> TYPE: DNA
<213> ORGANISM: Triticum aestivum
```

<400> SEQUENCE: 263

```
gaacaatctc cccctacgat tgactgacga cgacgagatc ccacagtcaa gccctccatt      60
ttcctcagaa aactctaacg attcttacac acgcaccaaa kccgtcacaa gtttacagac     120
ccctggcatg gatgcacgca cggtgcagcc agccggccca ggattttcat acgtttgcta     180
tacgttacgt cgagagggag t                                               201
```

<210> SEQ ID NO 264
<211> LENGTH: 201
<212> TYPE: DNA
<213> ORGANISM: Triticum aestivum

<400> SEQUENCE: 264

```
tcaattcctt gttgtccttc ttcagttcct cgttgtgctt ggccagcttc cttttgccct      60
ccaccagcac ctcgttcctc ttctccagat aatcaatcct matcttttt ttctcatcga     120
gctccgtcgc caactttcct ttcttctcca ccagcgcatt ttttgccttt tccagatctg     180
caatatctgt tccctttttt t                                               201
```

<210> SEQ ID NO 265
<211> LENGTH: 44
<212> TYPE: DNA
<213> ORGANISM: Triticum aestivum

<400> SEQUENCE: 265

```
gaaggtgacc aagttcatgc tggggtctgt aaacttgtga cgga                       44
```

<210> SEQ ID NO 266
<211> LENGTH: 43
<212> TYPE: DNA
<213> ORGANISM: Triticum aestivum

<400> SEQUENCE: 266

```
gaaggtcgga gtcaacggat tgggtctgta aacttgtgac ggc                        43
```

<210> SEQ ID NO 267
<211> LENGTH: 27
<212> TYPE: DNA
<213> ORGANISM: Triticum aestivum

<400> SEQUENCE: 267

```
ctctaacgat tcttacacac gcaccaa                                          27
```

<210> SEQ ID NO 268
<211> LENGTH: 46
<212> TYPE: DNA
<213> ORGANISM: Triticum aestivum

<400> SEQUENCE: 268

```
gaaggtgacc aagttcatgc tcctcttctc cagataatca atcctc                     46
```

<210> SEQ ID NO 269
<211> LENGTH: 46
<212> TYPE: DNA
<213> ORGANISM: Triticum aestivum

<400> SEQUENCE: 269

```
gaaggtcgga gtcaacggat tcctcttctc cagataatca atccta                     46
```

<210> SEQ ID NO 270
<211> LENGTH: 22

```
<212> TYPE: DNA
<213> ORGANISM: Triticum aestivum

<400> SEQUENCE: 270
ggcgacggag ctcgatgaga aa                                          22
```

WHEAT COMPRISING MALE FERTILITY RESTORER ALLELES

The invention is in the field of plant genetics and plant breeding. The invention more specifically relates to wheat plants carrying restorer of fertility genes specific to *T. timopheevii* CMS cytoplasm.

BACKGROUND

Hybrid production is based on crossing two parental lines to beneficiate of heterosis and de facto, increase genetic variability to create new varieties or genotypes with higher yield and better adapted to environmental stresses. Even in a predominantly autogamous species like wheat, research studies have shown that hybrid lines exhibit improved quality and greater tolerance to environmental and biotic stresses.

In order to promote commercially viable rates of hybrid production, self-fertilization must be avoided, i.e. fertilization of the female organ by the pollen of the same plant. It is desired that the female organ of the female parent is exclusively fertilized with the pollen of the male parent.

Male sterility can be achieved by three different ways. Manual emasculation is the simplest one and is still used in some species where male and female flowers are separated, e.g. corn. However, it is impractical in species like wheat where flowers contain both female and male organs. Male sterility can be induced by chemical hybridization agents (CHAs) with gametocidal effects. Currently, only a few commercial hybrid wheat cultivars are based on this technology as it can bear substantial financial risks.

Finally, male sterility can also be induced by genetic means. There are many examples of hybrid systems in corn or sorghum based on male sterility induced by genetic means showing the preponderance of this technology compared to the two mentioned previously. However, in other species which are predominantly self-pollinated like wheat, hybrid production is still a challenge (Longin et al., 2012).

A system that has been successfully used for production of hybrid in several crop plants including maize, rice and sorghum is the three-line breeding system based on cytoplasmic male sterility (CMS), a genetically conditioned trait that leads to plant sterility.

In order to obtain a reliable and efficient system for producing seeds needed for hybrid production, one generally needs three essential elements: a means to induce male sterility, a means to propagate the sterility, and a means to restore fertility. For example, a fully genetically based system is composed of a male-sterile line (female parent), a fertile maintainer line (male parent allowing propagation of the male-sterile line), and a fertility restorer line (male parent for hybrid production).

The first case of cytoplasmic male sterility in wheat was observed in 1951 (Kihara, 1951), where it was observed that sterility was caused by incompatibility between the cytoplasm of *Aegilops caudata* L. and the nucleus of *T. aestivum* var. *erythrospermum*. Subsequently research on *T. timopheevii* cytoplasm showed that this cytoplasm is able to induce sterility in bread wheat (*T. aestivum*) (Wilson and Ross, 1961, Crop Sci, 1: 191-193). Orf256 was previously identified as a gene specific to the *T. timopheevii* mitochondrial genome (Rathburn and Hedgcoth, 1991; Song and Hedgcoth, 1994) responsive of CMS. This hypothesis was recently overcome by Ian Small and Joanna Melonek who pointed the Orf279 mitochondrial protein to being responsive of T-CMS (WO 2020/161261, Melonek and al., 2021).

It was expected that such a cytoplasm could be used in a hybrid production system. However, major limitations arose from the difficulty in finding a completely dominant and stable fertility restorer gene with no negative side effects (notably on yield).

Fertility restoration of male sterile plants harboring *T. timopheevii* CMS cytoplasm (T-CMS cytoplasm) has been reported and nine major restorer loci (designated as Rf1 to Rf9) have been identified and located approximate within the wheat genome (Shahinnia et al., 2020). One of the most effective restorer loci is Rf3 (Ma and Sorrells, 1995; Kojima et al., 1997; Ahmed et al., 2001; Geyer et al., 2016). Two SNP markers allowed the location of the Rf3 locus within a 2 cM fragment on chromosome 1B (Geyer et al., 2016).

While it is understood that restoration to normal pollen fertility could require two or more Rf loci, it is also well known that modifier loci exist that have either minor effect with low penetrance (Zhou et al., 2005; Stojalowski et al., 2013) or inhibitory effects on fertility, depending on environmental conditions (Wilson et al., 1984). It is not yet understood which combination of genes or loci is needed to complete a full restoration of T-CMS in different genetic backgrounds and environmental conditions.

In this context, the development of technologies that enable a full restoration of pollen fertility is of major importance in wheat. WO2019/086510 discloses wheat plants restorer of fertility with some combinations of restorer loci. However, there is still a need to develop new wheat plants restorer of fertility.

It is therefore the object of the present invention to propose suitable fertility restorer genes in wheat for the development of a hybrid production system useful for the seed industry.

SUMMARY

A first object of the present disclosure relates to a wheat plant restorer of fertility of *T. timopheevii* CMS cytoplasm comprising at least Rf1, Rf3, and Rf4s restorer of fertility alleles. It also relates to a wheat plant restorer of fertility of *T. timopheevii* CMS cytoplasm, wherein the plant comprises at least Rf1, Rf3, and 6R restorer of fertility alleles.

Another aspect relates to a method of identifying a wheat plant by detecting the presence of at least one restorer allele within one or more of Rf1, Rf3, Rf4s, Rf7 and 6R loci, preferably within the three Rf1, Rf3 and Rf4s loci or within the three Rf1, Rf3 and 6R loci.

The disclosure further relates to a method for producing a wheat hybrid plant comprising the steps of:
- providing a first wheat plant comprising one or two restorer allele selected among Rf1, Rf3 and Rf4s restorer alleles,
- crossing said first wheat plant with a second wheat plant comprising one or two restorer alleles selected among Rf1, Rf3 and Rf4s restorer alleles, wherein Rf1, Rf3 and Rf4s restorer alleles are represented at least once in the panel of restorer alleles provided by the first plant and the second plant,
- collecting the F1 hybrid seed,
- obtaining homozygous plants from the F1 plants,
- detecting the presence of the Rf1, Rf3 and Rf4s restorer alleles in the hybrid seed and/or at each generation.

Further, the disclosure also relates to a method for producing a wheat hybrid plant comprising the steps of:
- providing a first wheat plant comprising one or two restorer allele selected among Rf1, Rf3 and 6R restorer alleles, crossing said first wheat plant with a second wheat plant comprising one or two restorer alleles selected among Rf1, Rf3 and 6R restorer alleles, wherein Rf1, Rf3 and 6R restorer alleles are represented at least once in the panel of restorer alleles provided by the first plant and the second plant, collecting the F1 hybrid seed, obtaining homozygous plants from the F1 plants, detecting the presence of the Rf1, Rf3 and 6R restorer alleles in the hybrid seed and/or at each generation.

Yet another aspect of the disclosure relates to a method for producing a wheat hybrid plant comprising the steps of:

crossing a sterile female comprising the *T. timopheevii* cytoplasm with a fertile male wheat plant according to the disclosure;

collecting the hybrid seed;

optionally detecting the presence of *T. timopheevii* cytoplasm, and/or at least three of the Rf locus chosen amongst Rf1, Rf3, Rf4s, Rf7 and 6R in the hybrid seed;

optionally detecting hybridity level of the hybrid seeds.

DETAILED DESCRIPTION

The Wheat Plant Restorer of Fertility of *T. Timopheevi* CMS Cytoplasm

The inventors have shown that a combination of at least 3 specific fertility restorer alleles enable the obtention of wheat plants with full restoration of fertility of *T. timopheevi* CMS cytoplasm. Particularly, the wheat plant comprises at least a fertility restorer allele A, a fertility restorer allele B and a fertility restorer allele C.

As used herein, a fertility restorer A corresponds to Rf3.

As used herein, a fertility restorer B corresponds to Rf1 or Rf7.

As used herein, a fertility restorer C corresponds to Rf4s or 6R.

Therefore, a first aspect of the present disclosure relates to a wheat plant restorer of fertility of *T. timopheevii* CMS cytoplasm, wherein the wheat plant comprises at least three fertility restorer alleles:

Rf3, and

Rf1 and/or Rf7, and

Rf4s and/or 6R. In specific embodiments, the wheat plant comprises at least the three fertility restorer alleles: Rf3, Rf1, and Rf4s.

In specific embodiments, the wheat plant comprises at least the three fertility restorer alleles: Rf3, Rf1, and 6R.

In specific embodiments, the wheat plant comprises at least the three fertility restorer alleles: Rf3, Rf7, and Rf4s.

In specific embodiments, the wheat plant comprises at least the three fertility restorer alleles: Rf3, Rf7, and 6R.

In another specific embodiments, the wheat plant comprises at least the four fertility restorer alleles: Rf3, Rf1, Rf7, and Rf4s.

In another specific embodiments, the wheat plant comprises at least the four fertility restorer alleles: Rf3, Rf1, Rf4s and 6R.

In another specific embodiments, the wheat plant comprises at least the four fertility restorer alleles: Rf3, Rf1, Rf7, and 6R.

In another specific embodiments, the wheat plant comprises at least the four fertility restorer alleles: Rf3, Rf4s, Rf7, and 6R.

This list of examples is not exhaustive.

As described in WO 2019/086510, the inventors have identified two types of Rf3 restorer of fertility, one with a strong fertility restoration, and another with a weak fertility restoration. Rf3 strong and weak alleles can be associated to these combinations of three or four alleles. The Rf3 weak allele should be preferentially associated in a four allele combination.

Whenever reference to a "plant" or "plants" is made, it is understood that also plant parts (cells, tissues or organs, seed pods, seeds, severed parts such as roots, leaves, flowers, pollen, etc.), progeny of the plants which retain the distinguishing characteristics of the parents (especially, male fertility associated with the claimed Rf nucleic acids), such as seed obtained by selfing or crossing, e.g. hybrid seeds (obtained by crossing two inbred parent plants), hybrid plants and plant parts derived therefrom are encompassed herein, unless otherwise indicated.

As used herein, the term "Rf4s" refers to restorer allele Rf4 from *Aegilops speltoides*.

As used herein, the expression "wheat plant" refers to species of the genus *Triticum* as for example, *T. aestivum, T. aethiopicum, T. araraticum, T. boeoticum, T. carthlicum, T. compactum, T. dicoccoides, T. dicoccon, T. durum, T. ispahanicum, T. karamyschevii, T. macha, T. militinae, T. monococcum, T. polonicum, T. spelta, T. sphaerococcum, T. timopheevii, T. turanicum, T. turgidum, T. urartu, T. vavilovii, T. zhukovskyi* Faegi. Wheat plant also refers to species of the genera *Aegilops* and *Triticale*.

As used herein, the expression "restorer of fertility of *T. timopheevi* CMS cytoplasm" refers to a protein whose expression in a wheat plant comprising *T. timopheevi* CMS cytoplasm contributes to the restoration of the production of pollen in the *Triticum timopheevii* CMS system.

As used herein, the term "allele(s)" means any of one or more alternative forms of a gene at a particular locus. In a diploid, alleles of a given gene are located at a specific location or locus on a chromosome. One allele is present on each chromosome of the pair of homologous chromosomes. The same definition is used for plants bearing a higher level of ploidy like in Triticum gender wherein, for example, *T. aestivum* is an hexaploid plant.

As used herein, the expression "restorer allele of *T. timopheevi* CMS cytoplasm" refers to an allele which contributes to the restoration of the production of pollen in the CMS *Triticum timopheevii* system.

The restoration of pollen fertility may be partial or complete. In particular, the fertility score of F1 wheat plants having CMS-T *timopheevii* cytoplasm (from crosses between CMS female lines and restorer lines) may be calculated by dividing the total number of seeds threshed from a spike by the number of counted spikelets and may be compared with the fertility scores of a panel of control fertile plants, for example elite inbred lines bearing a normal wheat cytoplasm, grown in the same area and under the same agro-environmental conditions. It is preferred that such panels of lines comprise a set of at least 5 elite inbred lines wherein these lines are representative of the area where the fertility test is achieved. Besides, it is preferred that at least 10 spikes from different individual F1 plants be assessed for a given experiment. Examples of pollen fertility tests are described in WO2019/086510.

If the fertility score is not null, then the plant has acquired partial or full restoration of fertility. For each fertility score, a statistical test is calculated to obtain a p-value. Examples of statistical tests are the Anova or mean comparison tests. A p-value below a 5% threshold will indicate that the two distributions are statistically different. Therefore, a significant decrease of the fertility score of the tested wheat plant as compared to the fertility score of the fully fertile control plant is indicative that the F1 plant has not acquired full restoration of fertility (i.e. partial restoration). A similar or higher fertility score is indicative that the F1 plant has acquired full restoration of fertility. In a preferred embodiment, the wheat plant, such as transgenic or genetically engineered wheat plant, according to the present disclosure, has acquired full restoration of fertility.

As used herein, the term "crossing" can refer to a simple X by Y cross, or also to the process of backcrossing, depending on the context.

The loci of the restorer alleles of *T. timopheevi* CMS cytoplasm within Rf1, Rf3 and Rf7 have been previously mapped in the WO2019/086510. The corresponding restorer alleles are designated Rf1, Rf3, and Rf7 restorer alleles and have been described in the art.

Further, it is hereby disclosed the mapping of Rf4s restorer allele and a wheat plant comprising thereof.

In particular, a wheat plant source of the Rf3 restorer allele includes the commercial following lines: Allezy, Altigo, Altamira as also detailed in WO2019/086510. A wheat plant source of the Rf4 restorer allele includes the following lines: R113 or L13.

In specific embodiment, representative alleles of Rf1, Rf3, and Rf4s restorer alleles are provided by the seed sample: NCIMB 43746.

In another specific embodiment, representative alleles of Rf1, Rf3, and 6R restorer alleles are provided by the seed sample: NCIMB 43747.

| NCIMB 43746 | Triticum aestivum/winter wheat | LGWR20-0485 |
| NCIMB 43747 | Triticum aestivum/winter wheat | LGWR17-0160 |

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

As used herein a "marker" refers to a specific DNA sequence identified within the genome of a plant and which can be used to determine whether a plant has inherited a particular phenotype or allele of interest from a parent plant. Said marker may include coding or non-coding sequences. In particular, said marker may include one or more Single Nucleotide Polymorphism or SNP identified within the plant genome.

As used herein, the Rf1 locus refers to the locus of the Rf1 restorer allele, which locus is located at most 10 cM, preferably at most 7 cM, more preferably at most 2 cM, from marker cfn0522096 of SEQ ID NO:3 and/or from marker cfn05277067 of SEQ ID NO:9. In a specific embodiment, the wheat plant restorer of fertility according to the present disclosure includes at least one Rf1 restorer allele, said Rf1 restorer allele being located within the chromosomal interval between SNP markers cfn0522096 of SEQ ID NO:3 and cfn05277067 of SEQ ID NO:9.

In specific embodiments, the wheat plant restorer of fertility includes one Rf1 restorer allele at the Rf1 locus characterized by the presence of one or more of the SNP allele(s) as identified by Table 1.

TABLE 1

SNP markers for mapping of Rf1 locus

| SNP# | Marker Name | Marker SEQ ID NO: | Restorer Allele |
|---|---|---|---|
| SNP1 | cfn0523109 | 1 | A |
| SNP2 | 276I13_96B22_97797 | 2 | C |
| SNP3 | cfn0522096 | 3 | C |
| SNP4 | cfn0527763 | 4 | C |
| SNP5 | 104A4_105172 | 5 | TG |
| SNP6 | 104A4_105588 | 6 | A |
| SNP7 | cfn0373248 | 7 | T |
| SNP8 | cfn1097828 | 8 | C |
| SNP9 | cfn0527067 | 9 | A |
| SNP10 | cfn0528390 | 10 | G |
| SNP11 | BWS0267 | 11 | A |
| SNP12 | cfn0527718 | 12 | T |
| SNP13 | cfn0524469 | 13 | G |
| SNP14 | cfn0524921 | 14 | G |
| SNP15 | cfn1122326 | 15 | C |
| SNP16 | RFL79_S7 | 16 | G |

Preferably, the wheat plant restorer of fertility according to the present disclosure includes one Rf1 restorer allele at the Rf1 locus characterized by the presence of the SNP2 and/or SNP6 and/or SNP16 restorer allele(s) as described in Table 1. Preferably, the wheat plant restorer of fertility is characterized by the haplotypes of the SNP2 and SNP6 restorer alleles "C" and "A". More preferably the RF1 restorer allele at the Rf1 locus is SNP16, characterized by the haplotype of the SNP16 restorer allele "G".

In specific embodiments, the wheat plant restorer of fertility with Rf1 restorer allele comprises a Rf1 nucleic acid.

By "Rf1 nucleic acid", it is meant a nucleic acid comprising a gene encoding a Rf1 protein restorer of fertility of *T. timopheevii* CMS cytoplasm, wherein the corresponding amino acid sequence has at least 95% identity, preferably, 96%, 97%, 98%, 99% or 100% identity to SEQ ID NO:64.

In particular, the inventors have previously identified that RFL79 sequence of SEQ ID NO:64 can restore male fertility of CMS-Fielder plants. Accordingly, in a preferred embodiment, examples of Rf1 nucleic acids comprises the disclosed Rf1 nucleic acid sequences of SEQ ID NO:65, SEQ ID NO:66, SEQ ID NO:67, SEQ ID NO:68 or SEQ ID NO:69, preferably a Rf1 nucleic acid comprises SEQ ID NO:69. In these sequences the inventors have identified the marker RFL79_S7 (SNP16).

As used herein, the Rf3 locus refers to the locus of the Rf3 restorer allele, which locus is at most 10 cM, preferably at most 7 cM, more preferably at most 2 cM, from marker cfn1249269 of SEQ ID NO:19 and/or from marker BS00090770 of SEQ ID NO:42.

In a specific embodiment, the wheat plant restorer of fertility includes at least one Rf3 restorer allele within the Rf3 locus, said Rf3 restorer allele being located within the chromosomal fragment between SNP markers cfn1249269 and BS00090770.

In another specific embodiment, the wheat plant restorer of fertility includes one Rf3 restorer allele at the Rf3 locus characterized by the presence of one or more of the SNP allele(s) as identified by Table 2.

TABLE 2

SNP Markers for mapping of Rf3 locus

| SNP# | Marker Name | Marker SEQ ID | Restorer Allele |
|---|---|---|---|
| SNP17 | cfn1252000 | 17 | A |
| SNP18 | IWB14060* | 18 | G |
| SNP19 | cfn1249269 | 19 | G |
| SNP20 | 219K1_166464 | 20 | T |
| SNP21 | 219K1_158251 | 21 | G |
| SNP22 | 219K1_111446 | 22 | A |
| SNP23 | 219K1_110042 | 23 | T |
| SNP24 | 219K1_110005 | 24 | C |
| SNP25 | 219K1_107461 | 25 | A |
| SNP26 | 219K1_99688 | 26 | T |
| SNP27 | 219K1_37 | 27 | C |
| SNP28 | cfn1270524 | 28 | T |
| SNP29 | 136H5_3M5_7601 | 29 | T |
| SNP30 | cfn1288811 | 30 | G |
| SNP31 | 136H5_3M5_89176 | 31 | A |
| SNP32 | 136H5_3M5_89263 | 32 | T |
| SNP33 | 136H5_3M5_138211 | 33 | T |
| SNP34 | cfn0556874 | 34 | C |
| SNP35 | 136H5_3M5_64154 | 35 | C |
| SNP36 | 136H5_3M5_68807 | 36 | G |
| SNP37 | 136H5_3M5_77916 | 37 | A |
| SNP38 | cfn1246088 | 38 | A |
| SNP39 | cfn1287194 | 39 | G |
| SNP40 | cfn1258380 | 40 | A |
| SNP41 | IWB72107* | 41 | A |
| SNP42 | BS00090770 | 42 | T |
| SNP43 | cfn1239345 | 43 | A |
| SNP44 | RFL29_S2 | 44 | G |
| SNP45 | RFL29_S4 | 45 | C |

Preferably, the wheat plant restorer of fertility according to the present disclosure includes one Rf3 restorer allele at the Rf3 locus characterized by the presence of the SN P29 and/or SNP31 restorer allele(s) as described in Table 2. More preferably, the wheat plant restorer of fertility is characterized by the haplotype of the SNP29 and SNP31 restorer alleles "T" and "A" respectively.

In another particular embodiment, that may be combined with the previous embodiments, the wheat plant restorer of fertility according to the present disclosure includes one Rf3 restorer allele at the Rf3 locus characterized by the presence of the SNP38 and SNP41 restorer alleles "A" and "A" respectively.

As described in WO 2019/086510, two types of Rf3 restorer of fertility exist: one with a strong fertility restoration, and another with a weak fertility restoration. In another preferred specific embodiment, the wheat plant restorer of fertility includes one Rf3 strong restorer allele at the Rf3 locus.

The SNP 44 marker, characterized by the restorer allele "G", is a marker of weak Rf3 restorer of fertility allele, the SNP 41 and 45, characterized by restorer alleles "A" and "C" respectively are marker of strong Rf3 restorer of fertility allele.

More preferably, the wheat plant restorer of fertility according to the present disclosure includes one Rf3 restorer allele at the Rf3 locus characterized by the presence of the SNP41 and/or SNP45 restorer allele(s) as described in Table 2. More preferably, the wheat plant restorer of fertility is characterized by the haplotype of the SNP41 and SNP45 restorer alleles "A" and "C" respectively.

In specific embodiments, the wheat plant restorer of fertility with Rf3 restorer allele comprises a Rf3 nucleic acid.

As used herein, the term "Rf3 nucleic acid" refers to a nucleic acid comprising a gene encoding a Rf3 protein restorer of fertility of T. timopheevii CMS cytoplasm, wherein the corresponding amino acid sequence has at least 95% identity, preferably, 96%, 97%, 98%, 99% or 100% identity to an amino acid sequence selected from the group consisting of SEQ ID NO:70, SEQ ID NO:71 and SEQ ID NO:72.

Typically, the wheat plant restorer of fertility according to the present disclosure includes Rf3 nucleic acids comprises SEQ ID NO:73, SEQ ID NO:74, SEQ ID NO:75, SEQ ID NO:76, SEQ ID NO:77 or SEQ ID NO:78. Markers for fertility restoration can also be found on an extended region around these sequences, by extended regions it is intended 5 kb around these sequences. Examples of marker on the extended regions are RFL29_S2 or RFL29_S4.

The characterization of the genomic region containing Rf4 *Aegilops speltoides* genetic determinants is detailed in Example section below.

As used herein, the Rf4s locus is located between 6 cM and 43 cM from the chromosomal position delimited by the SNP markers TaContig158085_61_BS00011513 of SEQ ID NO:46 and cfn0864865 of SEQ ID NO:47.

Preferably, the Rf4s locus is located between 6 cM and 36 cM from the chromosomal position delimited by the SNP markers EXCALIBUR_C96134_152 of SEQ ID NO:48 and cfn3133296 of SEQ ID NO:49.

In specific embodiment, the wheat plant restorer comprises any *Ae. Speltoides* SNP on the short arm of the chromosome 6B on the area ranging from 0 to 32 334 597 bases according to IWGSC V1 reference, preferably from the area ranging from 0 to 29 782 272 bases according to IWGSC V1 reference.

In specific embodiment, the wheat plant restorer comprises any *Ae. Speltoides* SNP on the short arm of the chromosome 6B and within the chromosomal interval between 0 to 35.77 cM.

In specific embodiment, the wheat plant restorer of fertility includes one Rf4s restorer allele at the Rf4 *Ae. Speltoides* locus characterized by the presence of one or more of the SNP allele(s) as identified by Table 3.

TABLE 3

SNP markers of Rf4s locus

| SNP# | Marker Name | Marker SEQ ID | Restorer Allele |
|---|---|---|---|
| SNP46 | TaContig158085_61_BS00011513 | 46 | T |
| SNP47 | cfn0864865 | 47 | G |
| SNP48 | EXCALIBUR_C96134_152 | 48 | C |
| SNP49 | cfn3133296 | 49 | G |
| SNP50 | LWE1_chr6B_485210_Rf4S | 50 | T |
| SNP51 | LWE1_chr6B_11287944_Rf4S | 51 | G |
| SNP52 | LWE1_chr6B_19775886_Rf4S | 52 | G |
| SNP53 | LWE1_chr6B_28157776_Rf4S | 53 | C |

Preferably, the wheat plant restorer of fertility according to the present disclosure includes one Rf4s restorer allele at the Rf4 locus characterized by the presence of the SNP53 restorer allele as described in Table 3. More preferably, the wheat plant restorer of fertility is characterized by the haplotype of the SNP53 restorer allele "C".

As used herein, the Rf7 locus is located at most 10 cM from marker cfn0919993 of SEQ ID NO:55. In specific embodiment, the wheat plant restorer of fertility includes one Rf7 restorer allele at the Rf7 locus characterized by the presence of one or more of the SNP allele(s) as identified by Table 4:

TABLE 4

SNP markers of Rf7 locus

| SNP# | Marker Name | Marker SEQ ID | Restorer Allele |
|---|---|---|---|
| SNP54 | cfn0917304 | 54 | T |
| SNP55 | cfn0919993 | 55 | G |
| SNP56 | cfn0920459 | 56 | C |
| SNP57 | cfn0915987 | 57 | G |
| SNP58 | cfn0920253 | 58 | A |
| SNP59 | cfn0448874 | 59 | T |
| SNP60 | cfn0923814 | 60 | C |
| SNP61 | cfn0924180 | 61 | G |
| SNP62 | cfn0919484 | 62 | G |
| SNP64 | LWE1_chr7B_658281643_Rf7 | 263 | G |
| SNP65 | LWE1_chr7B_711539100_Rf7 | 264 | A |

Preferably, the wheat plant restorer of fertility according to the present disclosure includes one Rf7 restorer allele at the Rf7 locus characterized by the presence of one or more SNP restorer allele(s) chosen among SNP54-62 and SNP64-65 of "restorer allele" haplotype, as described in Table 4.

More preferably, the wheat plant restorer of fertility according to the present disclosure includes one Rf7 restorer allele at the Rf7 locus characterized by the presence of the SNP64 restorer allele and/or the SNP65 restorer allele as described in Table 4. More preferably, the wheat plant restorer of fertility is characterized by the haplotype of the SNP64 and SNP65 restorer alleles "G" and "A" respectively.

In specific embodiments, the wheat plant restorer of fertility with Rf7 restorer allele comprises a Rf7 nucleic acid.

As used herein, the term "Rf7 nucleic acid" refers to a nucleic acid comprising a gene encoding a Rf7 protein restorer of fertility of *T. timopheevii* CMS cytoplasm, wherein the corresponding amino acid sequence has at least 95% identity, preferably, 96%, 97%, 98%, 99% or 100% identity to an amino acid sequence selected from the group consisting of SEQ ID NO:79, SEQ ID NO:80 and SEQ ID NO:81.

As used herein, the 6R locus corresponds to the rye introgression T4BS.4BL-6RL from TA5031 line as detailed in Example section. Particularly, the 6R locus is located on chromosome 6R and within the chromosomal interval between 48.9 cM to 114.8 cM (end of the chromosome).

In specific embodiment, the wheat plant restorer of fertility includes the 6R restorer allele at the 6R locus characterized by the presence of the SNP allele as identified by Table 5:

TABLE 5

SNP marker of 6R locus

| SNP# | Marker Name | Marker SEQ ID | Restorer Allele |
|---|---|---|---|
| SNP63 | RFL46_52 | 63 | A |

In a particular embodiment, the wheat plant restorer of fertility of *T. timopheevii* CMS cytoplasm comprises Rf1, Rf3, Rf4s restorer allele.

In particular, it is hereby included a wheat plant comprising Rf1, Rf3 and Rf4s restorer alleles as provided by the seed samples as deposited on Mar. 22, 2021, under deposit number NCIMB 43746 at the NCIMB collection.

In another particular embodiment, the wheat plant restorer of fertility of *T. timopheevii* CMS cytoplasm comprises Rf1, Rf3, and 6R restorer allele. In particular, it is hereby included a wheat plant comprising Rf1, Rf3 and 6R restorer alleles as provided by the seed samples as deposited on Mar. 22, 2021, under deposit number NCIMB 43747 at the NCIMB collection.

The disclosure also relates to hybrid wheat plants which can be produced by crossing a wheat plant restorer of fertility according to the present disclosure as described above with a second plant.

In certain embodiments, the wheat plant according to the disclosure is alloplasmic and comprises the *T. timopheevii* cytoplasm.

For example, a hybrid wheat plant may be obtained by crossing a wheat plant restorer of fertility according to the present disclosure as described above, for example comprising Rf1, Rf3 and Rf4s restorer alleles or Rf1, Rf3 and 6R restorer alleles, and a wheat plant which does not have said fertility restorer alleles.

It is also disclosed herein a method for producing a wheat hybrid plant comprising the steps of:
  a. crossing a sterile female wheat plant comprising the *T. timopheevii* cytoplasm with a fertile male wheat plant of the present disclosure as described above;
  b. collecting the hybrid seed;
  c. optionally detecting the presence of *T. timopheevii* cytoplasm, and/or the fertility restorer alleles A, B and C as defined above in the hybrid seed;
  d. optionally detecting hybridity level of the hybrid seed.

In specific embodiment, step c) comprises the detection of Rf1, Rf3, and Rf4s restorer alleles. According to this embodiment, step c) may optionally further comprise the detection of Rf7 or 6R restorer alleles.

In specific embodiment, step c) comprises the detection of Rf1, Rf3 and 6R restorer alleles.

Therefore, it is also disclosed herein the wheat plants or lines according to the present disclosure developed to obtain such hybrid plants. Such plants or lines typically comprise the cytoplasmic elements necessary for the implementation of the corresponding hybrid system. Preferably, the plants or lines comprise the fertility restorer alleles Rf1, Rf3, Rf4s and *T. timopheevii* cytoplasm, or Rf1, Rf3, 6R and *T. timopheevii* cytoplasm, or Rf3, Rf7, Rf4s and *T. timopheevii* cytoplasm, or also Rf3, Rf7, 6R and *T. timopheevii* cytoplasm.

Alternatively, the detection of the presence of *T. timopheevii* cytoplasm and the restorer alleles (step "c" of the method described above) can be performed on the parent lines in order to check their genotype before to start the cross (step "a") or at every step of their increase.

The T-CMS cytoplasm can be detected either phenotypically wherein a plant bearing rf genes and a T-CMS cytoplasm will be sterile or by molecular means able to detect the orf256 gene as described in Rathburn and Hedgcoth, 1991 and Song and Hedgcoth, 1994.

Method of Producing and Selecting a Wheat Plant of the Disclosure

The present disclosure also relates to the methods to produce the wheat plant with the fertility restorer alleles as described in the previous section.

In one embodiment, the method for producing the wheat plant restorer of fertility comprises the following steps:
  a. providing a first wheat plant comprising one or two restorer allele selected among fertility restorer alleles A, B and C as defined above,
  b. crossing said first wheat plant with a second wheat plant comprising one or two restorer alleles selected among fertility restorer alleles A, B and C, wherein A, B and C restorer alleles are represented at least once in the panel of restorer alleles provided by the first plant and the second plant, c. collecting the F1 hybrid seed, d. obtaining homozygous plants from the F1 plants, and e. detecting the presence of the fertility restorer alleles A, B and C in the hybrid seed and/or at each generation.

The fertility restorer alleles A, B and C are as previously defined.

In specific embodiments, the fertility restorer allele A is Rf3, the fertility restorer allele B is Rf1, and the fertility restorer allele C is Rf4s.

In specific embodiments, the fertility restorer allele A is Rf3, the fertility restorer allele B is Rf1, and the fertility restorer allele C is 6R.

In specific embodiments, the fertility restorer allele A is Rf3, the fertility restorer allele B is Rf7, and the fertility restorer allele C is Rf4s.

In specific embodiments, the fertility restorer allele A is Rf3, the fertility restorer allele B is Rf7, and the fertility restorer allele C is 6R.

Preferentially, the female plant in step b) is bearing the T-CMS cytoplasm. In this case, the presence of the restorer alleles is assessed at every generation from step b) to step d) by using the markers on the present disclosure and/or by assessing the fertility level.

According to this embodiment, the method may further comprise the detection of Rf1, Rf3, Rf4s, Rf7 and/or 6R restorer alleles in the hybrid seed and/or at each generation.

In another embodiment, the method for producing the wheat plant restorer of fertility comprises the following steps:

a. providing a first wheat plant comprising at least fertility restorer alleles A, B and C as defined above, b. crossing said first wheat plant with a second wheat plant, c. collecting the F1 hybrid seed, and d. obtaining homozygous plants from the F1 plants.

In a variant of this embodiment, the method may comprise the detection of the presence of the Rf1, Rf3 and Rf4s restorer alleles in the hybrid seed and/or at each generation.

In another variant of this embodiment, the method may comprise the detection of the presence of the Rf1, Rf3 and Rf4s restorer alleles in the hybrid seed and/or at each generation.

In another variant of this embodiment, the method may comprise the detection of the presence of the Rf1, Rf3 and 6R restorer alleles in the hybrid seed and/or at each generation In another variant of this embodiment, the method may comprise the detection of the presence of the Rf1, Rf7 and Rf4s restorer alleles in the hybrid seed and/or at each generation In another variant of this embodiment, the method may comprise the detection of the presence of the Rf1, Rf7 and 6R restorer alleles in the hybrid seed and/or at each generation.

In another embodiment, the method for producing the wheat plant restorer of fertility comprises the following steps:

a. crossing a first wheat plant having at least the fertility restorer alleles A, B, and C as defined above with a second wheat plant, thereby obtaining a F1 hybrid plant;

b. backcrossing said F1 hybrid with the second wheat plant;

c. selecting the wheat plant restorer of fertility among the wheat plant obtained in step b) by detecting the presence of at the fertility restorer alleles.

According to this embodiment, the method may optionally comprise a step d) of self-crossing the wheat plant to obtain plants homozygous for the restorer fertility alleles A, B, and C.

According to this embodiment, the method may also further comprise one or more step of backcrossing the selected wheat plant by detecting the presence of the restorer alleles initially present in the wheat plant provided at step a).

In a preferred variant of this embodiment, the second wheat plant which is crossed with the first wheat plant having the fertility restorer alleles A, B and C, is an elite wheat line.

Method to generate homozygous plants are generally well known from skilled person of the art. This could be either by repetitive backcross, by double haploid development or by Single Seeds Descent (SSD) methods.

The applicant has deposited a sample of seeds of the disclosed wheat plant with said Rf1, Rf3 and Rf4s restorer alleles, on Mar. 11, 2021, under the Budapest treaty, at NCIMB collection under the number NCIMB 43746, and with said Rf1, Rf3 and 6R restorer alleles, on Mar. 11, 2021, under the Budapest treaty, at NCIMB collection under the number NCIMB 43747.

Methods of Identifying the Wheat Plant Restorer of Fertility of the Disclosure

The present disclosure further includes and provides methods of identifying the respective Rf1, Rf3, Rf4s, Rf7 and/or 6R restorer alleles as disclosed in the previous sections, and more generally methods of selecting or breeding wheat plants for the presence or absence of the Rf1, Rf3, Rf4s, Rf7 and/or 6R fertility restorer alleles. Such methods of identifying, selecting or breeding wheat plants comprise obtaining one or more wheat plants and assessing their DNA to determine the presence or absence of the Rf1, Rf3, Rf4s, Rf7 and/or 6R fertility restorer alleles contained in the respective locus.

Such methods may be used, for example, to determine which progeny resulting from a cross have the required combination of fertility restorer alleles and accordingly to guide the preparation of plants having the required combination in combination with the presence or absence of other desirable traits.

Accordingly, plants can be identified or selected by assessing them for the presence of one or more individual SNPs appearing in the above Tables 1 to 5, as well as the SNPs in Table 7, for assessing the presence of restorer alleles Rf1, Rf3, Rf4s, Rf7 and/or 6R.

In a specific embodiment, the wheat plant may be identified or selected by assessing the presence of one or more individual SNPs appearing in the above Tables 1 to 3, as well as the SNPs in Table 7, for assessing the presence of restorer alleles Rf1, Rf3, and Rf4s.

In a specific embodiment, the wheat plant may be identified or selected by assessing the presence of one or more individual SNPs appearing in the above Tables 1, 2 and 5, as well as the SNPs in Table 7, for assessing the presence of restorer alleles Rf1, Rf3, and 6R.

In a specific embodiment, the wheat plant may be identified or selected by assessing the presence of one or more individual SNPs appearing in the above Tables 1, 3 and 4, as well as the SNPs in Table 7, for assessing the presence of restorer alleles Rf1, Rf7, and Rf4s.

In a specific embodiment, the wheat plant may be identified or selected by assessing the presence of one or more individual SNPs appearing in the above Tables 1, 4 and 5, as well as the SNPs in Table 7, for assessing the presence of restorer alleles Rf1, Rf7, and 6R.

In a specific embodiment, the wheat plant may be identified or selected by assessing the presence of one or more individual SNPs appearing in the above Tables 1 to 4, as well as the SNPs in Table 7, for assessing the presence of restorer alleles Rf1, Rf3, Rf4s and Rf7.

In a specific embodiment, the wheat plant may be identified or selected by assessing the presence of one or more individual SNPs appearing in the above Tables 1 to 3 and 5, as well as the SNPs in Table 7, for assessing the presence of restorer alleles Rf1, Rf3, Rf4s and 6R.

In a specific embodiment, the wheat plant may be identified or selected by assessing the presence of one or more individual SNPs appearing in the above Tables 1, 4 and 5, as well as the SNPs in Table 7, for assessing the presence of restorer alleles Rf1, Rf3, Rf7 and 6R.

More generally, it is disclosed herein the specific means for detecting the restorer alleles in a wheat plant, more specifically Rf1, Rf3, Rf4s, Rf7 and 6R restorer alleles and their combinations.

Said means thus include any means suitable for detecting the following SNP markers within one or more of the following markers: SEQ ID NOs 1-65.

Any method known in the art may be used in the art to assess the presence or absence of a SNP. Some suitable methods include, but are not limited to, sequencing, hybridization assays, polymerase chain reaction (PCR), ligase chain reaction (LCR), and genotyping-by-sequence (GBS), or combinations thereof.

Different PCR based methods are available to the person skilled of the art. One can use the RT-PCR method or the Kaspar method from KBioscience (LGC Group, Teddington, Middlesex, UK).

The KASP™ genotyping system uses three target specific primers: two primers, each of them being specific of each allelic form of the SNP (Single Nucleotide Polymorphism) and one other primer to achieve reverse amplification, which is shared by both allelic form. Each target specific primer also presents a tail sequence that corresponds with one of two FRET probes: one label with FAM® dye and the other with HEX® dye.

Successive PCR reactions are performed. The nature of the emitted fluorescence is used to identify the allelic form or forms present in the mix from the studied DNA.

The primers identified in Table 6 are particularly suitable for use with the KASP™ genotyping system. Of course, the skilled person may use variant primers or nucleic acid probes of the primers as identified in Table 6, said variant primers or nucleic acid probes having at least 90%, and preferably 95% sequence identity with any one of the primers as identified in Table 6, or with the DNA genomic fragment amplified by the corresponding set of primers as identified in Table 6.

Percentage of sequence identity as used herein is determined by calculating the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. For example, nucleic acid sequences may be aligned using the BLAST 2 sequences (Bl2seq) using BLASTN algorithms (www.ncbi.nlm.nih.gov).

As used herein, a primer encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form though single-stranded form is preferred. Alternatively, nucleic acid probe can be used. Nucleic acid probe encompasses any nucleic acid of at least 30 nucleotides and which can specifically hybridizes under standard stringent conditions with a defined nucleic acid. Standard stringent conditions as used herein refers to conditions for hybridization described for example in Sambrook et al 1989 which can comprise 1) immobilizing plant genomic DNA fragments or library DNA on a filter 2) prehybridizing the filter for 1 to 2 hours at 65° C. in 6×SSC 5×Denhardt's reagent, 0.5% SDS and 20 mg/ml denatured carrier DNA 3) adding the probe (labeled) 4) incubating for 16 to 24 hours 5) washing the filter once for 30 min at 68° C. in 6×SSC, 0.1% SDS 6) washing the filter three times (two times for 30 min in 30 ml and once for 10 min in 500 ml) at 68° C. in 2×SSC 0.1% SDS.

In specific embodiments, said primers for detecting the SNP markers of the present disclosure (specific for each allele "X" or "Y" or common) are as listed in the following Table 6:

TABLE 6

Primers for use in detecting fertility restorer SNP markers of the invention (as indicated in the primer name)

| SEQ ID NO: | MARKER NAME | Sequence |
|---|---|---|
| 82 | cfn0523109 Allele X | GAAGGTGACCAAGTTCATGCTGGTGAACAAAACAGGCCTACAATCA |
| 83 | 276I13_96B22_97797 Allele X | GAAGGTGACCAAGTTCATGCTGTACTATGGCTATGTCTCTGAATGC |
| 84 | cfn0522096 Allele X | GAAGGTGACCAAGTTCATGCTAGTAGAATACCACCCAATAAATCACTG |
| 85 | cfn0527763 Allele X | GAAGGTGACCAAGTTCATGCTATCTAGCCACGCAAATGCCCGT |
| 86 | 104A4_105172 Allele X | GAAGGTGACCAAGTTCATGCTGTCGMACCCAATGAATAATGTTT |

TABLE 6-continued

Primers for use in detecting fertility restorer SNP markers of the invention (as indicated in the primer name)

| SEQ ID NO: | MARKER NAME | Sequence |
|---|---|---|
| 87 | 104A4_105588 Allele X | GAAGGTGACCAAGTTCATGCTGTTCCTTGTGACATGTACT CATAA |
| 88 | cfn0373248 Allele X | GAAGGTGACCAAGTTCATGCTAACAACAATTAYGAGGATC AAATGGTCA |
| 89 | cfn1097828 Allele X | GAAGGTGACCAAGTTCATGCTGGTTCCTGAGAGAGCAAC CA |
| 90 | cfn0527067 Allele X | GAAGGTGACCAAGTTCATGCTCAAATTACTTTTGTTCTTTT ATTTTTTTCGAAT |
| 91 | cfn0528390 Allele X | GAAGGTGACCAAGTTCATGCTAAAAACATCTATTCCAAGC AAGTATTAGTAAT |
| 92 | BWS0267 Allele X | GAAGGTGACCAAGTTCATGCTTCAGCTGCATAAAAAMCA GAATACCA |
| 93 | cfn0527718 Allele X | GAAGGTGACCAAGTTCATGCTAATTGTTCACAACATGGAC ATGAGAAC |
| 94 | cfn0524469 Allele X | GAAGGTGACCAAGTTCATGCTTCAGCTGCATAAAAAMCA GAATACCA |
| 95 | cfn0524921 Allele X | GAAGGTGACCAAGTTCATGCTATTGTTTCCATGTTAAGCT TATATTGTGCA |
| 96 | cfn1122326 Allele X | GAAGGTGACCAAGTTCATGCTGAATCTGATTAAGACGCT GGAGAAC |
| 97 | RFL79_S7 Allele X | GAAGGTGACCAAGTTCATGCTAAGCTTGATAAGGCTATG CTTATATTTAG |
| 98 | cfn1252000 Allele X | GAAGGTGACCAAGTTCATGCTGTTAATGCTGTAGCCATTC TTGCAA |
| 99 | IWB14060* Allele X | GAAGGTGACCAAGTTCATGCTCATTCGACGCGTCTTCCG CAATA |
| 100 | cfn1249269 Allele X | GAAGGTGACCAAGTTCATGCTGATTCAAAGAGGTGACAA ATATGTGTACT |
| 101 | 219K1_166464 Allele X | GAAGGTGACCAAGTTCATGCTCCTGAGCTGGGCTGCACC |
| 102 | 219K1_158251 Allele X | GAAGGTGACCAAGTTCATGCTCCTGGAGATGGATCCGGT CAG |
| 103 | 219K1_111446 Allele X | GAAGGTGACCAAGTTCATGCTAGAATCGTTCTTCGAGAA GCACTCA |
| 104 | 219K1_110042 Allele X | GAAGGTGACCAAGTTCATGCTACGGAATCGAGTCAACCA ATTCCT |
| 105 | 219K1_110005 Allele X | GAAGGTGACCAAGTTCATGCTGCCTTTTCTTCTTCCAGCA TCTAC |
| 106 | 219K1_107461 Allele X | GAAGGTGACCAAGTTCATGCTATATTGTTTGTATTAAAAA GTTGTGTGTTTTGA |
| 107 | 219K1_99688 Allele X | GAAGGTGACCAAGTTCATGCTGTTGCCCTGCGCAAAATC AAACTT |
| 108 | 219K1_37 Allele X | GAAGGTGACCAAGTTCATGCTAAAGGGCTATCCTGGTGA ACAAC |
| 109 | cfn1270524 Allele X | GAAGGTGACCAAGTTCATGCTAAATGCCTAGTCTATACCT GATAAACTAAA |
| 110 | 136H5_3M5_7601 Allele X | GAAGGTGACCAAGTTCATGCTCGTCCCCCATGGCACCTGT |
| 111 | cfn1288811 Allele X | GAAGGTGACCAAGTTCATGCTTAATTTGGTTAACCAAATC CTTTTTGATTTTT |

TABLE 6-continued

Primers for use in detecting fertility restorer SNP markers of the invention (as indicated in the primer name)

| SEQ ID NO: | MARKER NAME | Sequence |
|---|---|---|
| 112 | 136H5_3M5_89176 Allele X | GAAGGTGACCAAGTTCATGCTGGATTTTCTCACCGGCATCTCCA |
| 113 | 136H5_3M5_89263 Allele X | GAAGGTGACCAAGTTCATGCTTCCCATGTTCTTTTTTGCTCAAAAC |
| 114 | 136H5_3M5_138211 Allele X | GAAGGTGACCAAGTTCATGCTACTGGGTGCAAAGCCAAGATGATT |
| 115 | cfn0556874 Allele X | GAAGGTGACCAAGTTCATGCTAAAGAGCATGTCAGACACAATGCAG |
| 116 | 136H5_3M5_64154 Allele X | GAAGGTGACCAAGTTCATGCTGGCGAAACTTCGCCGCGATAAAT |
| 117 | 136H5_3M5_68807 Allele X | GAAGGTGACCAAGTTCATGCTCAAGTTGCTCTTAATTATCTGTGCGTA |
| 118 | 136H5_3M5_77916 Allele X | GAAGGTGACCAAGTTCATGCTATAGCAAGTAGAGTTAACTTATCAAGTTATTA |
| 119 | cfn1246088 Allele X | GAAGGTGACCAAGTTCATGCTGACATCTGATGAGCCAGCATACA |
| 120 | cfn1287194 Allele X | GAAGGTGACCAAGTTCATGCTACCTCCTCCGTATCTGATGGC |
| 121 | cfn1258380 Allele X | GAAGGTGACCAAGTTCATGCTATCTACTCATCTATTGCAGATGCTCTT |
| 122 | IWB72107* Allele X | GAAGGTGACCAAGTTCATGCTGATGACATGGAGGATTATATCGACGA |
| 123 | BS00090770 Allele X | GAAGGTGACCAAGTTCATGCTGGTCGTAGCACATAGCCGTTTAC |
| 124 | cfn1239345 Allele X | GAAGGTGACCAAGTTCATGCTGGCTTCTTTTTTCTCCCTATAATATGGA |
| 125 | RFL29_S2 Allele X | GAAGGTGACCAAGTTCATGCTCGGGCAACTCTCTTCTTCTTAATCAA |
| 126 | RFL29_S4 Allele X | GAAGGTGACCAAGTTCATGCTATGATGACTCCATGAGGGTGGC |
| 127 | cfn0917304 Allele X | GAAGGTGACCAAGTTCATGCTGTGGTGGCGCTCTACCCG |
| 128 | cfn0919993 Allele X | GAAGGTGACCAAGTTCATGCTAAGTCATCGACTTACATGCTTCTTTG |
| 129 | cfn0920459 Allele X | GAAGGTGACCAAGTTCATGCTAGCCAAGGAAGCCCAGATTTTC |
| 130 | cfn0915987 Allele X | GAAGGTGACCAAGTTCATGCTAGATCATTACCCAACGGCCAATG |
| 131 | cfn0920253 Allele X | GAAGGTGACCAAGTTCATGCTGGTCATCCAAACATTTACATCGTTA |
| 132 | cfn0448874 Allele X | GAAGGTGACCAAGTTCATGCTCTTTGTTTCTAAATAGCTGCGGCC |
| 133 | cfn0923814 Allele X | GAAGGTGACCAAGTTCATGCTCCAAGTCGCAAATGTAAGGTCAGA |
| 134 | cfn0924180 Allele X | GAAGGTGACCAAGTTCATGCTTCCTCTTTTCATCATGCACCATTA |
| 135 | cfn0919484 Allele X | GAAGGTGACCAAGTTCATGCTAAATGCAAGTGGCGAATCTTATCTCTA |
| 136 | Excalibur_c96134_152 Allele X | GAAGGTGACCAAGTTCATGCTACTCTGGTGACACCATGTAACTTC |

TABLE 6-continued

Primers for use in detecting fertility restorer SNP markers of the invention (as indicated in the primer name)

| SEQ ID NO: | MARKER NAME | Sequence |
|---|---|---|
| 137 | cfn3133296 Allele X | GAAGGTGACCAAGTTCATGCTCCAAGTGTCCCTCCTTGAGTCA |
| 138 | LWE1_chr6B_485210_Rf4S Allele X | GAAGGTGACCAAGTTCATGCTCATACTTGTAGAGATCGTCACCC |
| 139 | LWE1_chr6B_11287944_Rf4S Allele X | GAAGGTGACCAAGTTCATGCTCTTCTGTTTAGGACTACACATCAACT |
| 140 | LWE1_chr6B_19775886_Rf4S Allele X | GAAGGTGACCAAGTTCATGCTAAGGGCGCCGGCACTGGT |
| 141 | LWE1_chr6B_28157776_Rf4S Allele X | GAAGGTGACCAAGTTCATGCTTTAGAAACGATCTGCTTACTGATTACTAT |
| 142 | RFL46_S2 Allele X | GAAGGTGACCAAGTTCATGCTGGCCAGAGCTATGGACAAAGCAA |
| 143 | cfn0523109 Allele Y | GAAGGTCGGAGTCAACGGATTGTGAACAAAACAGGCCTACAATCC |
| 144 | 276I13_96B22_97797 Allele Y | GAAGGTCGGAGTCAACGGATTAAGTACTATGGCTATGTCTCTGAATGT |
| 145 | cfn0522096 Allele Y | GAAGGTCGGAGTCAACGGATTAGTAGAATACCACCCAATAAATCACTC |
| 146 | cfn0527763 Allele Y | GAAGGTCGGAGTCAACGGATTCTAGCCACGCAAATGCCCGC |
| 147 | 104A4_105172 Allele Y | GAAGGTCGGAGTCAACGGATTCTGTCGMACCCAATGAATAATGTTC |
| 148 | 104A4_105588 Allele Y | GAAGGTCGGAGTCAACGGATTGTTCCTTGTGACATGTACTCATAC |
| 149 | cfn0373248 Allele Y | GAAGGTCGGAGTCAACGGATTAACAACAATTAYGAGGATCAAATGGTCT |
| 150 | cfn1097828 Allele Y | GAAGGTCGGAGTCAACGGATTGGTTCCTGAGAGAGCAACCG |
| 151 | cfn0527067 Allele Y | GAAGGTCGGAGTCAACGGATTCAAATTACTTTTGTTCTTTTATTTTTTTCGAAC |
| 152 | cfn0528390 Allele Y | GAAGGTCGGAGTCAACGGATTAAACATCTATTCCAAGCAAGTATTAGTAAC |
| 153 | BWS0267 Allele Y | GAAGGTCGGAGTCAACGGATTCAGCTGCATAAAAAMCAGAATACCG |
| 154 | cfn0527718 Allele Y | GAAGGTCGGAGTCAACGGATTATAAATTGTTCACAACATGGACATGAGAAT |
| 155 | cfn0524469 Allele Y | GAAGGTCGGAGTCAACGGATTGCACGTAGTAAGTATTGATTTTTCTGTT |
| 156 | cfn0524921 Allele Y | GAAGGTCGGAGTCAACGGATTGTTTCCATGTTAAGCTTATATTGTGCG |
| 157 | cfn1122326 Allele Y | GAAGGTCGGAGTCAACGGATTGGAATCTGATTAAGACGCTGGAGAAT |
| 158 | RFL79_S7 Allele Y | GAAGGTCGGAGTCAACGGATTGAAGCTTGATAAGGCTATGCTTATATTTAA |
| 159 | cfn1252000 Allele Y | GAAGGTCGGAGTCAACGGATTGTTAATGCTGTAGCCATTCTTGCAG |
| 160 | IWB14060* Allele Y | GAAGGTCGGAGTCAACGGATTCGACGCGTCTTCCGCAATG |

TABLE 6-continued

Primers for use in detecting fertility restorer SNP markers of the invention (as indicated in the primer name)

| SEQ ID NO: | MARKER NAME | Sequence |
|---|---|---|
| 161 | cfn1249269 Allele Y | GAAGGTCGGAGTCAACGGATTCAAAGAGGTGACAAATATGTGTACC |
| 162 | 219K1_166464 Allele Y | GAAGGTCGGAGTCAACGGATTGCCTGAGCTGGGCTGCACT |
| 163 | 219K1_158251 Allele Y | GAAGGTCGGAGTCAACGGATTCCTGGAGATGGATCCGGTCAA |
| 164 | 219K1_111446 Allele Y | GAAGGTCGGAGTCAACGGATTAATCGTTCTTCGAGAAGCACTCC |
| 165 | 219K1_110042 Allele Y | GAAGGTCGGAGTCAACGGATTCGGAATCGAGTCAACCAATTCCC |
| 166 | 219K1_110005 Allele Y | GAAGGTCGGAGTCAACGGATTCGCCTTTTCTTCTTCCAGCATCTAT |
| 167 | 219K1_107461 Allele Y | GAAGGTCGGAGTCAACGGATTATATTGTTTGTATTAAAAAGTTGTGTGTTTTGC |
| 168 | 219K1_99688 Allele Y | GAAGGTCGGAGTCAACGGATTGCCCTGCGCAAAATCAAACTC |
| 169 | 219K1_37 Allele Y | GAAGGTCGGAGTCAACGGATTACAAAGGGCTATCCTGGTGAACAAT |
| 170 | cfn1270524 Allele Y | GAAGGTCGGAGTCAACGGATTAAATGCCTAGTCTATACCTGATAAACTAAT |
| 171 | 136H5_3M5_7601 Allele Y | GAAGGTCGGAGTCAACGGATTGTCCCCATGGCACCTGC |
| 172 | cfn1288811 Allele Y | GAAGGTCGGAGTCAACGGATTAATTTGGTTAACCAAATCCTTTTTGATTTTG |
| 173 | 136H5_3M5_89176 Allele Y | GAAGGTCGGAGTCAACGGATTTTCTCACCGGCATCTCCG |
| 174 | 136H5_3M5_89263 Allele Y | GAAGGTCGGAGTCAACGGATTCTTCCCATGTTCTTTTTTTGCTCAAAAT |
| 175 | 136H5_3M5_138211 Allele Y | GAAGGTCGGAGTCAACGGATTACTGGGTGCAAAGCCAAGATGATA |
| 176 | cfn0556874 Allele Y | GAAGGTCGGAGTCAACGGATTGAAAGAGCATGTCAGACACAATGCAA |
| 177 | 136H5_3M5_64154 Allele Y | GAAGGTCGGAGTCAACGGATTGCGAAACTTCGCCGCGATAAAC |
| 178 | 136H5_3M5_68807 Allele Y | GAAGGTCGGAGTCAACGGATTAAGTTGCTCTTAATTATCTGTGCGTG |
| 179 | 136H5_3M5_77916 Allele Y | GAAGGTCGGAGTCAACGGATTAGCAAGTAGAGTTAACTTATCAAGTTATTG |
| 180 | cfn1246088 Allele Y | GAAGGTCGGAGTCAACGGATTGACATCTGATGAGCCAGCATACC |
| 181 | cfn1287194 Allele Y | GAAGGTCGGAGTCAACGGATTCACCTCCTCCGTATCTGATGGT |
| 182 | cfn1258380 Allele Y | GAAGGTCGGAGTCAACGGATTCTACTCATCTATTGCAGATGCTCTG |
| 183 | IWB72107* Allele Y | GAAGGTCGGAGTCAACGGATTATGACATGGAGGATTATATCGACGG |
| 184 | BS00090770 Allele Y | GAAGGTCGGAGTCAACGGATTAGGTCGTAGCACATAGCCGTTTAT |
| 185 | cfn1239345 Allele Y | GAAGGTCGGAGTCAACGGATTGCTTCTTTTTTCTCCCTATAATATGGG |

TABLE 6-continued

Primers for use in detecting fertility restorer SNP markers of the invention (as indicated in the primer name)

| SEQ ID NO: | MARKER NAME | Sequence |
|---|---|---|
| 186 | RFL29_S2 Allele Y | GAAGGTCGGAGTCAACGGATTGGGCAACTCTCTTCTTCT TAATCAG |
| 187 | RFL29_S4 Allele Y | GAAGGTCGGAGTCAACGGATTAATGATGACTCCATGAGG GTGGT |
| 188 | cfn0920459 Allele Y | GAAGGTCGGAGTCAACGGATTAGCCAAGGAAGCCCAGAT TTTG |
| 189 | cfn0915987 Allele Y | GAAGGTCGGAGTCAACGGATTCAGATCATTACCCAACGG CCAATT |
| 190 | cfn0920253 Allele Y | GAAGGTCGGAGTCAACGGATTGGTCATCCAAACATTTAC ATCGTTC |
| 191 | cfn0448874 Allele Y | GAAGGTCGGAGTCAACGGATTCTCTTTGTTTCTAAATAGC TGCGGCT |
| 192 | cfn0923814 Allele Y | GAAGGTCGGAGTCAACGGATTCAAGTCGCAAATGTAAGG TCAGC |
| 193 | cfn0924180 Allele Y | GAAGGTCGGAGTCAACGGATTCTTCCTCTTTTCATCATGC ACCATTG |
| 194 | cfn0919484 Allele Y | GAAGGTCGGAGTCAACGGATTATGCAAGTGGCGAATCTT ATCTCTG |
| 195 | Excalibur_c96134_152 Allele Y | GAAGGTCGGAGTCAACGGATTGACTCTGGTGACACCATG TAACTTT |
| 196 | cfn3133296 Allele Y | GAAGGTCGGAGTCAACGGATTCAAGTGTCCCTCCTTGAG TCG |
| 197 | LWE1_chr6B_485210_Rf4S Allele Y | GAAGGTCGGAGTCAACGGATTGTCATACTTGTAGAGATC GTCACCA |
| 198 | LWE1_chr6B_11287944_Rf4S Allele Y | GAAGGTCGGAGTCAACGGATTCTTCTGTTTAGGACTACA CATCAACC |
| 199 | LWE1_chr6B_19775886_Rf4S Allele Y | GAAGGTCGGAGTCAACGGATTAGGGCGCCGGCACTGGC |
| 200 | LWE1_chr6B_28157776_Rf4S Allele Y | GAAGGTCGGAGTCAACGGATTAGAAACGATCTGCTTACT GATTACTAG |
| 201 | RFL46_S2 Allele Y | GAAGGTCGGAGTCAACGGATTGCCAGAGCTATGGACAAA GCAG |
| 202 | cfn0523109 Common | GTGTGTGCTAATGTGGATATACGTAAGTT |
| 203 | 276I13_96B22_97797 Common | ACGACAATATAGACAAATAAAACCAAACAA |
| 204 | cfn0522096 Common | AAGTAGTACTCGTAGAGAGTTAACACAGA |
| 205 | cfn0527763 Common | CCTTGTCCACCGAGACATGTACAAA |
| 206 | 104A4_105172 Common | GCCATCCTCTCGGAGCCAGAA |
| 207 | 104A4_105588 Common | CAAGGATGGGGAGTATATGGCTCTT |
| 208 | cfn0373248 Common | ATCATTGCCACGRAAAAAATCTCACAAGAT |
| 209 | cfn1097828 Common | GCTTCCTCTCGGTAGCGATGGAT |
| 210 | cfn0527067 Common | ATATGATTCACCCTAGATCCTTCACCTTA |
| 211 | cfn0528390 Common | AATAACTCTTGTACTTCAGGATGAACGTTT |
| 212 | BWS0267 Common | CTGCGTTAAGGTTCAGGCAACTGAT |
| 213 | cfn0527718 Common | GTTTCCTCCAATGTTCTTCCC |
| 214 | cfn0524469 Common | GCCAATTTTCAAATCTAAGTCCACAGAGA |

TABLE 6-continued

Primers for use in detecting fertility restorer SNP markers of the invention (as indicated in the primer name)

| SEQ ID NO: | MARKER NAME | Sequence |
|---|---|---|
| 215 | cfn0524921 Common | GCCCTTTGGTAATTCCATTTCAATCTTTT |
| 216 | cfn1122326 Common | CAGATGGCCTAGTCGTGACATATCTT |
| 217 | RFL79_S7 Allele Common | CTCACTCCTTGTTTCTGCATATCT |
| 218 | cfn1252000 Common | GTGCCCATAAGACGACTGGGACAA |
| 219 | IWB14060* Common | CCGCGGCCGAAGCAGGCAA |
| 220 | cfn1249269 Common | TAAAAGAACACAAATGTGGCCCTAGTGAT |
| 221 | 219K1_166464 Common | GACCGTGGTATATGCCACCACGTT |
| 222 | 219K1_158251 Common | TCCTCACAAATCACGGGCCCCT |
| 223 | 219K1_111446 Common | AATATGATACAGACCCAAGACAAACCATTT |
| 224 | 219K1_110042 Common | GCATCTTCAAGGGAGCCACTCAAAA |
| 225 | 219K1_110005 Common | TTGACTCGATTCCGTGTGAGGCTAA |
| 226 | 219K1_107461 Common | GTTGATGCGAATTTGAAAATGACATAATAA |
| 227 | 219K1_99688 Common | GGGCGGGACCTGACTTGATGAT |
| 228 | 219K1_37 Common | GGCTTCATTATCAAATTCTGACCCATCTT |
| 229 | cfn1270524 Common | TGTACCGAAACTCAACCAAATGACCATTT |
| 230 | 136H5_3M5_7601 Common | CTTCTCTGTGGCCGAAAACCTCTT |
| 231 | cfn1288811 Common | GCACAATGTTTGACATTCGGTTTTCTAGTT |
| 232 | 136H5_3M5_89176 Common | CCTACCATCCTTAAATACTCTTGCTCAAA |
| 233 | 136H5_3M5_89263 Common | AAGCAACTAGAAAAATATTTGGACTAGCAT |
| 234 | 136H5_3M5_138211 Common | CCTCCCAACGGCCATCAATCAATTT |
| 235 | cfn0556874 Common | CCTGCTGGAAATGGGATTTCTTGTTTATT |
| 236 | 136H5_3M5_64154 Common | GATCATCGGGGAACCTGATGATAGTT |
| 237 | 136H5_3M5_68807 Common | TTGGTTGGTTACGTCAGGTTAAGACTTA |
| 238 | 136H5_3M5_77916 Common | GCTKTAGACTCTAAGTACCACAGAAGAA |
| 239 | cfn1246088 Common | GGGACGTGGAATTTGGAAAGACACAT |
| 240 | cfn1287194 Common | CAGAAGGCACTGGGAGGGATT |
| 241 | cfn1258380 Common | TATAGGAGTGATAGCACCACACAATTCAT |
| 242 | IWB72107* Common | ATACATGTCGGCGTCCCAGTCC |
| 243 | BS00090770 Common | GAAACATTCCTTCGGACAACTATGCATTA |
| 244 | cfn1239345 Common | ACCCTCGCTGCAGTTCCTTCTTAAA |
| 245 | RFL29_S2 Allele Common | TTTAGGACCTCCAGTGCATTTAACTCTTT |
| 246 | RFL29_S4 Allele Common | CAGTGCAACCTGCGGAGAGCAT |
| 247 | cfn0917304 Common | CAACTGCTTGGAGAAAGGCAACACAA |

TABLE 6-continued

Primers for use in detecting fertility restorer SNP markers of the invention (as indicated in the primer name)

| SEQ ID NO: | MARKER NAME | Sequence |
|---|---|---|
| 248 | cfn0919993 Common | CCATTAACAAGTACTGCATAGGTGCATAT |
| 249 | cfn0920459 Common | CCTCCTCCTAATTAAGCTCCTATAGATA |
| 250 | cfn0915987 Common | AAACGTGCAACGAGGCAAACCTCAT |
| 251 | cfn0920253 Common | GCCGCATGGTTTGGGCGGAAA |
| 252 | cfn0448874 Common | GTGCCTCTAGGTTCAACATAAATTTAGGTA |
| 253 | cfn0923814 Common | GATTTTCATTATCATGATCATCATTCATTT |
| 254 | cfn0924180 Common | AATGGCTTCAGACAAAATAAGAGGGAGAT |
| 255 | cfn0919484 Common | TCTCGCCTTTGTTTTGCCAAATGGTATAA |
| 256 | Excalibur_c96134_152 Common | CAAACTCCAACGGGTGGTGCGT |
| 257 | cfn3133296 Common | GCAATCCACCACTGTGGTACAACTT |
| 258 | LWE1_chr6B_485210_Rf4S Common | GGCACGATGACAGTAATGGGATGTT |
| 259 | LWE1_chr6B_11287944_Rf4S Common | AGAGTACACAGCATTTTCCCAGGAATATA |
| 260 | LWE1_chr6B_19775886_Rf4S Common | GTGGCAAGCAGATCATGACAGGTT |
| 261 | LWE1_chr6B_28157776_Rf4S Common | CTTGACGCATAAGGTGAAAGCCTGAA |
| 262 | RFL46_S2 Common | CCTTTATCAATCATCTGCCGGAGGAA |
| 265 | LWE1_chr7B_658281643_Rf7 Allele X | GAAGGTGACCAAGTTCATGCTGGGGTCTGTAAACTTGTGACGGA |
| 266 | LWE1_chr7B_658281643_Rf7 Allele Y | GAAGGTCGGAGTCAACGGATTGGGTCTGTAAACTTGTGACGGC |
| 267 | LWE1_chr7B_658281643_Rf7 Common | CTCTAACGATTCTTACACACGCACCAA |
| 268 | LWE1_chr7B_711539100_Rf7 Allele X | GAAGGTGACCAAGTTCATGCTCCTCTTCTCCAGATAATCAATCCTC |
| 269 | LWE1_chr7B_711539100_Rf7 Allele Y | GAAGGTCGGAGTCAACGGATTCCTCTTCTCCAGATAATCAATCCTA |
| 270 | LWE1_chr7B_711539100_Rf7 Common | GGCGACGGAGCTCGATGAGAAA |

Methods of Use of the Wheat Plants of the Disclosure

The plant according to the disclosure can be crossed, with any another inbred line, in order to produce a new line comprising either an increase or a decrease in the fertility level.

Alternatively, a genetic trait which has been engineered into a particular line using the foregoing techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene.

The wheat plant of the disclosure is also a wheat plant wherein one or more desired traits have further been introduced through backcrossing methods, whether such trait is a naturally occurring one or not.

The disclosure also relates to the use of the wheat plant as described above or its seeds, for food applications, preferably for flour production and for feed applications, or for breeding applications, for example in a method for improving agronomical value of a wheat plant, line, hybrid or variety.

As used herein, breeding applications encompass pedigree breeding to improve the agronomical value of a plant, line, hybrid, or variety.

Seeds harvested from plants described herein can be used to make flour by any available techniques in the art. The wheat plants or their flour are also useful as food product.

Sequences of SNP Markers

TABLE 7

Sequences of SNP markers

| Marker ID | Allele X | Allele Y | Sequence |
|---|---|---|---|
| 276I13_96B22_97797 | C | T | AAATTCGACAAGTACTATGGCTATGTCTCTGAATG[C/T]TTGTTTGGTTTTATTTGTCTATATTGTCGTTGTAT |
| cfn0522096 | C | G | ATGCAAAGTAGTACTCGTAGAGAGTTAACACAGAC[C/G]AGTGATTTATTGGGTGGTATTCTACTTGATATTTG |
| cfn0527763 | T | C | ATAAAGAAAAGTAGAGGAAGCTTATGAATAAAATGGAAAAGGAATTCAAAATTGCCGATAAATATAAAACTCATAACAAATCTAGCCACGCAAATGCCCG[T/C]GCCGCTCTGCTCGTTTGTACATGTCTCGGTGGACAAGGAAGAACCCAACAATTGCACAGGTCAATCTTATCCAGCAAAACAAGGAAGCAAACCAAACAGG |
| 104A4_105172 | TG | CA | ATGTTGCCTCTCGCTAGCCGCTGTCGMACCCAATGAATAATGTT[TG/CA]TGGGTTCTGGCTCCGAGAGGATGGCCGGCTYCCC |
| 104A4_105588 | A | C | GTTCCTTGTGACATGTACTCATA[A/C]ACAAGAGCCATATACTCCCCATCCTTGCA |
| cfn0373248 | T | A | GACATAATGTGTAATAACAGCCCATAATGCAATAAATATCAATATAAAAGCATGATGCAAAATGGACGTATCATTGCCACGRAAAAAATCTCACAAGATG[T/A]GACCATTTGATCCTCRTAATTGTTGTTCTAGACCCACTCCTAAGTMTAACATTCTTTATGTCTATYCTTCAAATCCCGAAGAGTAATGAAAACTATCGAA |
| cfn1097828 | T | C | CCATGAGTACCCGCTACTATCGATCTCCCTCCTCCCTGTAGGAGGCCTACGAACGATGCCCTCAGGTCCTGCTTCCTCTCGGTAGCGATGGATCCACCTG[T/C]GGTTGCTCTCTCAGGAACCAGTGTTGGCGGCGGCTCATCCGGGGCGCTGGATCTTGGTGATGTGCTGGAACAACTCAACTTGGAAGACGAAGAATTTGAT |
| cfn0527067 | A | G | GACAATATGATTCACCCTAGATCCTTCACCTTACA[A/G]TTCGAAAAAATAAAAGAACAAAAGTAATTTGACA |
| cfn0528390 | A | G | ACGAAGATGAGGAAGGTCTTCATGTTGGGTTTATG[A/G]TTACTAATACTTGCTTGGAATAGATGTTTTTGATC |
| BWS0267 | A | G | GTTACCCCAATATGCTCCCTCCTTGCACATTTTCTTCAGCTGCATAAAAAMCAGAATACC[A/G]CATCAGTTGCCTGAACCTTAACGCAGGTGCAGAAATAAGGCGACATAATTTYCACTAATC |
| cfn0527718 | C | T | AGGAAAATAAATTGTTCACAACATGGACATGAGAA[C/T]GGGGCAACCAAAAAGGGAAGAACATTGGAGGAAAC |
| cfn0524469 | G | T | TTTGTACTGCACGTAGTAAGTATTGATTTTTCTGT[G/T]TGCTCTCTGTGGACTTAGATTTGAAAATTGGCCTT |
| cfn0524921 | A | G | ATGCACATTGTTTCCATGTTAAGCTTATATTGTGC[A/G]TAACTCAAAAGATTGAAATGGAATTACCAAAGGGC |
| cfn1122326 | C | T | ACTGACTGTTGGAATCTGATTAAGACGCTGGAGAA[C/T]CCGAGCCAAGATATGTCACGACTAGGCCATCTGGA |
| RFL79_S7 | G | A | TGGGAAGCTTGATAAGGCTATGCTTATATTTA[G/A]AGATATGCAGAAACAAGGAGTGAG |
| cfn1252000 | A | G | AATCAGATCCTGTTAATGCTGTAGCCATTCTTGCA[A/G]GCGACACCTTGTCCCAGTCGTCTTATGGGCACTTA |

TABLE 7-continued

Sequences of SNP markers

| Marker ID | Allele X | Allele Y | Sequence |
|---|---|---|---|
| IWB14060 | A | G | GGCAGAGCCGGTCGACGGAGAGGAGCGCCATTC GACGCGTCTTCCGCAAT[A/G]TGTTTGCCTGCTTC GGCCGCGGCCATTCGGCGAGCTCCCACGCTTCGT CC |
| cfn1249269 | A | G | CGTTTAAAAGAACACAAATGTGGCCCTAGTGATCA [A/G]GTACACATATTTGTCACCTCTTTGAATCTTACT TA |
| 219K1_166464 | C | T | CGGGCTGATGAGGCTCTCGACGTGCTGCTTCACA GGATGCCTGAGCTGGGCTGCAC[C/T]CCCAACGTG GTGGCATATACCACGGTCATCCACGGCTTCTTTAA GGAAGGC |
| 219K1_158251 | G | A | GCGCTATCCGGCGTCGTGTTCCCTCTTGGGGGAA TCGTCCTGGAGATGGATCCGGTCA[G/A]AGGGGCC CGTGATTTGTGAGGATGTGTGTGTTGTTTCCCGAA AGGCG |
| 219K1_111446 | A | C | CTTTGACCTTAAATTCTTGTACTAATTTAGCAGAAT CGTTCTTCGAGAAGCACTC[A/C]AAAAATGGTTTGT CTTGGGTCTGTATCATATTTTCTCTGAACAAACAG GCGTGA |
| 219K1_110042 | T | C | GACTTAGCCTCACACGGAATCGAGTCAACCAATTC C[T/C]GTCGGTTTTGAGTGGCTCCCTTGAAGATGC AATCGTTTTCAGCATGGTCAGATTAATCAGCGAGC GTGC |
| 219K1_110005 | C | T | CATGTAGTGGCTGGCGTCTAAGCGCCTTTTCTTCT TCCAGCATCTA[C/T]GACTTAGCCTCACACGGAATC GAGTCAACCAATTCCTGTCGGTTTTGAGTGGCTCC CTTGAAGATG |
| 219K1_107461 | A | C | GTCGTATATATTGTTTGTATTAAAAAGTTGTGTGTT TTG[A/C]GTCATAATTTTTAAAATATTATTATGTCATT TTCAAATTCGCATCAAC |
| 219K1_99688 | T | C | AATCTTCTTGACTTCATCCATCCGCCTTGTTGCCCT GCGCAAAATCAAACT[T/C]CCCCGTCCTTATCATCA AGTCAGGTCCCGCCCTGGGCAGAGAGAG |
| 219K1_37 | C | T | CGGCAGATATCACAAAGGGCTATCCTGGTGAACA A[C/T]AAGATGGGTCAGAATTTGATAATGAAGCCTC AAGCCC |
| cfn1270524 | A | T | AATAGATGCACGCATCGGCGACCATTTTTTAGTAC TTTTTGCCTTTTTTGAAAATTTTGTCATTAAAAGACA AATGCCTAGTCTATACCTGATAAACTAA[A/T]ATCAT ACATAGAGAAAATGGTCATTTGGTTGAGTTTCGGT ACATGCTGAGATGGTTGCACTTCGGTGCATCTGCT TTGCTTCCATCACATCATAATGTCT |
| 136H5_3M5_7601 | T | C | GCTGCTTGTAGCGTCCCCCATGGCACCTG[T/C]GA AGAGGTTTTCGGCCACAGAGAAGGGGAAGGCTC |
| cfn1288811 | T | G | AAAATTACTTTTCACGCGCTTCGTTGGTCTGACAG TGCGAGCATAATTTTACTTTTTCTCAGTTTTACTTA ATTTGGTTAACCAAATCCTTTTTGATTTT[T/G]AACT AGAAAACCGAATGTCAAACATTGTGCAAATTTGGA AACTGAAACTGAAACCAAAAACCTAAAAAAATGATT AGTTTGTTTTTTTGTTCTTGTTTCG |
| 136H5_3M5_89176 | A | G | gtatttCTTAGGATTTTCTCACCGGCATCTCC[A/G]TTT TTTGAGCAAGAGTATTTAAGGATGGTAGGC |
| 136H5_3M5_89263 | C | T | AACAAAGATGCTAGTAAGAACATGAACCTAGTTGC TCATTTTTAACAACAATTGCCCACCAACCTGACATG CTCTTCCCATGTTCTTTTTTGCTCAAAA[C/T]AGAG ATGCTAGTCCAAATATTTTCTAGTTGCTTACATTT TAAACAACAATTGCCTACCATCCTTAAATACTCTTG CTCAAAAAACGGAGATGCCGGTGA |

TABLE 7-continued

Sequences of SNP markers

| Marker ID | Allele X | Allele Y | Sequence |
|---|---|---|---|
| 136H5_3M5_138211 | T | A | AATACAGACTGGGTGCAAAGCCAAGATGAT[T/A]GT AAAATTGATTGATGGCCGTTGGGAGGT |
| cfn0556874 | C | T | TGTAAAGAAGCTTAACCAGGAAAGCTATCAGGGCC ATAGGGAATGGCTGGTTAGTGACAATTTTGCCTGC TGGAAATGGGATTTCTTGTTTATTTCAGTT[C/T]TGC ATTGTGTCTGACATGCTCTTTCTTTTGGGCGCAGG CTGAAGTGAATTACCTTGGACAACTATCGCACCCG AATCTTGTAAAGCTCGTTGGGTACTGT |
| 136H5_3M5_64154 | T | C | TGGCGGAGCTGGGGCTGTTCCTCCTACGCAGGCG AAACTTCGCCGCGATAAA[T/C]GGAACTATCATCAG GTTCCCCGATGATCCATACG |
| 136H5_3M5_68807 | A | G | ACAAGCAACCGAGACAAGTTGCTCTTAATTATCTG TGCGT[A/G]CACCTCTAAGTCTTAACCTGACGTAAC CAACCAACCGTGT |
| 136H5_3M5_77916 | A | G | GATGGTTACAAGGCATGCATAGCAAGTAGAGTTAA CTTATCAAGTTATT[A/G]GTATTTTTCTTCTGTGGTA CTTAGAGTCTAMAGCTTGAGC |
| cfn1246088 | A | C | AATGGAAGCTGATGTGCGTTAGCGATAAAGCAACA GCGATAACGACGCATGGATCACCATGCTACTTGG GGAAGCAGGGACATCTGATGAGCCAGCATAC[A/C] CCCAGATATGTGTCTTTCCAAATTCCACGTCCCAA CAGATGAGCTATAAATTAATGCCACCTTCCTCCTA CAGCTAAATACTCCATCCGTTTCATAATGT |
| cfn1287194 | G | A | CAGAGGCATTCGTGAATTGGGCGAAATCAGAAGC AAGGAGCAGCGATGTTCAGCGCAGAAGGCACTGG GAGGGGATTCCAGGGAGGCTGCCCACCAGCCC [G/A]CCATCAGATACGGAGGAGGTGGATCCATGGCC CTACCTGTGTCCTGCGCCGAATCTGGACTGTGGT AACTACAGCGCCTGAATCTAGAGGTTCAGCCTGG |
| cfn1258380 | A | C | GATCCATCTCCCTTAATAATTTTGCTATTGGTATTG GGTATGGACATCTGAAGTGAAGGTTACGGCCGAT TTATAGGAGTGATAGCACCACACAATTCAT[A/C]AG AGCATCTGCAATAGATGAGTAGATGTAAAACTACT TAACTTTTACATCTCCGGGCCTAAAAACGCATCTG TAATAAGATAATGTAGATGTAAAGAAAA |
| IWB72107 | A | G | CGACGACGACGAGGATGCCGAGTTTGATGACATG GAGGATTATATCGACG[A/G]CGCGGACTGGGACGC CGACATGTATGATGATGTGTTCGATGTCTGAAGGA |
| BS00090770 | C | T | TAGCCGTAGGTCGTAGCACATAGCCGTTTA[C/T]GT AATGCATAGTTGTCCGAAGGAATGTTTC |
| cfn1239345 | A | G | TAACCTGGGGCTTCTTTTTTCTCCCTATAATATGG [A/G]CTGCCCTTTTAAGAAGGAACTGCAGCGAGGG TGCA |
| RFL29_S2 | A | G | CTATTCGATGGGCGTGTTTTAATTAACCGGGCAAC TCTCTTCTTCTTAATCA[A/G]TGAAAATGGCAAGTCT TTTACCTCGTTTCAAAAAGAGTTAAATGCACTGGA GGTCCTAAAGGTTTCG |
| RFL29_S4 | C | T | CATGCGGCGGGGCCCTGCGGCAATGATGACTC CATGAGGGTGG[C/T]TTCGGCGGACGATGCTCTCC GCAGGTTGCACTGGACTAGCTTGGTGTGAGGCTT GCAACTTTCTCCTGTGATGCTCATCAACAAAAT |
| cfn0917304 | G | T | GACTACGCGTTCCTCCCGGTGGTGGCGCTCTACC C[G/T]TTGTGTTGCCTTTCTCCAAGCAGTTGTGCCC TTCG |
| cfn0919993 | G | T | ATATCTTTACAAGTCATCGACTTACATGCTTCTTT [G/T]TATTATATGCACCTATGCAGTACTTGTTAATGGGT |
| cfn0920459 | C | G | GATGATATAACCGTAGCCAAGGAAGCCCAGATTTT [C/G]TTCTGTGTATCTATAGGAGCTTAATTAGGAGG AGG |

TABLE 7-continued

Sequences of SNP markers

| Marker ID | Allele X | Allele Y | Sequence |
|---|---|---|---|
| cfn0915987 | G | T | AAGTCTGCCATCCAGATCATTACCCAACGGCCAAT[G/T]GAGCCATGAGGTTTGCCTCGTTGCACGTTTTGGCT |
| cfn0920253 | A | C | GCAACAAAGCTGGTCATCCAAACATTTACATCGTT[A/C]GGCAGGCTTTCCGCCCAAACCATGCGGCCGACCTG |
| cfn0448874 | C | T | TATGTAAAACCTCTTTGTTTCTAAATAGCTGCGGC[C/T]CGCTACCTAAATTTATGTTGAACCTAGAGGCACCC |
| cfn0923814 | A | C | GTTCGGCAGAATCCAAGTCGCAAATGTAAGGTCAG[A/C]AAATGAATGATGATCATGATAATGAAAATCATAAG |
| cfn0924180 | A | G | ACGTATGGAGCTTCCTCTTTTCATCATGCACCATT[A/G]TGATCTCCCTCTTATTTTGTCTGAAGCCATTCATG |
| cfn0919484 | A | G | AGGTCATGAAAATGCAAGTGGCGAATCTTATCTCT[A/G]TTATACCATTTGGCAAAACAAAGGCGAGAGTTCTG |
| TaContig158085_61_BS00011513 | A | G | AGTAATTACAACCTTGGCGGCATTTCCAAG[A/G]ACTTCTTTGTCTGCTTTGTCCAGGGACAGT |
| cfn0864865 | C | T | CGGTTTATCTGTTATCATTGTGCACCAGGAAAACC[C/T]GACTCCTGAGTTCAAAAATATGTTGATTCTATAAA |
| EXCALIBUR_C96134_152 | T | C | GGCTTAAGGGAGACTCTGGTGACACCATGTAACTT[C/T]ACGGCCACGCACCACCCGTTGGAGTTTGACAGTTC |
| cfn3133296 | A | G | CTCCCCTGCCAAACCCAAGTGTCCCTCCTTGAGTC[A/G]CAAAGTTGTACCACAGTGGTGGATTGCAACAGATT |
| LWE1_chr6B_485210_Rf4S | G | T | ACTGGGAACTGCGCTACACCTTCTACGTGGATAATGGCGACTKCGACGAGCTAMGGGGCGTCTGGCACGATGACAGTAATGGGATGTTGTGCTACTGGCT[G/T]GGTGACGATCTCTACAAGTATGACACCAGTAAGAAGGGTCAACAACTGACCGCCGATAGTGTCTTGAGTGGGACCATCGGATCCCCCTGCCGGCAACTA |
| LWE1_chr6B_11287944_Rf4S | A | G | CTATAAGGAAAGCATATCACTGTAAACAGTATACTATGACAGAAACAAAGAGTACACAGCATTTTCCCAGGAATATATAATATATACTTCATTTACTGGT[A/G]GTTGATGTGTGTAGTCCTAAACAGAAGATGAAGGCTATGCTTTCAATATCAAAAAGCGAAAATAAACAGAATAACCAGCATAGTTGCAGTAATTACAATTTG |
| LWE1_chr6B_19775886_Rf4S | A | G | TAATTTCTATATACACACATACAACATGTGCACATACAATGCGTACGTGGCAAGCAGATCATGACAGGTTGGCGGACGCGGTTCTCCGCCGGGGACGAC[A/G]CCAGTGCCGGCGCCCTTCATCTCGGCCCGAAATTTGGCGGAGAGTGCGTTTCTCCCGGCTGCGGGAGCCGTGGGCCAAAAGAGGCCCATGCTGACAGCCA |
| LWE1_chr6B_28157776_Rf4S | A | C | TTKATAGTAAAACCAAGCGTACAGAATTAATTTTAGAGCAAACAAAATACTATAATAGAAGTCAAGCCTTGACGCATAAGGTGAAAGCCTGAACCGACG[A/C]TAGTAATCAGTAAGCAGATCGTTTCTAAATAAGATGATGAATGGTTTATGTTTTCCCGCTGTTAGAATATTGTTCAGCAAACAGCATAGCTAGGACTGTT |
| RFL46_S2 | A | G | ATTGATGCGCTGTGCAAGGCCAGAGCTATGGACAAAGCA[A/G]AGTTGTTCCTCCGGCAGATGATTGATAAAGGTGTTC |
| LWE1_chr7B_658281643_Rf7 | T | G | GAACAATCTCCCCCTACGATTGACTGACGACGACGAGATCCCACAGTCAAGCCCTCCATTTTCCTCAGAAAACTCTAACGATTCTTACACACGCACCAAA[T/G]C |

TABLE 7-continued

Sequences of SNP markers

| Marker ID | Allele X | Allele Y | Sequence |
|---|---|---|---|
| | | | CGTCACAAGTTTACAGACCCCTGGCATGGATGCA CGCACGGTGCAGCCAGCCGGCCCAGGATTTTCAT ACGTTTGCTATACGTTACGTCGAGAGGGAGT |
| LWE1_chr7B_711539100_Rf7 | C | A | TCAATTCCTTGTTGTCCTTCTTCAGTTCCTCGTTGT GCTTGGCCAGCTTCCTTTTGCCCTCCACCAGCACC TCGTTCCTCTTCTCCAGATAATCAATCCT[C/A]ATCT TTTTTTTCTCATCGAGCTCCGTCGCCAACTTTCCTT TCTTCTCCACCAGCGCATTTTTTGCCTTTTCCAGAT CTGCAATATCTGTTCCCTTTTTT |

The Examples below are given for illustration purposes only.

EXAMPLES

Example 1

Origin, Restoring Efficiency and Breeding of the Locus Rf4s from *Aegilops Speltoides*

Rf4 is located on the 6B chromosome of the accession R113, which also carry the restorer gene Rf1, and is partially restoring the fertility of alloplasmic wheat with *T. timopheevii* cytoplasm (Maan et al; 1984).

L13 is a line derived from R113 and carry only Rf4 (Australian Grain Genebank 90819). The presence of Rf4 has been confirmed via a QTL identification located on 6BS in a mapping population of 117 F2 individuals of a cross "CMS line/L13" (Data not shown). Locus on 6BS with a pvalue=$1.08E^{-13}$, explains 70.5% of the total variance).

GSTR435 is a *Ae. speltoides* introgression line with Lr36 (Pedigree: Neepawa/Line 2-9-2(Neepawa*5/*Aegilops speltoides* 2-9)//3*Manitou; USDA, E84018). The introgression is located at the distal part of the short arm of chromosome 6B (Dvorak J and Knott D R, 1990).

GSTR435 is partially restoring the fertility of alloplasmic wheat with *T. timopheevii* cytoplasm and this partial restoration of fertility is higher than that of L13. See Table 8

TABLE 8

Fertility level expressed as the average number of kernels per spikelet of F1 plants (cross sterile CMS line/GSTR435 or L13). F1 plants = number of individual F1 plants, σ = standard deviation, x̄ = average in kernels per spikelet

| Genotype | F1 plants | σ | x̄ |
|---|---|---|---|
| GSTR435 | 10 | 1.0 | 1.7 |
| L13 | 12 | 0.4 | 0.8 |

A mapping population has shown that the restoring locus of GSTR435 is located on the distal part of the short arm of chromosome 6B (Data not shown). This mapping population was made of a F2 population of 94 individuals of a cross "CMS line/GSTR435" (Locus on 6BS with a pvalue= $3.15^{E-12}$, explains 68.4% of the total variance).

This new restorer locus has been named Rf4s, in opposition to the Rf4 locus present in R113 and L13 of *T. timopheevii* origin.

LGWR20-0485 is an alloplasmic restorer line developed by Limagrain through pedigree breeding from a cross between GSTR435, Rf1 and Rf3strong donors and elite lines. LGWR20-0485 is a winter wheat type agronomically adapted to the cultivation in Western Europe and is homozygous for the restorer alleles Rf1, Rf3 and the introgression from GSTR435 carrying Rf4s (Table 9). Sister lines with the same haplotype have been derived from the same initial cross. The presence of the locus Rf4s is revealed by the use of the KASP LWE1_chr6B_28157776_Rf4 and LWE1_chr6B_11287944_Rf4S.

TABLE 9

Haplotypes for the loci Rf1, Rf3strong, Rf4s and the cytoplasm of the maintainor elite line Apache and of the restorer line LGWR20-0485

| Locus | Rf1 | Rf3 strong | Rf4s | Cytoplam |
|---|---|---|---|---|
| Marker | RFL79_S7 | RFL29_S4 | LWE1_chr6B_28157776_Rf4 | ORF279_S4 |
| APACHE | A | T | A | G |
| LGWR20-0485 | G | C | C | C |

Example 2

Characterization of the Genomic Region Containing Rf4 *Aegilops Speltoides* Genetic Determinants Two strategies have been used to determine Rf4s genomic region from *Ae. speltoides*. A F2 mapping population to perform fine mapping and sequencing data do dertermine the *Ae. speltoides* introgression size from the GSTR435 donor line.

First, a F2 mapping population segregating for Rf4 GSTR435×Manenick_CMS encompassing 94 individuals was phenotyped and genotyped with 18100 SNP markers using Limagrain's internal genotyping platform.

Fertility tests were conducted indoors under controlled growth conditions, either in growth chambers or in greenhouses, enabling normal fertility of the tested wheat plants. The fertility scores indicated have been calculated by dividing the total number of seeds threshed from a spike by the number of counted spikelets. Whole genome QTL analysis was conducted on F2 plants using a Composite Interval Mapping approach (internal tool) and internal genetic consensus map.

Rf4 was first mapped on the short arm of the chromosome 6B between 6 cM and 43 cM on Limagrain's internal consensus map and physically delimited by SNP markers TaContig158085_61_BS00011513 and cfn0864865. These two SNP markers delimit the largest possible interval defined by the three mapping populations.

In a second step, the locus was fine-mapped by screening 1811 and 3142 F3 lines from GSTR435×Manenick_CMS derived from F2 plants heterozygous at the locus. Phenotyping and analysis of recombinant plant progenies within the interval redefined a smaller mapping interval between 6 and 36 cM delimited by EXCALIBUR_C96134_152 and cfn3133296 SNP markers. Using this new QTL analysis, we concluded that the gene could be from the start of the 6B chromosome to the cfn3133296 marker so from 0 to the physical position 29 782 272 (position reference IWGSC V1).

Secondly, we used sequencing data do determine the GSTR435 Ae. speltoides introgression size containing RF4 locus. Due to the wheat genome size, we performed internal partial sequencing using Exome capture approach. Exome sequencing strategy is commonly used in wheat to detect SNP and highlights wild-relative introgression (Hu et al., 2019), but any whole genome sequencing strategy can give access to the same information.

By computing reads sequences coverage variations inside exons between different non Rf4 wheat lines and the Rf4 GSTR435 line, it has been confirmed that the GSTR435 contain an alien introgression (Ae. speltoides) on the short arm of the 6B chromosome. We estimated the Aegilops speltoides introgression position from start 0 to 32 334 597 bp on 6B (physical position reference IWGSC V1).

Finally, 377 polymorphic SNP specific from GSTR435 6B Ae. speltoides introgression have been extracted and are usable to follow and identify the Rf4s locus. From the 377 polymorphic SNP, 4 have been converted into Kaspar markers to follow the Rf4s introgression:
LWE1_chr6B_485210_Rf4S,
LWE1_chr6B_11287944_Rf4S,
LWE1_chr6B_19775886_Rf4S, and
LWE1_chr6B_28157776_Rf4S.

Example 3

Origin, Restoring Efficiency and Breeding of the T4BS 6BL 6RL Rye Introgression

The long arm of chromosome 6R of rye from addition lines is restoring the fertility of alloplasmic wheat with T. timopheevii cytoplasm (Curtis and Lukaszewski, 1993).

4 translocation lines with 6RL have been created and are available upon order at the Wheat Genetics Resource Center of the Kansas State University They contain three different events of translocation between 6RL and wheat chromosomes:
TA5030 (KS92WGRC17, P1592729) T6BS·6BL-6RL (Sebesta et al., 1997)
TA5031(KS92WGRC18, P1592730) T4BS·4BL-6RL (Sebesta et al., 1997)
TA5032 (KS92WGRC19, P1592731) T4BS·4BL-6RL (Sebesta et al., 1997)
TA5041 (KS93WGRC28, P1583794) T6BS·6RL, descendant of TA2929 (TAM104, Friebe et al., 1995)

The three radiation induced chromosomal translocations T6BS·6RL, T6BS·6BL-6RL and T4BS·4BL-6RL can restore partially the fertility of alloplasmic wheat with T. timopheevii cytoplasm (Table 10). The 6RL arm has a proximal region with homoeology to the wheat group 6 chromosome, one interstitial region with homoeology to the long arms of the wheat group 3 chromosomes and a distal region with homoeology to the long arms of the wheat group 7 chromosomes (Devos et al., 1993). It is consequently highly unlikely that the translocated 6RL chromosome piece in T4BS·4BL-6RL may recombine with the group chromosome.

TABLE 10

Fertility level expressed as the average number of kernels per spikelet of F1 plants (cross sterile CMS line/TA2929 or TA5030 or TA5031). F1 plants = number of individual F1 plants, σ = standard deviation, x̄ = average of kernels per spikelet

| Genotype | F1 plants | CY | x̄ |
|---|---|---|---|
| TA2929 | 16 | 0.46 | 1.04 |
| TA5030 | 51 | 1.01 | 1.14 |
| TA5031 | 64 | 0.87 | 1.69 |

LGWR17-0160 is an alloplasmic restorer line developed by Limagrain through pedigree breeding from a cross between TA5031, Rf1 and Rf3 donors and elite lines.

LGWR17-0160 is a winter wheat type line agronomically adapted to the cultivation in Western Europe and is homozygous for the restorer alleles Rf1, Rf3 and the introgression T4BS·4BL-6RL from TA5031 (Table 11, the T4BS·4BL-6RL translocation being called "6RL").

The T4BS·4BL-6RL translocation is revealed by the allele "A" for the KASP marker RFL46_S2, the allele "G" of this marker indicates the absence of the translocation and consequently the absence of the capacity of fertility restoration. The accession TA5041 is equally carrying the restorer allele "A" for the KASP marker RFL46_S2.

TABLE 11

Haplotypes for the loci Rf1, Rf3, the introgression T4BS•4BL-6RL (coded 6R) and the cytoplasm of the maintain or elite line Apache and of the restorer line LGWR17-0160

| Locus | Rf1 | Rf3 | 6RL | Cytoplasm |
|---|---|---|---|---|
| Marker | RFL79_S7 | RFL29_S4 | RFL46_S2 | ORF279_S4 |
| APACHE | A | T | G | G |
| LGWR17-160 | G | C | A | C |

The TA5031 should have the T4BS·4BL-6RL translocation. But according to the dominant profiles of the markers and the fact that the RFL46_S2 is "diagnostic" we think that this donor is T6BL-6RL translocated. We noticed these dominant profiles on the 6B from 48.9 cM to 114.8 cM (=end of the chromosome).

Example 4

New Rf Alleles Combinations for a Full Fertility Restoration of CMS Hybrids

It is largely admitted that the full fertility restoration of the cultivated CMS hybrid can only be reached by the cumulative effect of several Rf loci with major effect, possibly with the combined help of modifier gene(s) that may help enhance the overall fertility expression.

A minimum of three Rf genes would need to be bred together in a restorer line to create a timely and geographically stable restoration of fertility of the F1.

The use of molecular markers tightly linked to the respective Loci is therefore necessary as the fertility scores of the restorer line alone would not suffice in creating a combination of three Rf alleles.

The following example demonstrates the impossibility to create restorer line, with the *Triticum timopheevii* cytoplasm, homozygous at three loci or more without using molecular markers strictly linked to the genes.

This applies to any breeding method used as for instance doubled haploid, pedigree breeding, single seed descent, backcross.

Out of the 27 possible different haplotypes created through the generations, 17 could lead to a full fertility of the restorer line misleading the breeder into creating fully fertile restorer lines not containing all the three restoring alleles (Table 12).

TABLE 12

Estimated level of fertility restoration for every individual haplotype of the combination between restoring alleles (Rf) and non-restoring alleles (rf) of the 3 loci Rf1, Rf3 and Rf4s in alloplasmic restorer lines.

| Restorer alleles | Locus Rf1 | Locus Rf3strong | LocusRf4s | Fertility |
|---|---|---|---|---|
| 0 | rf1/rf1 | rf3/rf3 | rf4s/rf4s | 0% |
| 1 | rf1/Rf1 | rf3/rf3 | rf4s/rf4s | 25-50% |
| 1 | rf1/rf1 | rf3/Rf3 | rf4s/rf4s | 25-50% |
| 1 | rf1/rf1 | rf3/rf3 | rf4s/Rf4s | 25-50% |
| 2 | Rf1/Rf1 | rf3/rf3 | rf4s/rf4s | 50-75% |
| 2 | rf1/rf1 | Rf3/Rf3 | rf4s/rf4s | 50-75% |
| 2 | rf1/rf1 | rf3/rf3 | Rf4s/Rf4s | 50-75% |
| 2 | rf1/Rf1 | rf3/Rf3 | rf4s/rf4s | 50-75% |
| 2 | rf1/Rf1 | rf3/rf3 | rf4s/Rf4s | 50-75% |
| 2 | rf1/rf1 | rf3/Rf3 | rf4s/Rf4s | 50-75% |
| 3 | Rf1/Rf1 | rf3/Rf3 | rf4s/rf4s | full |
| 3 | Rf1/Rf1 | rf3/rf3 | rf4s/Rf4s | full |
| 3 | rf1/Rf1 | Rf3/Rf3 | rf4s/rf4s | full |
| 3 | rf1/rf1 | Rf3/Rf3 | rf4s/Rf4s | full |
| 3 | rf1/Rf1 | rf3/rf3 | Rf4s/Rf4s | full |
| 3 | rf1/rf1 | rf3/Rf3 | Rf4s/Rf4s | full |
| 3 | rf1/Rf1 | rf3/Rf3 | rf4s/Rf4s | full |
| 4 | Rf1/Rf1 | Rf3/Rf3 | rf4s/rf4s | full |
| 4 | Rf1/Rf1 | rf3/Rf3 | rf4s/Rf4s | full |
| 4 | rf1/rf1 | Rf3/Rf3 | Rf4s/Rf4s | full |
| 4 | rf1/Rf1 | Rf3/Rf3 | rf4s/Rf4s | full |
| 4 | rf1/rf1 | Rf3/Rf3 | Rf4s/Rf4s | full |
| 4 | rf1/Rf1 | rf3/Rf3 | Rf4s/Rf4s | full |
| 5 | Rf1/Rf1 | Rf3/Rf3 | rf4s/Rf4s | full |
| 5 | Rf1/Rf1 | rf3/Rf3 | Rf4s/Rf4s | full |
| 5 | rf1/Rf1 | Rf3/Rf3 | Rf4s/Rf4s | full |
| 6 | Rf1/Rf1 | Rf3/Rf3 | Rf4s/Rf4s | full |

Nine Rf genes restoring the fertility of the T. timopheevii cytoplasm have been identified to date: Rf1 (1A), Rf2 (7D), Rf3 (1B), Rf4 (6B), Rf5 (6D), Rf6 (5D), Rf7 (7B), Rf8 (2D) and Rf9 (6AS) (Tahir and Tsunewaki 1969; Yen et al., 1969; Bahl and Maan 1973; Mukai and Tsunewaki 1979; Wilson and Driscoll 1983; Maan et al., 1985; Du et al., 1991; Sinha et al., 2013; Shahinnia et al. 2020).

Individually, all those 9 Rf locus may display different levels of expressivity and their combinations may not prove strictly additive, exemplified by the non-additive effect of the loci Rf4 and Rf1 (Geyer et al., 2017).

Table 13 below shows a series of F1 fertility scorings when using restorer lines with different combinations of 3 to 4 restorer alleles.

TABLE 13

Fertility level, expressed as the average number of seeds per spikelet, and seedset, expressed as the average total number of seeds per spike, of F1 plants produced with a series of restorer lines displaying different combination of the restorer loci Rf1, Rf3, Rf3w (Rf3 "weak"), Rf4, Rf4s and 6R. nb = number of individual spikes. σ = standard deviation, $\bar{x}$ x = average.

| | FERTILITY | | | SEEDSET | | |
|---|---|---|---|---|---|---|
| | nb | average | σ | nb | average | σ |
| Rf1 + Rf3 + Rf7 | 119 | 2.84 | 0.51 | 119 | 57.21 | 13.69 |
| Rf1 + Rf3 + 6R | 42 | 2.41 | 0.44 | 42 | 54.14 | 11.31 |
| Rf1 + Rf3 + Rf4s | 93 | 2.59 | 0.35 | 93 | 59.09 | 10.97 |
| Rf1 + Rf3 + Rf4 | 7 | 2.08 | 0.45 | 7 | 37.00 | 9.09 |
| Rf1 + Rf3 + Rf4 + Rf7 | 9 | 2.16 | 0.32 | 9 | 49.00 | 7.55 |
| Rf1 + Rf3w + Rf4 + Rf7 | 39 | 2.22 | 0.32 | 39 | 41.82 | 6.92 |
| Rf1 + Rf3w + Rf7 | 265 | 2.37 | 0.45 | 265 | 53.83 | 11.37 |
| Rf3 + Rf7 + 6R | 18 | 2.62 | 0.22 | 18 | 52.28 | 7.09 |
| Rf3w + Rf4 + Rf7 | 10 | 1.80 | 0.48 | 10 | 34.40 | 10.52 |
| Checks | 189 | 2.7 | 0.5 | 189 | 56.9 | 12.1 |

Four combinations of three Rf restoring alleles are either statistically better or equivalent ($\alpha=0.05$) to the group of elite lines (indicated as checks), either for the fertility or for the seedset or for both: Rf1+Rf3+Rf7, Rf3+Rf7+6R, Rf1+Rf3+Rf4s and Rf1+Rf3+6R. All the other combinations of three or four Rf alleles are statistically inferior to the group of checks ($\alpha=0.05$) for both fertility and seedset (Tables 14 and 15).

TABLE 14 t Student test for mean comparison for fertility of F1 plants and checks (average number of kernels per spike). The haplotype column indicates the Rf alleles combination of the restorer line used to produce the F1 plants. $\alpha = 0.05$

| Haplotype | | | | | Mean |
|---|---|---|---|---|---|
| Rf1 + Rf3 + Rf7 | A | | | | 2.8360804 |
| checks | A | | | | 2.7353917 |
| Rf3 + Rf7 + 6R | A | B | C | | 2.6153608 |
| Rf1 + Rf3 + Rf4s | | B | | | 2.5861419 |
| Rf1 + Rf3 + 6R | | | C | D | 2.4073307 |
| Rf1 + Rf3w + Rf7 | | | | D | 2.3675521 |
| Rf1 + Rf3w + Rf4 + Rf7 | | | | D | 2.2183024 |
| Rf1 + Rf3 + Rf4 + Rf7 | | | | D | E | 2.1648731 |
| Rf1 + Rf3 + Rf4 | | | | D | E | 2.0812417 |
| Rf3w + Rf4 + Rf7 | | | | | E | 1.7988889 |

TABLE 15 t Student test for mean comparison for seedset of F1 plants and checks (average number of kernels per spike). The haplotype column indicates the Rf alleles combination of the restorer line used to produce the F1 plants. $\alpha = 0.05$

| Haplotype | | | | | Mean |
|---|---|---|---|---|---|
| Rf1 + Rf3 + Rf4s | A | | | | 59.086022 |
| Rf1 + Rf3 + Rf7 | A | B | | | 57.210084 |
| checks | A | B | | | 56.888889 |
| Rf1 + Rf3 + 6R | | B | C | | 54.142857 |
| Rf1 + Rf3w + Rf7 | | | C | | 53.826415 |
| Rf3 + Rf7 + 6R | | B | C | | 52.277778 |
| Rf1 + Rf3 + Rf4 + Rf7 | | | C | D | 49.000000 |
| Rf1 + Rf3w + Rf4 + Rf7 | | | | D | E | 41.820513 |
| Rf1 + Rf3 + Rf4 | | | | | E | 37.000000 |
| Rf3w + Rf4 + Rf7 | | | | | E | 34.400000 |

In Tables 14 and 15, for all variables with the same letter, the difference between the means is not statistically significant.

BIBLIOGRAPHY

Ahmed et al., 2001. QTL analysis of fertility restoration against cytoplasmic male sterility in wheat. Genes Genet Syst, 76:33-38.

Bahl P N, Maan S S, 1973. Chromosomal location of fertility restoring genes in six lines of common wheat. Crop Sci 13: 317-320.

Bennetzen J L et al., 2012. Reference genome sequence of the model plant Setaria. Nat Biotechnol 30 (6):555-+. doi: 10.1038/nbt.2196

Brenchley R, et al., 2012. Analysis of the bread wheat genome using whole-genome shotgun sequencing. Nature 491 (7426):705-710. doi:10.1038/nature11650

Cannarozzi G, et al., 2014. Genome and transcriptome sequencing identifies breeding targets in the orphan crop tef (Eragrostis tef). Bmc Genomics 15. doi:Artn 58110.1186/1471-2164-15-581

Chen J F et al., 2013. Whole-genome sequencing of Oryza brachyantha reveals mechanisms underlying Oryza genome evolution. Nature Communications 4. doi:ARTN 159510.1038/ncomms2596

Cheng S F, Gutmann B, Zhong X, Ye Y T, Fisher M F, Bai F Q, Castleden I, Song Y, Song B, Huang J Y, Liu X, Xu X, Lim B L, Bond C S, Yiu S M, Small I (2016) Redefining the structural motifs that determine RNA binding and RNA editing by pentatricopeptide repeat proteins in land plants. Plant Journal 85 (4):532-547. doi:10.1111/tpj.13121.

Christensen A H and Quail P H, 1996. Ubiquitin promoter-based vectors for high-level expression of selectable and/or screenable marker genes in monocotyledonous plants. Transgenic Res, May; 5(3):213-8.

Christian et al., 1992. Maize polyubiquitin genes: structure, thermal perturbation of expression and transcript splicing, and promoter activity following transfer to protoplasts by electroporation. Plant Mol Biol. 18(4):675-89.

Curtis and Lukaszewski, 1993. Localization of genes in Rye that restore male fertility to hexaploid wheat with timopheevii cytoplasm. Plant breeding, 11:106-112.

Depigny-This D et al., 1992. The cruciferin gene family in radish. Plant Molecular Biology, 20: 467-479.

Du H, Maan S S, Hammond J J (1991) Genetic analyses of male fertility restoration in wheat. III. Effects of aneuploidy. Crop Sci 31:319-322

Fehr W R et al, 1987. Principles of Cultivar Development Vol. 1 Theory and Technique. Macmillan, New York.

Fujii S, Bond C S, Small I D (2011) Selection patterns on restorer-like genes reveal a conflict between nuclear and mitochondrial genomes throughout angiosperm evolution. P Natl Acad Sci USA 108 (4):1723-1728. doi:DOI 10.1073/pnas.1007667108.

Geyer M et al., 2016. Distribution of the fertility-restoring gene Rf3 in common and spelt wheat determined by an informative SNP marker. Mol Breeding, 36:167. DOI 10.1007/s11032-016-0592-6.

Götz H et al., 2011.Transgene Expression Systems in the Triticeae Cereals. Journal of Plant Physiology 168, no. 1 : 30-44. doi:10.1016/j.jplph.2010.07.007.

International Brachypodium I (2010) Genome sequencing and analysis of the model grass Brachypodium distachyon. Nature 463 (7282):763-768. doi:10.1038/nature08747

Jacquemin J, et al., 2013. The International Oryza Map Alignment Project: development of a genus-wide comparative genomics platform to help solve the 9 billion-people question. Curr Opin Plant Biol 16 (2):147-156. doi:10.1016/j.pbi.2013.02.014.

Jefferson, R. A., 1987. Assaying chimeric genes in plants: The GUS gene fusion system. Plant Mol. Biol. Report. 5, 387-405. D01:10.1007/BF02667740

Jia J, et al., 2013. *Aegilops tauschii* draft genome sequence reveals a gene repertoire for wheat adaptation. Nature 496 (7443):91-95. doi:10.1038/nature12028.

Jones H D, 2015. Wheat Biotechnology: Current Status and Future Prospects. K. Azhakanandam et al. (eds.), Recent Advancements in Gene Expression and Enabling Technologies in Crop Plants, DOI 10.1007/978-1-4939-2202-4_8.

Kay R, et al., 1987. Duplication of CaMV 35S promoter sequences creates a strong enhancer for plant genes. Science 236:1299-1302.

Kawahara Y et al., 2013. Improvement of the *Oryza sativa* Nipponbare reference genome using next generation sequence and optical map data. Rice 6. doi:Artn 410.1186/1939-8433-6-4.

Kihara, 1951, Genome analysis in *Triticum* and *Aegilops* X. Concluding review. Cytologia, 16: 101-123.

Kojima et al., 1997, High-resolution RFLP mapping of the fertility restoration (Rf3) gene against Triticum timopheevii cytoplasm located on chromosome 1BS of common wheat. Genes Genet Syst, 72: 353-359.

Krasileva K V et al., 2013. Separating homeologs by phasing in the tetraploid wheat transcriptome. Genome Biol 14 (6). doi:ARTN R66 10.1186/gb-2013-14-6-r66.

Li et al., 2003. OrthoMCL: Identification of Ortholog Groups for Eukaryotic Genomes. Genome Res. 2003 September; 13(9): 2178-2189.

Li H. and Durbin R, 2010. Fast and accurate long-read alignment with Burrows-Wheeler Transform. Bioinformatics, Epub. [PMID: 20080505]

Ling H Q et al., 2013. Draft genome of the wheat A-genome progenitor *Triticum urartu*. Nature 496 (7443): 87-90. doi:10.1038/nature11997

Longin et al., 2012, Hybrid breeding in autogamous cereals. Theor Appl Genet.: 125:1007-1096. DOI 10.1007/s00122012-1967-7.

Ma Z Q and Sorrells M E, 1995, Genetic analysis of fertility restoration in wheat using RFLP. Crop Sci., 35:1137-1143.

Maan, S. S. Genetic analyses of male-fertility restoration in wheat: isolation, penetrance, and expressivity of Rf genes. Crop Sci. 25, 743-748 (1985).

Mace E S et al., 2013. Whole-genome sequencing reveals untapped genetic potential in Africa's indigenous cereal crop sorghum. Nat Commun 4:2320. doi:10.1038/ncomms3320.

McElroy D et al., 1990. Isolation of an Efficient Actin Promoter for Use in Rice Transformation. The Plant Cell, Vol. 2, 163-171.

Martis M M et al., 2013. Reticulate Evolution of the Rye Genome. Plant Cell 25 (10):3685-3698. doi:10.1105/tpc.113.114553

Mayer K F X, et al., 2014. A chromosome-based draft sequence of the hexaploid bread wheat (Triticum aestivum) genome. Science 345 (6194). doi:ARTN 125178810.1126/science.1251788

Mayer K F X et al., Conso IBGS, 2012. A physical, genetic and functional sequence assembly of the barley genome. Nature 491 (7426):711-+. doi:10.1038/nature11543.

Melonek, J., Duarte, J., Martin, J. et al. The genetic basis of cytoplasmic male sterility and fertility restoration in wheat. Nat Commun 12, 1036 (2021). https://doi.org/10.1038/s41467-021-21225-0

Mukai Y, Tsunewaki K (1979) Basic studies on hybrid wheat breeding. A new male sterility-fertility restoration system in common wheat utilizing the cytoplasms of *Aegilops kotschyi* and *Ae. Variabilis*. Theor Appl Genet 54:153-160.

Ouyang S et al, 2007. The TIGR Rice Genome Annotation Resource: Improvements and new features. Nucleic Acids Res 35:D883-D887. doi:10.1093/nar/gk1976.

Pallavi Sinha P et al., 2013. Genetic analysis and molecular mapping of a new fertility restorer gene Rf8 for *Triticum timopheevii* cytoplasm in wheat (*Triticum aestivum* L.) using SSR markers. Genetica, 141: 131-141.

Paterson A H et al., 2009. The Sorghum bicolor genome and the diversification of grasses. Nature 457 (7229):551-556. doi:10.1038/nature07723.

Rathburn and Hedgcoth, 1991. Chimeric open reading frame in the 5' flanking region of coxI mitochondrial DNA from cytoplasmic male-sterile wheat. Plant Mol. Biol., 16:909-912.

Rice P et al., 2000. A. EMBOSS: The European molecular biology open software suite. Trends Genet 16, 276-277, 10.1016/S0168-9525(00)02024-2.

Sakai H, et al., 2013. Rice Annotation Project Database (RAP-DB): An Integrative and Interactive Database for Rice Genomics. Plant Cell Physiol 54 (2):E6-+. doi: 10. 1093/pcp/pcs183.

Schnable P S, et al., 2009. The B73 Maize Genome: Complexity, Diversity, and Dynamics. Science 326 (5956): 1112-1115. doi:10.1126/science.1178534.

Shahinnia F, Geyer M, Block A, Mohler V, Hartl L. Identification of Rf9, a Gene Contributing to the Genetic Complexity of Fertility Restoration in Hybrid Wheat. Front Plant Sci. 2020 Dec. 10; 11:577475. doi: 10.3389/fpls.2020.577475. PMID: 33362809; PMCID: PMC7758405.

Sinha, P., Tomar, S. M. S., Vinod, Singh, V. K., and Balyan, H. S. (2013). Genetic analysis and molecular mapping of a new fertility restorer gene Rf8 for *Triticum timopheevi* cytoplasm in wheat (*Triticum aestivum* L.) using SSR markers. Genetica 141, 431-441. doi: 10.1007/s10709-013-9742-5

Singh S K et al., 2010. Perspective of hybrid wheat research: a review. Indian J Agric Sci 80:1013-1027.

Song and Hedgcoth, 1994. Influence of nuclear background on transcription of a chimeric gene orf256 and cox1 in fertile and cytoplasmic male sterile wheats. Genome, vol.37

Stojalowski S et al., 2013. The importance of chromosomes from the sixth homeologic group in the restoration of male fertility in winter triticale with *Triticum tomopheevii* cytoplasm. J. Appl. Genetics, 54:179-184.

Tahir, C. M. & Tsunewaki, K. Monosomic analysis of *Triticum spelta* var. *duhamelianum*, a fertility-restorer for *T. timopheevi* cytoplasm. Jpn. J. Genet. 44, 1-9 (1969).

Ch. M. Tahir and K. Tsunewaki, 1971. Monosomic analysis of fertility-restoring genes in *Triticum Aestivum* strain p168. Canadian Journal of Genetics and Cytology. https://doi.org/10.1139/g71-003.

Verdaguer et al., 1996. Isolation and expression in transgenic tobacco and rice plants, of the cassava vein mosaic virus (CVMV) promoter. Plant Molecular Biology 31: 1129-1139.

Wang M H et al., 2014. The genome sequence of African rice (*Oryza glaberrima*) and evidence for independent domestication. Nat Genet 46 (9):982-+. doi:10.1038/ng.3044

Wilson J A, Ross W M. 1962. Male sterility interaction of the *Triticum aestivum* nucleus and *Triticum timopheevii* cytoplasm. Wheat Information Service (Kyoto) 14: 29-30.

Wilson J A, Ross W M. 1962. Male sterility interaction of the *Triticum aestivum* nucleus and *Triticum timopheevii* cytoplasm. Wheat Information Service (Kyoto) 14, 29-30.

Wilson P, Driscoll C j, 1983. Hybrid Wheat. Monographs on theorical and applied genetics, Vol. 6, 94-123.

Wilson, 1984. Hybrid wheat breeding and commercial seed development. Plant Breeding Rev., 2: 303-319.2

Whitford R et al., 2013. Hybrid breeding in wheat: technologies to improve hybrid wheat seed production. Journal of Experimental Botany. Doi:10.1093/jxb/ert333.

Zhou et al., 2005. SSR marker associated with fertility restoration genes against *Triticum timopheevii* cytoplasm in *Triticum aestivum*. Euphytica, 141:33-40.

Sebesta E E, Hatchett J H, Friebe B, Gill B S, Cox T S, and Sears R G. 1997. Registration of KS92WGRC17, KS92WGRC18, KS92WGRC19, and KS92WGRC20 winter wheat germplasms resistant to Hessian fly. Crop Sci 37:635.

https://doi.org/10.2135/cropsci1997.0011183X003700020065x

Friebe B, Gill B S, Tuleen N A, and Cox T S. 1995. Crop Sci 35:1237

The invention claimed is:

1. A wheat plant restorer of fertility of *T. timopheevii* CMS cytoplasm, wherein the plant comprises at least Rf1, Rf3, and Rf4s loci.

2. The wheat plant according to claim 1, wherein said Rf1 locus is located within the chromosomal interval between SNP markers cfn0522096 of SEQ ID NO:3 and cfn05277067 of SEQ ID NO:9.

3. The wheat plant of claim 1, wherein said Rf1 locus is characterized by the presence of one or more of the following SNP restorer allele(s):

| SNP# | Marker Name | Marker SEQ ID NO: | Restorer Allele |
|---|---|---|---|
| SNP1 | cfn0523109 | 1 | A |
| SNP2 | 276I13_96B22_97797 | 2 | C |
| SNP3 | cfn0522096 | 3 | C |
| SNP4 | cfn0527763 | 4 | C |
| SNP5 | 104A4_105172 | 5 | TG |
| SNP6 | 104A4_105588 | 6 | A |
| SNP7 | cfn0373248 | 7 | T |
| SNP8 | cfn1097828 | 8 | C |
| SNP9 | cfn0527067 | 9 | A |
| SNP10 | cfn0528390 | 10 | G |
| SNP11 | BWS0267 | 11 | A |
| SNP12 | cfn0527718 | 12 | T |
| SNP13 | cfn0524469 | 13 | G |
| SNP14 | cfn0524921 | 14 | G |
| SNP15 | cfn1122326 | 15 | C |
| SNP16 | RFL79_S7 | 16 | G. |

4. The wheat plant according to claim 1, wherein said Rf1 locus is characterized by the presence of at least a nucleic acid of SEQ ID NO: 64 or a nucleic acid encoding an amino acid sequence having at least 95% identity, preferably 96%, 97%, 98%, 99% or 100% identity to SEQ ID NO:64.

5. The wheat plant according to claim 1, wherein the Rf3 locus is located within the chromosomal fragment between SNP markers cfn1249269 of SEQ ID NO:19 and BS00090770 of SEQ ID NO:42.

6. The wheat plant according to claim 1, wherein said Rf3 locus is characterized by the presence of one or more of the following SNP restorer allele(s):

| SNP# | Marker Name | Marker SEQ ID | Restorer Allele |
|---|---|---|---|
| SNP17 | cfn1252000 | 17 | A |
| SNP18 | IWB14060* | 18 | G |
| SNP19 | cfn1249269 | 19 | G |
| SNP20 | 219K1_166464 | 20 | T |
| SNP21 | 219K1_158251 | 21 | G |
| SNP22 | 219K1_111446 | 22 | A |
| SNP23 | 219K1_110042 | 23 | T |
| SNP24 | 219K1_110005 | 24 | C |
| SNP25 | 219K1_107461 | 25 | A |
| SNP26 | 219K1_99688 | 26 | T |
| SNP27 | 219K1_37 | 27 | C |
| SNP28 | cfn1270524 | 28 | T |
| SNP29 | 136H5_3M5_7601 | 29 | T |
| SNP30 | cfn1288811 | 30 | G |
| SNP31 | 136H5_3M5_89176 | 31 | A |
| SNP32 | 136H5_3M5_89263 | 32 | T |
| SNP33 | 136H5_3M5_138211 | 33 | T |
| SNP34 | cfn0556874 | 34 | C |
| SNP35 | 136H5_3M5_64154 | 35 | C |
| SNP36 | 136H5_3M5_68807 | 36 | G |
| SNP37 | 136H5_3M5_77916 | 37 | A |
| SNP38 | cfn1246088 | 38 | A |
| SNP39 | cfn1287194 | 39 | G |
| SNP40 | cfn1258380 | 40 | A |
| SNP41 | IWB72107* | 41 | A |
| SNP42 | BS00090770 | 42 | T |
| SNP43 | cfn1239345 | 43 | A |
| SNP44 | RFL29_S2 | 44 | G |
| SNP45 | RFL29_S4 | 45 | C. |

7. The wheat plant according to claim 5, wherein said Rf3 locus is characterized by the presence of a nucleic acid encoding an amino acid sequence having at least 95% identity, preferably at least 96%, 97%, 98%, 99% or 100% identity to an amino acid selected from the group consisting of SEQ ID NO: 70, SEQ ID NO: 71 and SEQ ID NO:72.

8. The wheat plant according to claim 1, wherein said Rf4s locus is located within the chromosomal interval between SNP markers TaContig158085_61_BS00011513 of SEQ ID NO:46 and cfn0864865 of SEQ ID NO:47.

9. The wheat plant according to claim 1, wherein said Rf4s locus comprises any Ae *Speltoides* SNP on the short arm of the chromosome 6B on the area ranging from 0 to 32 334 597 bases according to IWGSC V1 reference.

10. The wheat plant of claim 8, wherein said Rf4s locus is characterized by the presence of one or more of the following SNP allele(s):

| SNP# | Marker Name | Marker SEQ ID | Restorer Allele |
|---|---|---|---|
| SNP46 | TaContig158085_61_BS00011513 | 46 | T |
| SNP47 | cfn0864865 | 47 | G |
| SNP48 | EXCALIBUR_C96134_152 | 48 | C |
| SNP49 | cfn3133296 | 49 | G |
| SNP50 | LWE1_chr6B_485210_Rf4S | 50 | T |
| SNP51 | LWE1_chr6B_11287944_Rf4S | 51 | G |
| SNP52 | LWE1_chr6B_19775886_Rf4S | 52 | G |
| SNP53 | LWE1_chr6B_28157776_Rf4S | 53 | C. |

11. The wheat according to claim 1, wherein the plant also comprises Rf7 and/or 6R locus.

12. The wheat plant according to claim 11, wherein the Rf7 locus is located at most 10 cM from SNP marker cfn0919993 of SEQ ID NO:55.

13. The wheat plant according to claim 11, wherein said Rf7 locus is characterized by the presence of one or more of the following restorer SNP allele(s):

| SNP# | Marker Name | Marker SEQ ID | Restorer Allele |
|---|---|---|---|
| SNP54 | cfn0917304 | 54 | T |
| SNP55 | cfn0919993 | 55 | G |
| SNP56 | cfn0920459 | 56 | C |
| SNP57 | cfn0915987 | 57 | G |
| SNP58 | cfn0920253 | 58 | A |
| SNP59 | cfn0448874 | 59 | T |
| SNP60 | cfn0923814 | 60 | C |
| SNP61 | cfn0924180 | 61 | G |
| SNP62 | cfn0919484 | 62 | G |
| SNP64 | LWE1_chr7B_658281643_Rf7 | 263 | G |
| SNP65 | LWE1_chr7B_711539100_Rf7 | 264 | A. |

14. The wheat plant according to claim 11, wherein the Rf7 locus is characterized by the haplotype "T", "G", "C", "G", "A", "T", "C", "G", "G", "G" and "A" and of the SNP54 to SNP62 and SNP64 to SNP65 restorer alleles:

| SNP# | Marker Name | Marker SEQ ID | Restorer Allele |
|---|---|---|---|
| SNP54 | cfn0917304 | 54 | T |
| SNP55 | cfn0919993 | 55 | G |
| SNP56 | cfn0920459 | 56 | C |
| SNP57 | cfn0915987 | 57 | G |
| SNP58 | cfn0920253 | 58 | A |
| SNP59 | cfn0448874 | 59 | T |
| SNP60 | cfn0923814 | 60 | C |
| SNP61 | cfn0924180 | 61 | G |
| SNP62 | cfn0919484 | 62 | G |
| SNP64 | LWE1_chr7B_658281643_Rf7 | 263 | G |
| SNP65 | LWE1_chr7B_711539100_Rf7 | 264 | A. |

15. The wheat plant according to claim 11, wherein it further includes the 6R locus, said 6R locus being located on chromosome 6R and within the chromosomal interval between 48.9 cM to 114.8 cM.

16. The wheat plant according to claim 11, wherein said 6R locus is characterized by the presence of the following restorer SNP allele:

| SNP# | Marker Name | Marker SEQ ID | Restorer Allele |
|---|---|---|---|
| SNP63 | RFL46_S2 | 63 | A. |

17. The wheat plant of claim 1, wherein representative alleles of Rf1, Rf3, and Rf4s is provided by the seed sample NCIMB 43746.

18. The wheat plant according to claim 1, wherein said wheat plant is alloplasmic and comprises the *T. timopheevii* cytoplasm.

19. A method for producing a wheat hybrid plant comprising the steps of:
 a. crossing a sterile female comprising the *T. timopheevii* cytoplasm with a fertile male wheat plant according to claim 1;
 b. collecting the hybrid seed;
 c. optionally detecting the presence of *T. timopheevii* cytoplasm, and/or at least three of the Rf locus chosen amongst Rf1, Rf3, Rf4s, Rf7 and 6R in the hybrid seed;
 d. optionally detecting hybridity level of the hybrid seeds.

20. The method of claim 19, further comprising after step b., a step of detecting the presence of *T. timopheevii* cytoplasm, and/or the Rf1, Rf3, and Rf4s restorer alleles in the hybrid seeds.

21. The method of claim 20, further comprising a step of detecting the presence of loci Rf7 or 6R in the hybrid seeds.

22. A method for producing a wheat hybrid seed comprising the steps of:
 a. crossing a first and a second wheat plant two plants according to claim 1;
 b. collecting the hybrid seed;
 c. optionally detecting hybridity level of the hybrid seeds.

23. The method of claim 22, wherein the fertility score of the obtained wheat plant has a fertility score higher than the parent wheat plant.

24. A wheat hybrid plant as obtained by the method of claim 19.

25. A method of identifying a wheat plant according to claim 1, wherein said wheat plant is identified by detecting the presence of at least one restorer allele within one or more of Rf1, Rf3, and Rf4s loci.

26. A method for producing the wheat plant restorer of fertility of claim 1, said method comprising the following steps:
 a. providing a first wheat plant comprising one or two restorer allele selected among Rf1, Rf3 and Rf4s restorer alleles,
 b. crossing said first wheat plant with a second wheat plant comprising one or two restorer alleles selected among Rf1, Rf3 and Rf4s restorer alleles, wherein Rf1, Rf3 and Rf4s restorer alleles are represented at least once in the panel of restorer alleles provided by the first plant and the second plant,
 c. collecting the F1 hybrid seed,
 d. obtaining homozygous plants from the F1 plants,
 e. detecting the presence of the Rf1, Rf3 and Rf4s restorer alleles in the hybrid seed and/or at each generation.

27. A method for producing a wheat plant restorer of fertility of *T. timopheevii* CMS cytoplasm, said method comprising the following steps:
 a. providing a first wheat plant comprising at least Rf1, Rf3 and Rf4s restorer alleles according to claim 1,
 b. crossing said first wheat plant with a second wheat plant,
 c. collecting the F1 hybrid seed,
 d. obtaining homozygous plants from the F1 plants,
 e. optionally detecting the presence of the Rf1, Rf3 and Rf4s restorer alleles in the hybrid seed and/or at each generation, and optionally further detecting the presence of Rf7 and/or 6R restorer alleles in the hybrid seed and/or at each generation.

28. A method for producing a wheat plant restorer of fertility, said method comprising the following steps:
 a. crossing a first wheat plant according to claim 1 with a second wheat plant; thereby obtaining a F1 hybrid plant;
 b. backcrossing said F1 hybrid with the second wheat plant;
 c. selecting the wheat plant restorer of fertility among the wheat plant obtained in step b) by detecting the presence of at least Rf1, Rf3 and Rf4s restorer alleles, and optionally further detecting the presence of Rf7 and/or 6R restorer alleles.

29. The method for producing a wheat plant restorer of fertility according to claim 28, said method further comprises one or more step of backcrossing the wheat plant selected by detecting the presence of at least Rf1, Rf3 and Rf4s restorer alleles.

30. The method for producing a wheat plant restorer of fertility according to claim 28, wherein the second wheat plant is an elite wheat line.

31. The wheat plant of claim 15, wherein representative alleles of Rf 1, Rf3, and 6R is provided by the seed sample NCIMB 43747.

32. A method of identifying a wheat plant according to claim 11, wherein said wheat plant is identified by detecting the presence of at least one restorer allele within one or more of Rf7 and 6R loci.

* * * * *